United States Patent
Anderson et al.

(10) Patent No.: US 9,956,345 B2
(45) Date of Patent: May 1, 2018

(54) WEARABLE AUTOMATIC INJECTION DEVICE FOR CONTROLLED ADMINISTRATION OF THERAPEUTIC AGENTS

(75) Inventors: Philip D. Anderson, Libertyville, IL (US); Joseph F. Julian, Libertyville, IL (US); Linas P. Laurusonis, Lake Villa, IL (US); Sean Corrigan, Chicago, IL (US); William Fienup, St. Louis, MO (US); Tomas Matusaitis, Chicago, IL (US); Chris Strahm, Deforest, WI (US)

(73) Assignee: AbbVie Inc., North Chicago, IL (US)

( * ) Notice: Subject to any disclaimer, the term of this patent is extended or adjusted under 35 U.S.C. 154(b) by 1081 days.

(21) Appl. No.: 14/111,933

(22) PCT Filed: Apr. 23, 2012

(86) PCT No.: PCT/US2012/034683
§ 371 (c)(1),
(2), (4) Date: Jan. 20, 2014

(87) PCT Pub. No.: WO2012/145752
PCT Pub. Date: Oct. 26, 2012

(65) Prior Publication Data
US 2014/0148784 A1    May 29, 2014

Related U.S. Application Data

(60) Provisional application No. 61/478,039, filed on Apr. 21, 2011.

(51) Int. Cl.
*A61M 31/00* (2006.01)
*A61M 1/00* (2006.01)
(Continued)

(52) U.S. Cl.
CPC .......... *A61M 5/2053* (2013.01); *A61M 5/002* (2013.01); *A61M 5/14248* (2013.01);
(Continued)

(58) Field of Classification Search
CPC .. A61M 2005/14252; A61M 2005/247; A61M 35/00; A61M 5/002;
(Continued)

(56) References Cited

U.S. PATENT DOCUMENTS 3,824,859 A * 7/1974 Harris, Sr. ......... G01N 35/1079
73/864.87
3,910,260 A   10/1975 Sarnoff et al.
(Continued)

FOREIGN PATENT DOCUMENTS

CN    1726059 A    1/2006
EP    0125023 A1   11/1984
(Continued)

OTHER PUBLICATIONS

Beidler C.B., et al., "Cloning and High Level Expression of a Chimeric Antibody with Specificity for Human Carcinoembryonic Antigen," The Journal of Immunology, 1988, vol. 141 (11), pp. 4053-4060.
(Continued)

*Primary Examiner* — Jason Flick
(74) *Attorney, Agent, or Firm* — McCarter & English, LLP; David R. Burns

(57) ABSTRACT

Exemplary embodiments provide wearable automatic injection devices for administering a therapeutic agent to a patient's body at fast, controlled rates, for example, in a single fast bolus. Exemplary embodiments also provide methods for assembling wearable automatic injection devices for administering a therapeutic agent to a patient at fast, controlled rates. Exemplary embodiments also provide
(Continued)

methods for using wearable automatic injection devices for administering a therapeutic agent to a patient at fast, controlled rates.

49 Claims, 58 Drawing Sheets

(51) Int. Cl.

| | |
|---|---|
| *A61M 5/20* | (2006.01) |
| *A61M 5/142* | (2006.01) |
| *A61M 5/00* | (2006.01) |
| *A61M 35/00* | (2006.01) |
| A61M 5/32 | (2006.01) |
| A61M 5/24 | (2006.01) |
| A61M 5/145 | (2006.01) |

(52) U.S. Cl.
CPC ............ *A61M 5/20* (2013.01); *A61M 5/2466* (2013.01); *A61M 5/3202* (2013.01); *A61M 5/3232* (2013.01); *A61M 35/00* (2013.01); A61M 5/1452 (2013.01); A61M 5/3234 (2013.01); A61M 2005/14252 (2013.01); A61M 2005/247 (2013.01); Y10T 29/49826 (2015.01)

(58) Field of Classification Search
CPC .. A61M 5/14248; A61M 5/1452; A61M 5/20; A61M 5/2053; A61M 5/2466; A61M 5/3202; A61M 5/3232; A61M 5/3234
USPC ........................................................ 604/506
See application file for complete search history.

(56) References Cited

U.S. PATENT DOCUMENTS

| | | | |
|---|---|---|---|
| 3,941,130 | A | 3/1976 | Tibbs |
| 4,004,577 | A | 1/1977 | Sarnoff |
| 4,261,358 | A | 4/1981 | Vargas et al. |
| 4,689,042 | A | 8/1987 | Sarnoff et al. |
| 4,755,169 | A | 7/1988 | Sarnoff et al. |
| 4,795,433 | A | 1/1989 | Sarnoff |
| 4,816,567 | A | 3/1989 | Cabilly et al. |
| 5,085,642 | A | 2/1992 | Sarnoff et al. |
| 5,092,843 | A | 3/1992 | Monroe et al. |
| 5,102,393 | A | 4/1992 | Sarnoff et al. |
| 5,225,539 | A | 7/1993 | Winter |
| 5,267,963 | A | 12/1993 | Bachynsky |
| 5,530,101 | A | 6/1996 | Queen et al. |
| 5,585,089 | A | 12/1996 | Queen et al. |
| 5,656,272 | A | 8/1997 | Le et al. |
| 5,693,761 | A | 12/1997 | Queen et al. |
| 5,693,762 | A | 12/1997 | Queen et al. |
| 5,814,020 | A | 9/1998 | Gross |
| 5,860,957 | A * | 1/1999 | Jacobsen .................. A61N 1/30 604/140 |
| 6,090,382 | A | 7/2000 | Salfeld et al. |
| 6,149,626 | A | 11/2000 | Bachynsky et al. |
| 6,258,562 | B1 | 7/2001 | Salfeld et al. |
| 6,270,479 | B1 | 8/2001 | Bergens et al. |
| 6,371,939 | B2 | 4/2002 | Bergens et al. |
| 6,448,380 | B2 | 9/2002 | Rathjen et al. |
| 6,451,983 | B2 | 9/2002 | Rathjen et al. |
| 6,498,237 | B2 | 12/2002 | Rathjen et al. |
| 6,509,015 | B1 | 1/2003 | Salfeld et al. |
| 6,593,458 | B1 | 7/2003 | Rathjen et al. |
| 7,223,394 | B2 | 5/2007 | Salfeld et al. |
| 7,250,165 | B2 | 7/2007 | Heavner et al. |
| 7,521,206 | B2 | 4/2009 | Heavner et al. |
| 2001/0025168 | A1 | 9/2001 | Gross et al. |
| 2009/0093792 | A1* | 4/2009 | Gross ................ A61M 5/14566 604/518 |
| 2010/0168683 | A1 | 7/2010 | Cabiri | |
| 2011/0166512 | A1* | 7/2011 | Both ................ A61M 5/14248 604/67 |
| 2012/0123387 | A1* | 5/2012 | Gonzalez .......... A61M 37/0015 604/506 |

FOREIGN PATENT DOCUMENTS

| | | |
|---|---|---|
| EP | 0171496 A2 | 2/1986 |
| EP | 173494 A2 | 3/1986 |
| EP | 0184187 A2 | 6/1986 |
| JP | 2007502169 A | 2/2007 |
| WO | 8601533 A1 | 3/1986 |
| WO | 8702671 A1 | 5/1987 |
| WO | 9007861 A1 | 7/1990 |
| WO | 9103553 A1 | 3/1991 |
| WO | 9406476 A1 | 3/1994 |
| WO | 0212502 A2 | 2/2002 |
| WO | 03039433 A1 | 5/2003 |
| WO | 2004024211 A2 | 3/2004 |
| WO | 2008005315 A2 | 1/2008 |
| WO | 2010029054 A1 | 3/2010 |
| WO | 2011014514 A1 | 2/2011 |
| WO | 2011014704 A2 | 2/2011 |

OTHER PUBLICATIONS

Better M., et al. "*Escherichia coli* Secretion of an Active Chimeric Antibody Fragment," Science, 1988, vol. 240 (4855) pp. 1041-1043.
Bird R.E., et al., "Single-Chain Antigen-Binding Proteins," Science, 1988, vol. 242 (4877), pp. 423-426.
Davis J.M., et al., "Structure of Human Tumor Necrosis Factor Alpha Derived from Recombinant DNA," Biochemistry, 1987, vol. 26 (5), pp. 1322-1326.
Holliger P., et al., ""Diabodies": Small Bivalent and Bispecific Antibody Fragments," Proceedings of the National Academy of Sciences, 1993, vol. 90 (14), pp. 6444-6448.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences, 1988, vol. 85 (16), pp. 5879-5883.
International Search Report for Application No. PCT/US2012/034683, dated Feb. 7, 2013, 7 pages.
Jones E.Y., et al., "Structure of Tumour Necrosis Factor," Nature, 1989, vol. 338 (6212), pp. 225-228.
Jones P.T., et al., "Replacing the Complementarity-Determining Regions in a Human Antibody with those from a Mouse," Nature, 1986, vol. 321 (6069), pp. 522-525.
Liu A.Y., et al., "Chimeric Mouse-human IgG1 Antibody that can Mediate Lysis of Cancer Cells," Proceedings of the National Academy of Sciences, 1987, vol. 84 (10), pp. 3439-3443.
Liu A.Y., et al., "Production of a Mouse-Human Chimeric Monoclonal Antibody to CD20 with Potent Fc-dependent Biologic Activity," Journal of Immunology, 1987, vol. 139 (10), pp. 3521-3526.
Morrison S.L., "Transfectomas Provide Novel Chimeric Antibodies," Science, 1985, vol. 229 (4719), pp. 1202-1207.
Nishimura Y., et al., "Recombinant Human-mouse Chimeric Monoclonal Antibody Specific for Common Acute Lymphocytic Leukemia Antigen," Cancer Research, 1987, vol. 47 (4), pp. 999-1005.
Ol V.T., et al., "Chimeric Antibodies," BioTechniques, 1986, vol. 4 (3), pp. 214-221.
Pennica D., et al., "Human Tumour Necrosis Factor: Precursor Structure, Expression and Homology to Lymphotoxin," Nature, 1984, vol. 312 (5996), pp. 724-729.
Poljak R.J., "Production and Structure of Diabodies," Structure, 1994, vol. 2 (12), pp. 1121-1123.
Queen C., et al., "A Humanized Antibody that Binds to the Interleukin 2 Receptor," Proceedings of National Academy of Sciences USA, 1989, vol. 86 (24), pp. 10029-10033.
Shaw D.R., et al., "Mouse/human Chimeric Antibodies to a Tumor-associated Antigen: Biologic Activity of the four Human IgG Subclasses.," Journal of the National Cancer Institute, 1988, vol. 80 (19), pp. 1553-1559.

(56) References Cited

OTHER PUBLICATIONS

Sun L.K., et al., "Chimeric Antibody with Human Constant Regions and Mouse Variable Regions Directed Against Carcinoma-associated Antigen 17-1A," Proceedings of the National Academy of Sciences, 1987, vol. 84 (1), pp. 214-218.
Taylor L.D., et al., "A Transgenic Mouse that Expresses a Diversity of Human Sequence Heavy and Light Chain Immunoglobulins," Nucleic Acids Research, 1992, vol. 20 (23), pp. 6287-6295.
Verhoeyen M., et al., "Reshaping Human Antibodies: Grafting an Antilysozyme Activity ," Science, 1988, vol. 239, pp. 1534-1536.
Ward E.S., et al., "Binding Activities of a Repertoire of Single Immunoglobulin Variable Domains Secreted from *Escherichia coli*," Nature, 1989, vol. 341 (6242), pp. 544-546.
Wood C.R., et al., "The Synthesis and in Vivo Assembly of Functional Antibodies in Yeast," Nature, 1985, vol. 314 (6010), pp. 446-449.
Examination Report No. 2 issued in Australian Application No. 2012245211, dated Jul. 8, 2015.
International Preliminary Report on Patentability issued in International Application No. PCT/US2012/034683, dated Oct. 22, 2013.
Office Action issued in Chinese Patent Application No. 201280030740.9, dated Oct. 16, 2015.
Written Opinion issued in International Application No. PCT/US2012/034683, dated Feb. 7, 2013.

\* cited by examiner

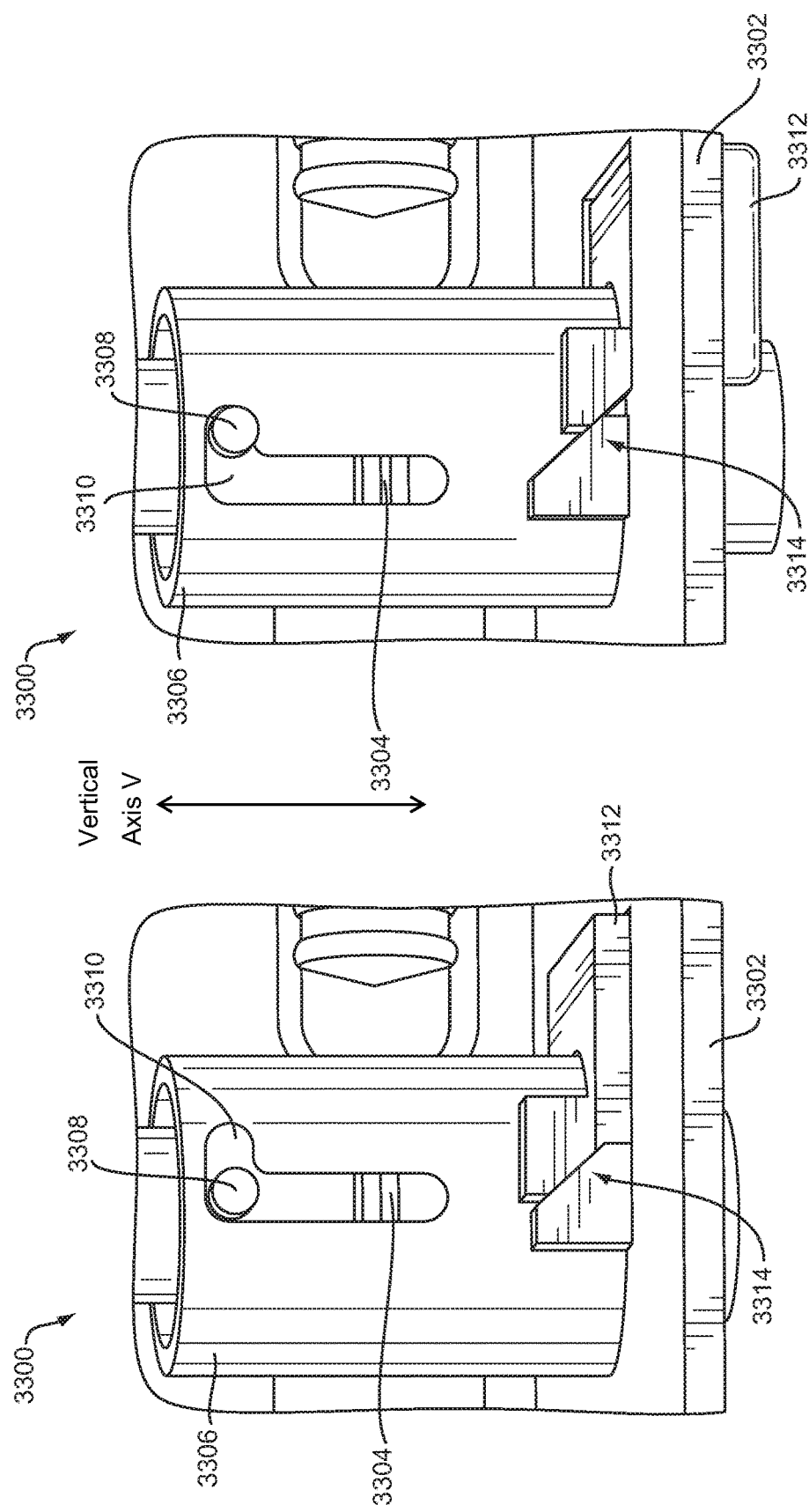

WEARABLE AUTOMATIC INJECTION DEVICE FOR CONTROLLED ADMINISTRATION OF THERAPEUTIC AGENTS

RELATED APPLICATIONS

This application is a non-provisional of and claims the benefit of priority to U.S. Provisional Patent Application Ser. No. 61/478,039, filed Apr. 21, 2011. This application is also related to U.S. patent application Ser. No. 13/092,102, filed Apr. 21, 2011 (published as U.S. Patent Publication No. 2012-0022499 A1 on Jan. 26, 2012). The entire contents of each of the above-referenced applications are expressly incorporated herein by reference in their entirety.

BACKGROUND

Automatic injection devices offer an alternative to manually-operated syringes for administering therapeutic agents into patients' bodies and allowing patients to self-administer therapeutic agents. Automatic injection devices have been used to administer medications under emergency conditions, for example, to administer epinephrine to counteract the effects of a severe allergic reaction. Automatic injection devices have also been described for use in administering anti-arrhythmic medications and selective thrombolytic agents during a heart attack (See, for example, U.S. Pat. Nos. 3,910,260; 4,004,577; 4,689,042; 4,755,169; and 4,795,433). Various types of automatic injection devices are also described in, for example, U.S. Pat. Nos. 3,941,130; 4,261,358; 5,085,642; 5,092,843; 5,102,393; 5,267,963; 6,149,626; 6,270,479; and 6,371,939; and PCT Publication No. WO/2008/005315, all of which are incorporated herein in their entirety by reference.

Conventionally, an automatic injection device houses a syringe and, when operated, causes the syringe to move forwardly and a needle to project from the housing so that a therapeutic agent contained in the syringe is administered to a patient's body. Conventional automatic injection devices include hand-held automatic injection devices and patch pumps, which are self-adhesive, patient-mounted auto-injectors. In use, a patch pump containing a therapeutic agent is mounted onto the body or clothing of a patient and triggered to administer the therapeutic agent to the patient. Conventional patch pumps are typically filled by a patient prior to use. In addition, certain conventional patch pumps have an exposed needle inside the pump, and thus require secondary sterile packaging to maintain sterility.

SUMMARY

Exemplary embodiments provide wearable automatic injection devices that may adhere to the skin or clothing of a patient and administer a therapeutic agent to the patient at fast, controlled administration rates, for example, in a single fast bolus. Exemplary embodiments also provide methods of assembling wearable automatic injection devices. Exemplary embodiments also provide methods of using wearable automatic injection devices worn by a patient for fast, controlled therapeutic agent administration. Exemplary wearable automatic injection devices reduce or eliminate a burning sensation often felt or perceived by patients who use a conventional automatic injection device. Exemplary wearable automatic injection devices maintain sterility of the therapeutic agent (for example, a syringe), are easy to use, pre-fill capable, easy to manufacture, and/or do not require aseptic assembly. The wearable automatic injection devices provided by exemplary embodiments be used to administer any therapeutic agent to a patient including, but not limited to, a biologic drug, such as, for example, a TNFα inhibitor, an antibody, insulin, and the like.

In accordance with an exemplary embodiment, a wearable automatic injection device is provided for administering a therapeutic agent to a patient. The device includes a housing including a patient contact portion for contacting the skin of the patient. The device also includes an administration assembly moveably disposed in the housing and bearing an administration interface for administering the therapeutic agent to the patient. The administration assembly is moveable between a retracted position in which the administration interface does not protrude outside the housing and an extended position in which the administration interface protrudes outside the housing. The device also includes a vessel provided in the housing for holding the therapeutic agent and a plunger actuation mechanism moveably disposed in the vessel for ejecting the therapeutic agent from the vessel into the administration assembly. A volume of the therapeutic agent of between 0.1 milliliters and 1.0 milliliter is ejected from the vessel in less than thirty seconds.

In accordance with another exemplary embodiment, a method is provided for administering a therapeutic agent to a patient. The method includes providing a wearable automatic injection device including a housing including a patient contact portion for contacting the skin of the patient. The device also includes an administration assembly moveably disposed in the housing and bearing an administration interface for administering the therapeutic agent to the patient. The administration assembly is moveable between a retracted position in which the administration interface does not protrude outside the housing and an extended position in which the administration interface protrudes outside the housing. The device also includes a vessel provided in the housing for holding the therapeutic agent and a plunger actuation mechanism moveably disposed in the vessel for ejecting the therapeutic agent from the vessel into the administration assembly. The method includes securing the wearable automatic injection device to the skin of the patient using the patient contact portion of the housing. The method also includes administering a volume of the therapeutic agent of between 0.1 milliliters and 1.0 milliliter to the patient using the wearable automatic injection device in less than thirty seconds.

In accordance with another exemplary embodiment, a method is provided for assembling a wearable automatic injection device. The method includes assembling a first portion of the automatic injection device in a sterile environment to hold a sterile dose of a therapeutic agent. The method includes providing one or more sterility bather components associated with the first portion of the device to maintain sterility, during and after assembly of the automatic injection device, of a fluid pathway taken by the therapeutic agent during administration to a patient. The method also includes assembling a second portion of the automatic injection device in a non-sterile environment while maintaining sterility of the first portion of the automatic injection device.

In accordance with another exemplary embodiment, a wearable automatic injection device is provided for administering a therapeutic agent to a patient. The device includes a housing including a patient contact portion for contacting the skin of the patient. The device also includes an administration assembly moveably disposed in the housing and bearing an administration interface for administering the therapeutic agent to the patient, the administration assembly moveable between a retracted position in which the administration interface does not protrude outside the housing and an extended position in which the administration interface protrudes outside the housing. The device also includes a vessel provided in the housing for holding the therapeutic agent and a plunger actuation mechanism moveably disposed in the vessel for ejecting the therapeutic agent from the vessel into the administration assembly. The device also includes a retraction trigger responsive to a change of state of the wearable automatic injection device from an administration state to a post-administration state, and a retraction mechanism for automatically retracting the administration assembly from the extended position in the administration state to the retracted position in the post-administration state upon triggering by the retraction trigger. A volume of the therapeutic agent of between 0.1 milliliters and 1.0 milliliter is ejected from the vessel in less than thirty seconds.

In accordance with another exemplary embodiment, a method is provided for administering a therapeutic agent to a patient. The method includes providing a wearable automatic injection device including a housing including a patient contact portion for contacting the skin of the patient. The device also includes an administration assembly moveably disposed in the housing and bearing an administration interface for administering the therapeutic agent to the patient, the administration assembly moveable between a retracted position in which the administration interface does not protrude outside the housing and an extended position in which the administration interface protrudes outside the housing. The device also includes a vessel provided in the housing for holding the therapeutic agent and a plunger actuation mechanism moveably disposed in the vessel for ejecting the therapeutic agent from the vessel into the administration assembly. The device also includes a retraction trigger responsive to a change of state of the wearable automatic injection device from an administration state to a post-administration state, and a retraction mechanism for automatically retracting the administration assembly from the extended position in the administration state to the retracted position in the post-administration state upon triggering by the retraction trigger. The method includes securing the wearable automatic injection device to the skin of the patient using the patient contact portion of the housing. The method also includes administering a volume of the therapeutic agent of between 0.1 milliliters and 1.0 milliliter to the patient using the wearable automatic injection device in less than thirty seconds.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIGS. 33A and 33B illustrate another exemplary administration interface protection system that maintains an administration interface in a retracted position within the housing of an exemplary automatic injection device.

DETAILED DESCRIPTION

Figure 1A:
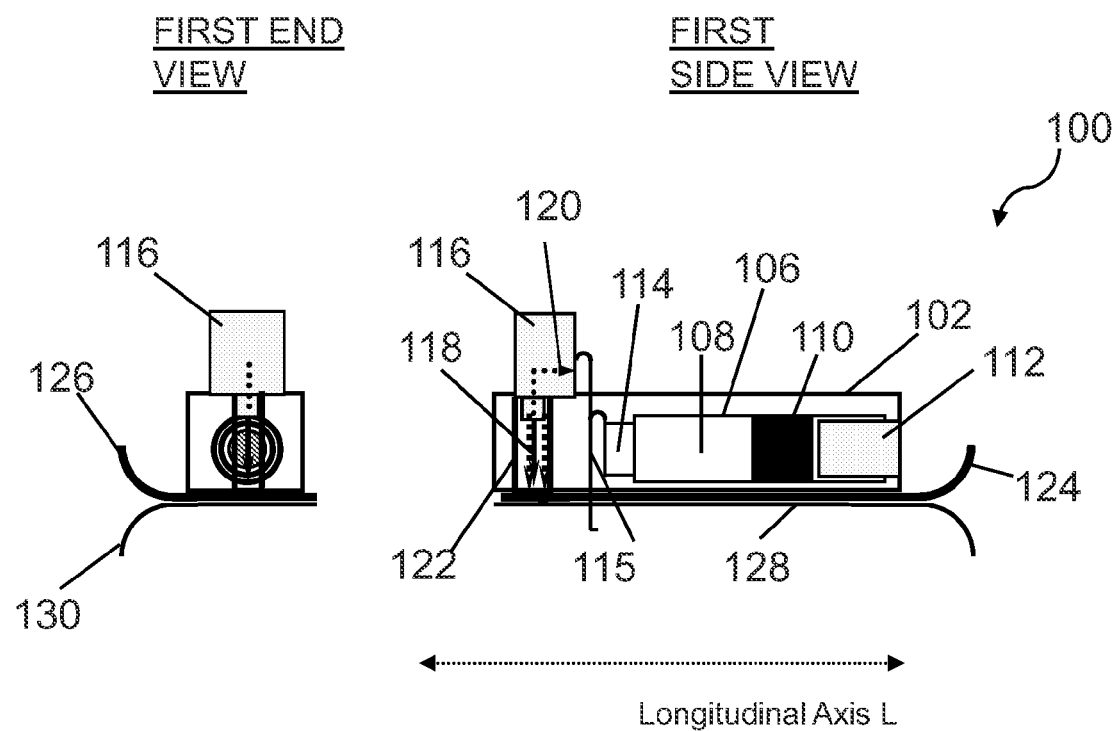
FIG. 1A illustrates a first end view and a first side view of an exemplary wearable device including a cartridge assembly in a packaged pre-administration state.

Automatic injection devices offer an alternative to conventional manually-operated syringes for administering a therapeutic agent and allow patients to self-administer therapeutic agents. Exemplary embodiments provide wearable automatic injection devices that may adhere to the body or clothing of a patient's body and administer a therapeutic agent to the patient at fast, controlled administration rates, for example, in a single fast bolus. Exemplary embodiments also provide methods of using the wearable automatic injection devices for fast, controlled therapeutic agent administration.

In an exemplary embodiment, a volume of about 0.1 milliliters to about 1 milliliter or more of a therapeutic agent may be administered in an administration time period of about one second to about twelve hours. In an exemplary embodiment, the administration time period for the same range of volumes may range from about one second to about thirty seconds, but is not limited to this exemplary range. In certain exemplary embodiments, therapeutic agent volumes of about 0.1 milliliters to about 1 milliliter may be administered in a time duration ranging from about 3 seconds to about 5 seconds. In certain exemplary embodiments, therapeutic agent volumes of about 0.1 milliliters to about 1 milliliter may be administered in time durations of or shorter than about 20 seconds.

Exemplary wearable automatic injection devices are disposable, easy to use, pre-fill capable, and may substantially or completely eliminate the burning sensation often experienced by a patient that uses a wearable automatic injection device. The fast, controlled administration rates achieved by exemplary devices may minimize the pain sensation associated with a volume of a therapeutic agent entering into the patient's tissue. Exemplary time durations for fast administration achieved by exemplary devices may range from about one second to about thirty seconds, but are not limited to this exemplary range. Exemplary volumes of therapeutic agent that may be administered by exemplary devices within the above time range may range from about 0.1 milliliters to about 1 milliliter, but are not limited to this exemplary range. In certain exemplary embodiments, therapeutic agent volumes of about 0.1 milliliters to about 1 milliliter may be administered in a time duration ranging from about 3 seconds to about 5 seconds. In certain exemplary embodiments, therapeutic agent volumes of about 0.1 milliliters to about 1 milliliter may be administered in a time duration of or shorter than about 20 seconds. In addition, exemplary devices may advantageously provide a linear administration profile, i.e., at a substantially constant rate of administration, and may minimize inflections and abrupt changes in the administration profile against time of the therapeutic agent.

Exemplary embodiments minimize the size envelope of exemplary automatic injection devices and provide scalable solutions with configurable administration times and administration profiles that may be used for a range of therapeutic agent viscosities.

Exemplary embodiments may administer a therapeutic agent to a patient without requiring battery power or other components requiring electrical current or charge to operate.

The wearable automatic injection devices provided by exemplary embodiments are pre-fillable and/or pre-filled prior to administration to the patient, maintain sterility of the therapeutic agent, sterility of all therapeutic agent contact surfaces and patient contact surfaces (i.e., a vessel containing the therapeutic agent, one or more fluid conduits in the device, one or more skin penetrating surfaces of an administration interface, one or more septa provided in the fluid conduits, and the like) and sterility of the administration pathway taken by the therapeutic agent during administration to the patient, in order to avoid the need for aseptic assembly, and address the perceived patient discomfort due to injection by conventional hand held automatic injection devices. Exemplary wearable automatic injection devices include a primary therapeutic barrel portion that maintains sterility and therefore requires no aseptic assembly.

Exemplary automatic injection devices may be used to administer therapeutic agents in any suitable delivery injection depth by, for example, subcutaneous injection, intradermal injection, intramuscular injection, topical administration, and the like. The wearable automatic injection devices provided by exemplary embodiments may be used to administer any therapeutic agent including, but not limited to, an antibody, small molecule, insulin, and the like. A syringe assembly of exemplary automatic injection devices may contain a dose of a TNFα inhibitor. In an exemplary embodiment, the TNFα inhibitor may be a human TNFα antibody or antigen-biding portion thereof. In an exemplary embodiment, the human TNFα antibody or antigen-binding portion thereof may be adalimumab or golimumab.

Exemplary embodiments are described below with reference to certain illustrative embodiments. While exemplary embodiments are described with respect to using a wearable automatic injection device to administer a dose of a liquid medication, one of ordinary skill in the art will recognize that exemplary embodiments are not limited to the illustrative embodiments and that exemplary automatic injection devices may be used to administer any suitable substance to a patient. In addition, components of exemplary automatic injection devices and methods of making and using exemplary automatic injection devices are not limited to the illustrative embodiments described below.

I. Definitions

Certain terms are defined in this section to facilitate understanding of exemplary embodiments.

The wearable automatic injection device of exemplary embodiments may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the patient, and the ability of the antibody, antibody portion, or other TNFα inhibitor to elicit a desired response in the patient. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in patients prior to or at an earlier stage of disease, the prophylactically effective amount will be less than the therapeutically effective amount.

The terms "substance" and "therapeutic agent" refer to any type of drug, biologically active agent, biological substance, chemical substance or biochemical substance that is capable of being administered in a therapeutically effective amount to a patient employing exemplary automatic injection devices. Exemplary substances include, but are not limited to, agents in a liquid state. Such agents may include, but are not limited to, small molecule therapeutic agents. The therapeutic agent(s) may be used for treating one or more diseases or physical conditions, e.g., pain, cancer, Parkinson's disease, and the like. Such agents may also include, but are not limited to, adalimumab (HUMIRA®) and proteins that are in a liquid solution, for example, fusion proteins and enzymes. Examples of proteins in solution include, but are not limited to, Pulmozyme (Dornase alfa), Regranex (Becaplermin), Activase (Alteplase), Aldurazyme (Laronidase), Amevive (Alefacept), Aranesp (Darbepoetin alfa), Becaplermin Concentrate, Betaseron (Interferon beta-1b), BOTOX (Botulinum Toxin Type A), Elitek (Rasburicase), Elspar (Asparaginase), Epogen (Epoetin alfa), Enbrel (Etanercept), Fabrazyme (Agalsidase beta), Infergen (Interferon alfacon-1), Intron A (Interferon alfa-2a), Kineret (Anakinra), MYOBLOC (Botulinum Toxin Type B), Neulasta (Pegfilgrastim), Neumega (Oprelvekin), Neupogen (Filgrastim), Ontak (Denileukin diftitox), PEGASYS (Peginterferon alfa-2a), Proleukin (Aldesleukin), Pulmozyme (Dornase alfa), Rebif (Interferon beta-1a), Regranex (Becaplermin), Retavase (Reteplase), Roferon-A (Interferon alfa-2), TNKase (Tenecteplase), and Xigris (Drotrecogin alfa), Arcalyst (Rilonacept), NPlate (Romiplostim), Mircera (methoxypolyethylene glycol-epoetin beta), Cinryze (C1 esterase inhibitor), Elaprase (idursulfase), Myozyme (alglucosidase alfa), Orencia (abatacept), Naglazyme (galsulfase), Kepivance (palifermin) and Actimmune (interferon gamma-1b).

A protein in solution may also be an immunoglobulin or antigen-binding fragment thereof, such as an antibody or antigen-binding portion thereof. Examples of antibodies that may be used in an exemplary automatic injection device include, but are not limited to, chimeric antibodies, non-human antibodies, human antibodies, humanized antibodies, and domain antibodies (dAbs). In an exemplary embodiment, the immunoglobulin or antigen-binding fragment thereof, is an anti-TNFα and/or an anti-IL-12 antibody (for example, it may be a dual variable domain immunoglobulin (DVD) IgTM). Other examples of immunoglobulins or antigen-binding fragments thereof that may be used in the methods and compositions of exemplary embodiments include, but are not limited to, 1D4.7 (anti-IL-12/IL-23 antibody; Abbott Laboratories); 2.5(E)mg1 (anti-IL-18; Abbott Laboratories); 13C5.5 (anti-IL-13 antibody; Abbott Laboratories); J695 (anti-IL-12; Abbott Laboratories); Afelimomab (Fab 2 anti-TNF; Abbott Laboratories); HUMIRA® (adalimumab) Abbott Laboratories); Campath (Alemtuzumab); CEA-Scan Arcitumomab (fab fragment); Erbitux (Cetuximab); Herceptin (Trastuzumab); Myoscint (Imciromab Pentetate); ProstaScint (Capromab Pendetide); Remicade (Infliximab); ReoPro (Abciximab); Rituxan (Rituximab); Simulect (Basiliximab); Synagis (Palivizumab); Verluma (Nofetumomab); Xolair (Omalizumab); Zenapax (Daclizumab); Zevalin (Ibritumomab Tiuxetan); Orthoclone OKT3 (Muromonab-CD3); Panorex (Edrecolomab); Mylotarg (Gemtuzumab ozogamicin); golimumab (Centocor); Cimzia (Certolizumab pegol); Soliris (Eculizumab); CNTO 1275 (ustekinumab); Vectibix (panitumumab); Bexxar (tositumomab and I131 tositumomab); and Avastin (bevacizumab).

Additional examples of immunoglobulins, or antigen-binding fragments thereof, that may be used in the methods and compositions of exemplary embodiments include, but are not limited to, proteins comprising one or more of the following: the D2E7 light chain variable region (SEQ ID NO: 1), the D2E7 heavy chain variable region (SEQ ID NO: 2), the D2E7 light chain variable region CDR3 (SEQ ID NO: 3), the D2E7 heavy chain variable region CDR3 (SEQ ID NO:4), the D2E7 light chain variable region CDR2 (SEQ ID NO: 5), the D2E7 heavy chain variable region CDR2 (SEQ ID NO: 6), the D2E7 light chain variable region CDR1 (SEQ ID NO: 7), the D2E7 heavy chain variable region CDR1 (SEQ ID NO: 8), the 2SD4 light chain variable region (SEQ ID NO: 9), the 2SD4 heavy chain variable region (SEQ ID NO: 10), the 2SD4 light chain variable CDR3 (SEQ ID NO: 11), the EP B12 light chain variable CDR3 (SEQ ID NO: 12), the VL10E4 light chain variable CDR3 (SEQ ID NO: 13), the VL100A9 light chain variable CDR3 (SEQ ID NO: 14), the VLL100D2 light chain variable CDR3 (SEQ ID NO: 15), the VLL0F4 light chain variable CDR3 (SEQ ID NO: 16), the LOE5 light chain variable CDR3 (SEQ ID NO: 17), the VLLOG7 light chain variable CDR3 (SEQ ID NO: 18), the VLLOG9 light chain variable CDR3 (SEQ ID NO: 19), the VLLOH1 light chain variable CDR3 (SEQ ID NO: 20), the VLLOH10 light chain variable CDR3 (SEQ ID NO: 21), the VL1B7 light chain variable CDR3 (SEQ ID NO: 22), the VL1C1 light chain variable CDR3 (SEQ ID NO: 23), the VL0.1F4 light chain variable CDR3 (SEQ ID NO: 24), the VL0.1H8 light chain variable CDR3 (SEQ ID NO: 25), the LOE7.A light chain variable CDR3 (SEQ ID NO: 26), the 2SD4 heavy chain variable region CDR (SEQ ID NO: 27), the VH1B11 heavy chain variable region CDR (SEQ ID NO: 28), the VH1D8 heavy chain variable region CDR (SEQ ID NO: 29), the VH1A11 heavy chain variable region CDR (SEQ ID NO: 30), the VH1B12 heavy chain variable region CDR (SEQ ID NO: 31), the VH1E4 heavy chain variable region CDR (SEQ ID NO: 32), the VH1F6 heavy chain variable region CDR (SEQ ID NO: 33), the 3C—H2 heavy chain variable region CDR (SEQ ID NO: 34), and the VH1-D2.N heavy chain variable region CDR (SEQ ID NO: 35).

The term "human TNFα" (abbreviated herein as hTNFα, or simply hTNF) refers to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) Nature 312:724-729; Davis, J. M., et al. (1987) Biochem. 26:1322-1326; and Jones, E. Y., et al. (1989) Nature 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent that interferes with TNFα activity. The term also includes each of the anti-TNFα human antibodies (used interchangeably herein with TNFα antibodies) and antibody portions described herein as well as those described in U.S. Pat. Nos. 6,090,382; 6,258,562; 6,509,015; 7,223,394; and 6,509,015. In one embodiment, the TNFα inhibitor used in the invention is an anti-TNFα antibody, or a fragment thereof, including infliximab (Remicade®, Johnson and Johnson; described in U.S.

Pat. No. 5,656,272); CDP571 (a humanized monoclonal anti-TNF-alpha IgG4 antibody); CDP 870 (a humanized monoclonal anti-TNF-alpha antibody fragment); an anti-TNF dAb (Peptech); CNTO 148 (golimumab; Centocor, See WO 02/12502 and U.S. Pat. No. 7,521,206 and U.S. Pat. No. 7,250,165); and adalimumab (HUMIRA® Abbott Laboratories, a human anti-TNF mAb, described in U.S. Pat. No. 6,090,382 as D2E7). Additional TNF antibodies that may be used in the invention are described in U.S. Pat. Nos. 6,593,458; 6,498,237; 6,451,983; and 6,448,380. In another embodiment, the TNFα inhibitor is a TNF fusion protein, for example, etanercept (Enbrel®, Amgen; described in WO 91/03553 and WO 09/406476). In another embodiment, the TNFα inhibitor is a recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

The term "antibody" refers to immunoglobulin molecules generally comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015.

The term "antigen-binding portion" of an antibody (or simply "antibody portion") refers to one or more fragments of an antibody that retain the ability to specifically bind to an antigen (for example, hTNFα). Fragments of a full-length antibody can perform the antigen-binding function of an antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH or VL domain; (vi) an isolated complementarity determining region (CDR); and (vii) a dual variable domain immunoglobulin (DVD-Ig). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, for example, Bird et al. (1988) Science 242:423-426; and Huston et al. (1988) Proc. Natl. Acad. Sci. USA 85:5879-5883). Such single chain antibodies are also encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (See, for example, Holliger et al. (1993) Proc. Natl. Acad. Sci. USA 90:6444-6448; Poljak et al. (1994) Structure 2:1121-1123). The antibody portions of the invention are described in further detail in U.S. Pat. Nos. 6,090,382; 6,258,562; and 6,509,015.

The term "recombinant human antibody" refers to all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (for example, a mouse) that is transgenic for human immunoglobulin genes (See, for example, Taylor et al. (1992) Nucl. Acids Res. 20:6287) or antibodies prepared, expressed, created or isolated by any other means that involves splicing of human immunoglobulin gene sequences to other DNA sequences. Such recombinant human antibodies have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559; Morrison (1985) Science 229:1202-1207; Oi et al. (1986) BioTechniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060, Queen et al. (1989) Proc. Natl. Acad. Sci. USA 86:10029-10033 (1989); U.S. Pat. No. 5,530,101; U.S. Pat. No. 5,585,089; U.S. Pat. No. 5,693,761; U.S. Pat. No. 5,693,762; WO 90/07861; and U.S. Pat. No. 5,225,539.

The term "dose" or "dosage" refers to an amount of a substance, such as a TNFα inhibitor, which is administered to a patient preferably using the wearable automatic injection device of the invention. In one embodiment, the dose comprises an effective amount, for example, including, but not limited to, 20 mg, 30 mg, 40 mg, 50 mg, 60 mg, 70 mg, 80 mg, 90 mg, 100 mg, 110 mg, 120 mg, 130 mg, 140 mg, 150 mg, and 160 mg, of the TNFα inhibitor adalimumab.

The term "dosing" refers to the administration of a substance (for example, an anti-TNFα antibody) to achieve a therapeutic objective (for example, treatment of rheumatoid arthritis).

The term "dosing regimen" describes a treatment schedule for a substance, such as a TNFα inhibitor, for example, a treatment schedule over a prolonged period of time and/or throughout the course of treatment, for example, administering a first dose of a TNFα inhibitor at week 0 followed by a second dose of a TNFα inhibitor on a biweekly dosing regimen.

The term "treatment" refers to therapeutic treatment, as well as prophylactic or suppressive measures, for the treatment of a disorder, such as a disorder in which TNFα is detrimental, for example, rheumatoid arthritis.

The term "patient" or "user" refers to any type of animal, human or non-human, that may receive an administration of a substance using exemplary automatic injection devices.

The terms "wearable automatic injection device" and "wearable autoinjector" refer to a device worn by a patient that enables the patient to self-administer a therapeutically effective dose of a therapeutic agent by either fastening the wearable device directly to his or her skin or fastening the wearable device to an article of clothing that allows the device to interface with the patient's body, wherein the wearable device differs from a conventional syringe by the inclusion of a mechanism for automatically administering the therapeutic agent to the patient's body when the mechanism is engaged.

The terms "syringe" and "cartridge" encompass a sterile barrel portion that is to filled with a dose of a therapeutic agent prior to distribution or sale to a patient or other non-medical professional for administration of the therapeutic agent to a patient. In an exemplary embodiment in which the barrel portion forms a syringe, a distal end of the barrel portion may be coupled to a sterile needle or multiple sterile needles. In another exemplary embodiment in which the barrel portion forms a cartridge, a distal end of the barrel portion may not be coupled to a sterile needle or multiple sterile needles. In some exemplary embodiments, a syringe may be a cartridge with a pre-attached needle or a plurality of needles coupled to its barrel portion.

Exemplary barrel portions of a syringe or cartridge may be formed of any suitable material including, but not limited to, a polymer material (e.g., a medical grade polymer), metal, glass, silicone crystals, and the like. In an exemplary embodiment, the barrel portion may be rigid or may take the form of one or more flexible pouches for holding the therapeutic agent.

Exemplary embodiments described herein with reference to a syringe assembly may also be implemented using a cartridge assembly. Similarly, exemplary embodiments described herein with reference to a cartridge assembly may also be implemented using a syringe assembly.

The term "vessel" refers to either a syringe or cartridge that may be used in an exemplary wearable automatic injection device for holding a dose of a therapeutic agent.

The term "biasing mechanism" refers to one or more components in an automatic injection device that directly or indirectly provide a force to a plunger and/or a bung. In an exemplary embodiment, the biasing mechanism may include one or more springs (e.g., a helical spring, a compression spring). The biasing mechanism may be in a retracted state before administration of a therapeutic agent and may be released during administration to actuate the bung forwardly within the barrel portion. In another exemplary embodiment, the biasing mechanism may include a chemical gas generator, for example, an expanding foam, that is in a non-expanded phase before administration of the therapeutic agent and that expands during administration to actuate the bung forwardly within the barrel portion. In other exemplary embodiments, the biasing mechanism may employ hydraulic pressure of working fluids, gas pressure of compressed gases, osmotic pressure, hydrogel expansion, and the like.

The term "administration" refers to any mechanism of delivering or administering a therapeutic agent to a patient's body. Exemplary mechanisms or techniques of administration include, but are not limited to, subcutaneous, intradermal, intramuscular, topical, and the like.

The term "administration site" refers to a location on or in a patient's body at or near which an exemplary automatic injection device may interface with the patient for administering a therapeutic agent.

The term "administration interface" refers to one or more components in a wearable automatic injection device that are inserted into, applied upon or that otherwise interface with a patient's body to administer a dose of a therapeutic agent to the patient.

In an exemplary embodiment, the administration interface may be directly coupled to or in contact with a syringe or a cartridge assembly that holds the dose of the therapeutic agent. In another exemplary embodiment, the administration interface may be indirectly coupled to the syringe or cartridge assembly, for example, via a piercing needle. In an exemplary embodiment, a transfer mechanism may provide fluid communication between the piercing needle and the administration interface. Exemplary administration interfaces may include, but are not limited to, a single needle, multiple needles, a needle coupled to a tubing, multiple needles coupled to a tubing, multiple microneedles including dissolvable microneedles, a needle-free pad, a needle-free patch, and the like.

The terms "microneedle" and "minineedle" refer to a miniature injection needle having any suitable dimension for the desired technique of administering a therapeutic agent to a patient. Exemplary microneedles may range in length from about one micron to about 5 mm, but are not limited to this exemplary range.

The terms "piercing needle" and "piercing needle" refer to one or more sharp components (e.g., one or more needles and/or one or more spikes) in a wearable automatic injection device that are coupled to or in contact with a syringe or a cartridge assembly for conveying a dose of a therapeutic agent from the syringe or cartridge assembly to an administration interface which, in turn, administers the therapeutic agent to a patient. In an exemplary embodiment, the piercing needle is not inserted into or applied to the patient. In another exemplary embodiment, the piercing needle may be inserted into or applied to the patient's body.

In an exemplary wearable automatic injection device including a syringe assembly, the piercing needle may be coupled directly to the barrel portion of the syringe and may be in fluid communication with the barrel portion. In an exemplary wearable automatic injection device including a cartridge assembly, the piercing needle may be provided separately from the barrel portion of the cartridge, for example, within an administration interface button or a transfer mechanism. During an administration stage, the piercing needle may be inserted into a distal end of the barrel portion of the cartridge to establish fluid communication between the piercing needle and the barrel portion.

The term "pre-administration state" refers to a state of a wearable automatic injection device prior to the start of administration of a therapeutic agent contained in the device.

The term "administration state" refers to one or more states of a wearable automatic injection device during the administration of a therapeutic agent contained in the device.

The term "post-administration state" refers to completion of administration of a therapeutically effective dose of a therapeutic agent contained in the device and to removal of the device from the patient prior to completion of administration of a therapeutically effective dose of the therapeutic agent.

The term "fast" refers to an administration rate of a volume of a therapeutic agent. In an exemplary embodiment, a volume of about 0.1 milliliters to about 1 milliliter or more of a therapeutic agent may be administered in an administration time period of about one second to about twelve hours. In an exemplary embodiment, the administration time period for the same range of volumes may range from about one second to about thirty seconds, but is not limited to this exemplary range. In certain exemplary embodiments, therapeutic agent volumes of about 0.1 milliliters to about 1 milliliter may be administered in a time duration ranging from about 3 seconds to about 5 seconds. In certain exemplary embodiments, therapeutic agent volumes of about 0.1 milliliters to about 1 milliliter may be administered in time durations of or shorter than about 20 seconds.

In certain exemplary embodiments, two or more automatic injection devices may be coupled or used simultaneously to administer larger volumes than 1 milliliter within time durations ranging from about one second to about thirty seconds.

In certain exemplary embodiments, two or more cartridges may be provided in an automatic injection device to simultaneously administer larger volumes than 1 milliliter within time durations ranging from about one second to about thirty seconds.

In certain exemplary embodiments, two or more syringes may be provided in an automatic injection device to simultaneously administer larger volumes than 1 milliliter within time durations ranging from about one second to about thirty seconds.

The term "clothing" refers to any suitable covering on a patient's skin to which an exemplary wearable automatic injection device may be coupled or attached. The article of clothing may thus form an intermediate layer between the device and the patient's skin and may be used to indirectly couple the device to the patient's skin. In an exemplary embodiment, the article of clothing may be snug clothing on the patient's skin, for example, nylon stockings. In another exemplary embodiment, the article of clothing may be a covering on the patient's skin including, but not limited to, a medical tape, a bandage, and the like. In another exemplary embodiment, the article of clothing may be a coupling mechanism that adheres the device in the proximity of the patient's skin including, but not limited to, a sleeve that may fit round a portion of the patient's body, a belt, a strap (e.g., a Velcro strap), and the like.

The term "proximal," as used herein, refers to a portion, end or component of an exemplary automatic injection device that is farthest from an injection site on a patient's body when the device is held against the patient for an injection or for mimicking an injection.

The term "distal," as used herein, refers to a portion, end or component of an exemplary automatic injection device that is closest to an injection site on a patient's body when the device is held against the patient for an injection or for mimicking an injection.

The term "equal" is used herein, in a broad lay sense, to mean exactly equal or approximately equal within some tolerance.

II. Exemplary Automatic Injection Devices

Certain exemplary wearable automatic injection devices are described with reference to FIGS. 1-14. Certain exemplary needle systems that may be used in exemplary wearable automatic injection devices to convey a therapeutic agent are described with reference to FIGS. 15-21. Certain exemplary plunger actuation systems and administration interface retraction systems that may be used in exemplary wearable automatic injection devices to expel a therapeutic agent from a syringe or cartridge are described with reference to FIGS. 22-31. Certain exemplary administration interface protection systems that may be used in exemplary wearable automatic injection devices to maintain an administration interface in a retracted position after administration in a post-administration state are described with reference to FIGS. 32-35.

Exemplary wearable automatic injection devices may employ a cartridge assembly (as illustrated in FIGS. 1A-1F) or a syringe assembly (as illustrated in FIGS. 2A-2F) for holding a dose of a therapeutic agent that may be administered to a patient through an administration interface. In some of FIGS. 1A-1F and 2A-2F, the administration interface is represented as a single injection needle. However, exemplary administration interfaces are not limited to the illustrative embodiments shown in FIGS. 1A-1F and 2A-2F.

Figure 1B:
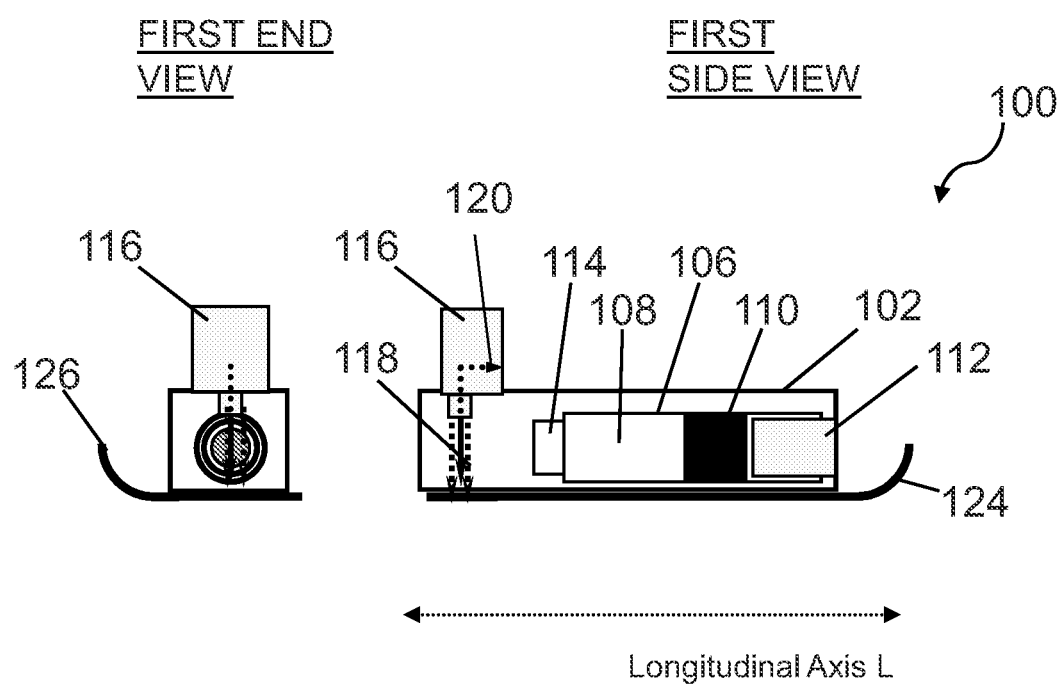
FIG. 1B illustrates the first end view and the first side view of the exemplary device of FIG. 1A in a pre-administration state before administration of a therapeutic agent in which a cover covering the administration interface is removed in preparation for an administration of the therapeutic agent.
Figure 1C:
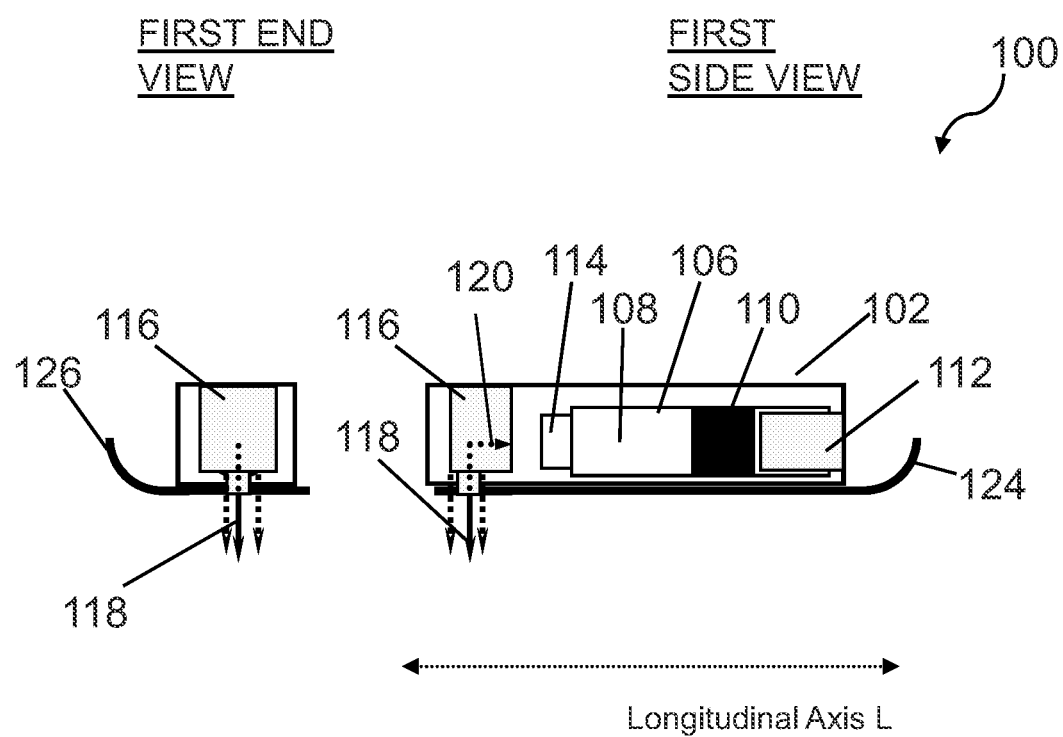
FIG. 1C illustrates the first end view and the first side view of the exemplary device of FIG. 1A in an administration state during administration of a therapeutic agent in which the administration interface interfaces with the patient's body.
Figure 1D:
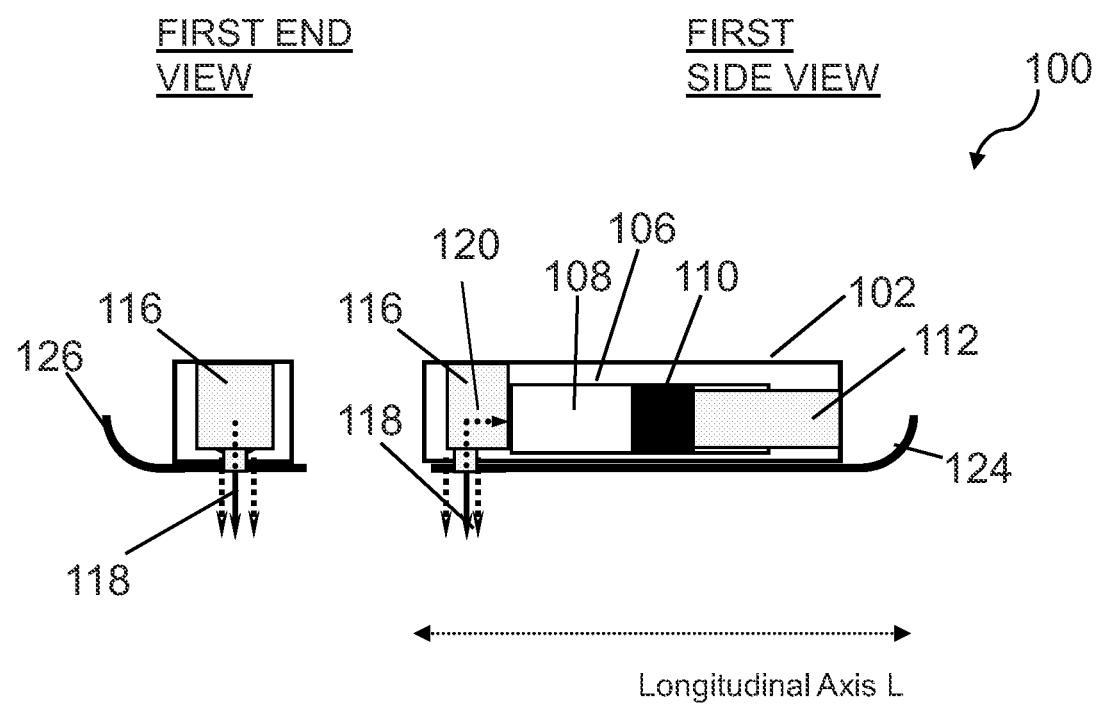
FIG. 1D illustrates the first end view and the first side view of the exemplary device of FIG. 1A in an administration state during administration of a therapeutic agent in which a barrel portion of the device containing a dose of the therapeutic agent is deployed forwardly within the housing of the device.
Figure 1E:
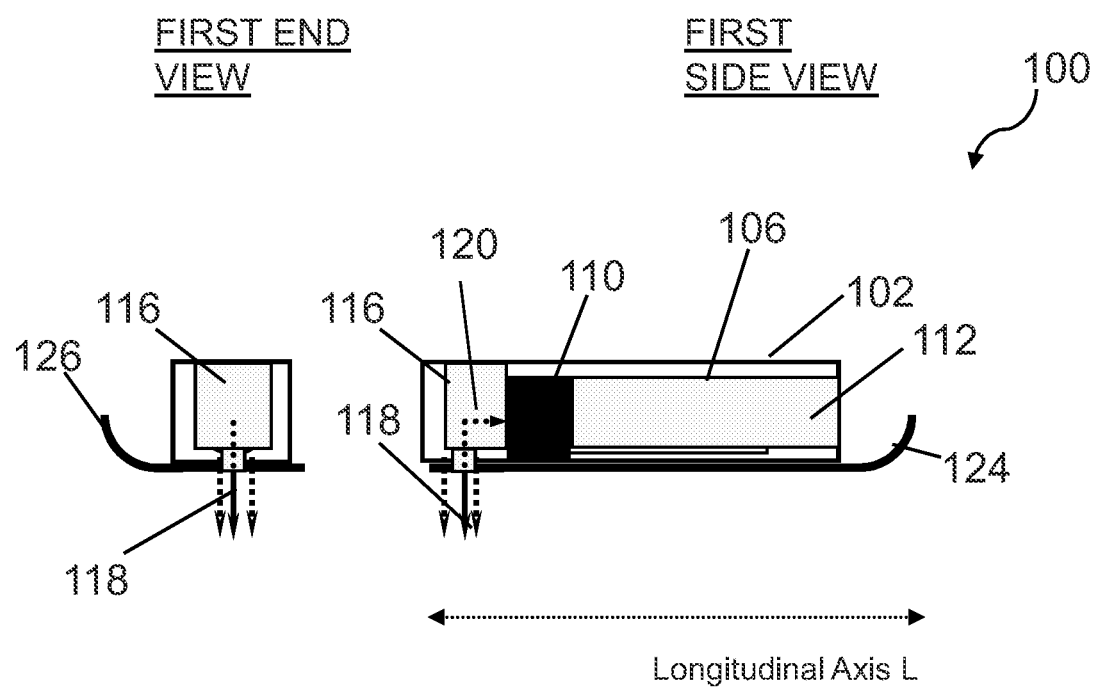
FIG. 1E illustrates the first end view and the first side view of the exemplary device of FIG. 1A in an administration state during administration of a therapeutic agent in which a bung of the device is actuated by a plunger actuator to expel the dose of the therapeutic agent from the barrel portion.
Figure 1F:
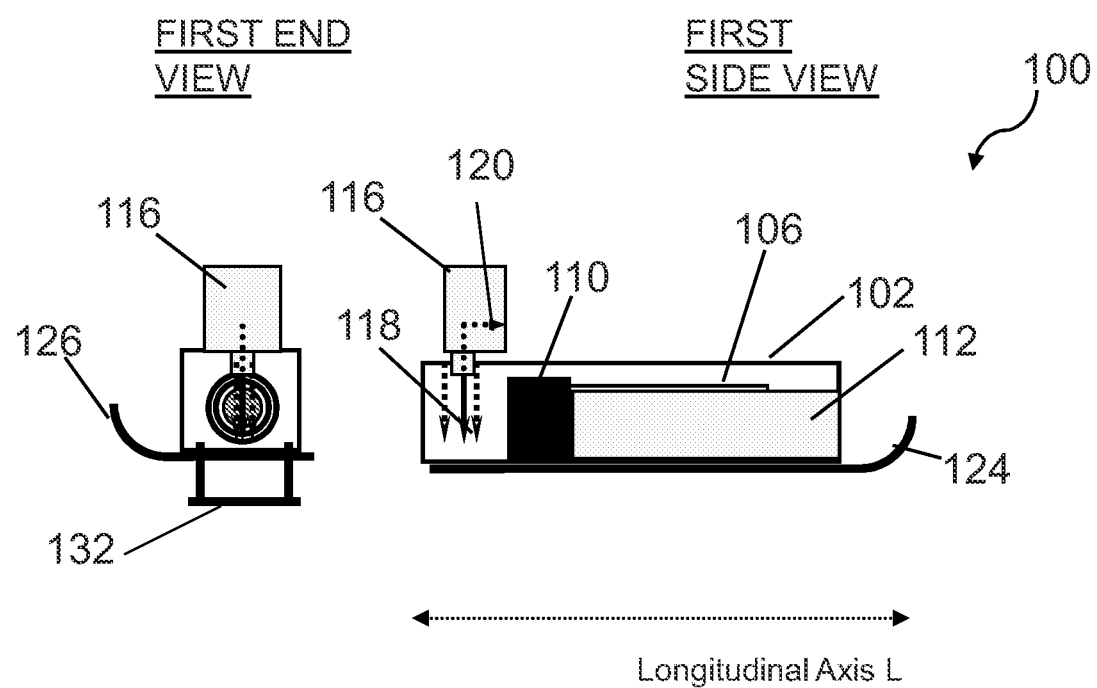
FIG. 1F illustrates the first end view and the first side view of the exemplary device of FIG. 1A in a post-administration state after administration of a therapeutic agent in which the administration interface is retracted within the housing of the device.

FIGS. 1A-1F illustrate an exemplary embodiment of a wearable automatic injection device 100 including a cartridge assembly that may be used to administer a dose of a therapeutic agent to a patient. FIG. 1A illustrates a first end view and a first side view of the exemplary wearable device 100 in a packaged pre-administration state. FIG. 1B illustrates the first end view and the first side view of the exemplary device 100 in a pre-administration state in which a cover covering the administration interface is removed in preparation for administering the dose to the patient. FIG. 1C illustrates the first end view and the first side view of the exemplary device 100 during administration in an administration state in which the administration interface protrudes from the housing of the device to interface with the patient's body. FIG. 1D illustrates the first end view and the first side view of the exemplary device 100 during administration in an administration state in which the barrel portion containing the dose of the therapeutic agent is deployed forwardly within the housing of the device 100. FIG. 1E illustrates the first end view and the first side view of the exemplary device 100 during administration in an administration state in which the bung is actuated by a plunger actuator to expel the dose of the therapeutic agent from the barrel portion. FIG. 1F illustrates the first end view and the first side view of the exemplary device 100 after administration in a post-administration state in which the administration interface is retracted within the housing of the device 100.

The wearable automatic injection device 100 may include a housing 102 that includes a plurality of walls to define an interior portion or cavity therein for accommodating a cartridge assembly. In an exemplary embodiment, one or more apertures or open ends may be provided at a side wall of the housing 102 and may be configured to receive an exemplary cartridge assembly. In an exemplary embodiment, during assembly of the automatic injection device, the cartridge assembly may be slid into the cavity of the housing 102 through the aperture or open end. In an exemplary embodiment, a cover portion may be provided for covering the aperture or open end.

In an exemplary embodiment, the housing 102 may have an elongated configuration, although one of ordinary skill in the art will recognize that the housing 102 may have any suitable size, shape and configuration for housing a barrel portion containing a dose of a therapeutic agent to be administered to a patient. In an exemplary embodiment, the housing 102 may be provided as a unitary cover coupled to a base that forms the patient contact portion. In an exemplary embodiment, the housing 102 may be formed of any suitable material including, but not limited to, plastic and other known materials.

The housing 102 of the wearable automatic injection device 100 may include an adhesive layer 124 disposed along a patient contact portion at the bottom of the housing 102 that is placed proximal to the skin of the patient or an article of clothing of the patient. In some exemplary embodiments, the adhesive layer 124 may be configured to be placed on the body of the patient in order to attach the housing 102 to the patient to administer the dose of the therapeutic agent. The adhesive layer 124 may include a non-adhesive removal mechanism 126, e.g., a tab, that is not adhesive. The non-adhesive removal mechanism 126 may be gripped by the patient and pulled to remove the wearable automatic injection device 100 from the skin or clothing of the patient.

Before the wearable automatic injection device 100 is put to use, for example, in the package state illustrated in FIG. 1A, the adhesive layer 124 may be covered by a protective film 128 which preserves the adhesive nature of the adhesive layer 124. The protective film 128 may include a removal mechanism 130 which may be gripped by the patient and pulled to remove the protective film 128 from the adhesive layer 124. This exposes the adhesive layer 124, allowing the patient to attach the housing 102 to his or her skin or article of clothing by placing the side with the adhesive layer 124 on the skin or the article of clothing.

The housing 102 may house a therapeutic agent cartridge assembly extending substantially along a longitudinal axis L between a proximal end (farthest from the administration interface) and a distal end (nearest to the administration interface). The cartridge assembly may include a barrel portion 106 for holding a dose 108 of a therapeutic agent to be administered to a patient. The barrel portion 106 may extend substantially along the longitudinal axis between a proximal end (farthest from the administration interface) and a distal end (nearest to the administration interface). In an exemplary embodiment, the barrel portion 106 may be a substantially cylindrical member having a circular cross-section, although one of ordinary skill in the art will recognize that the barrel portion 106 may have any suitable shape or configuration.

In an exemplary embodiment, the barrel portion 106 may be stationary within the housing 102 so that the administration process does not result in the movement of the barrel portion 106 within and relative to the housing 102. In another exemplary embodiment, the barrel portion 106 may initially, i.e., in a pre-administration state before administration of the therapeutic agent, be in a retracted position toward the proximal end of the device 100 (as illustrated in FIGS. 1A-1C), and may be actuated to an extended position toward the distal end of the device 100 in an administration state during administration of the therapeutic agent. A bung 110 may be provided at or near the proximal end of the barrel portion 106 to seal the dose of the therapeutic agent within the barrel portion 106 and to apply a force to the dose to expel the dose from the barrel portion 106. The bung 110 may be moveable within the barrel portion 106 toward the distal end of the barrel portion 106 in order to expel the dose from the barrel portion 106 in an administration state during administration of the therapeutic agent. In an exemplary embodiment, the bung 110 may be configured to perform both functions of sealing the dose and squeezing the dose out of the barrel portion 106. In another exemplary embodiment, a bung may be provided to seal the dose within the barrel portion 106 and a separate piston or plunger rod may be provided to impart a force to the bung in order to squeeze the dose out of the barrel portion 106.

The cartridge assembly may include, at or near its proximal end, a plunger actuator 112 for selectively actuating the bung 110 forwardly within the barrel portion 106 toward the distal end in order to administer the therapeutically effective dose contained in the barrel portion 106 to a patient. The plunger actuator 112 may employ an energy storage and controlled energy release mechanism to actuate the bung 110. In exemplary embodiments, the plunger actuator 112 may be located outside the barrel portion 106 or partly or fully within the barrel portion 106. In an exemplary embodiment, the plunger actuator 112 may drive the bung 110 directly or indirectly though the use of a plunger disposed between the bung 110 and the plunger actuator 112.

In an exemplary embodiment, the plunger actuator 112 may include a biasing mechanism, for example, a spring, that is retracted before administration and that is released during administration to actuate the bung 110 forwardly within the barrel portion 106. In another exemplary embodiment, the plunger actuator 112 may include a chemical gas generator, for example, an expanding foam, that is in a non-expanded phase before administration and that expands during administration to actuate the bung 110 forwardly within the barrel portion 106. In other exemplary embodiments, the plunger actuator 112 may employ hydraulic pressure of working fluids, gas pressure of compressed gases, osmotic pressure, hydrogel expansion, and the like.

In an exemplary embodiment, the plunger actuator 112 may be moved forwardly within the barrel portion 106 in a substantially linear manner, i.e., substantially constant speed. This may allow the dose to be administered to the patient at a substantially constant administration rate. The plunger actuator 112 may include or may be coupled to a damping mechanism that may be used to absorb energy, for example, an initial release of energy, and to provide a more controlled release of energy during energy release by the plunger actuator 112. The controlled release of energy may result in a substantially linear administration profile, i.e., a substantially constant rate of administration of the dose over time, and may prevent abrupt changes in the speed of the administration.

In an exemplary embodiment, a plunger actuator 112 may employ one or more fluid circuits containing a working fluid in which the hydraulic pressure of the working fluid applies a force to the bung to move the bung within the barrel portion of the cartridge. A damping mechanism may employ a flow restrictor placed in the fluid circuit between a source of the working fluid and the bung.

In another exemplary embodiment, a plunger actuator 112 may employ a biasing mechanism, for example, a spiral spring or a helical compression spring. A damping mechanism may employ a viscous damper, a swiss lever escapement, a runaway escapement, and the like.

In another exemplary embodiment, a plunger actuator 112 may employ a stepper motor connected to a gear drive system to provide a constant linear administration profile.

The cartridge assembly may include, at or near its distal end, a cartridge stopper 114 that may include a septum and a cover 115 for the septum. The septum may be a pierceable layer of material that is disposed adjacent to the distal end of the barrel portion 106 in order to seal the dose in the barrel portion 106. When intact, the septum may seal the dose within the barrel portion 106. When pierced by a sharp component, for example, a piercing needle, the septum may allow the dose to leave the barrel portion 106 and enter the piercing needle. The septum may be formed of a material that may be pierced by a piercing needle. A cover may be provided to protectively cover the septum from accidental piercing by the piercing needle when the device 100 is in the packaged pre-administration state as illustrated in FIG. 1A. In an exemplary embodiment, the cartridge stopper 114 may also include a cover to protectively cover a piercing needle provided in the vicinity of the cartridge stopper 114, thereby preventing accidental piercing of the septum by the piercing needle when the device 100 is in the packaged pre-administration state as illustrated in FIG. 1A.

The housing 102 of the wearable automatic injection device 100 may also house an administration interface button 116 bearing an administration interface 118 that is configured to pierce the patient's skin. In an exemplary embodiment, the administration interface 118 may be aligned orthogonally to the longitudinal axis L of the device 100. In an exemplary embodiment, the administration interface 118 may be held in place by an administration interface carrier (not pictured) provided in the administration interface button 116 or separately from the administration interface button 116.

In some exemplary embodiments, the administration interface 118 may include one or more injection needles having any suitable size, shape and configuration suitable for piercing the skin of the patient to administer a therapeutic agent. In an exemplary embodiment, the administration interface 118 may include a single injection needle (shown as a continuous line in FIGS. 1A-1F). In another exemplary embodiment, the administration interface 218 may include two or more injection needles (the additional needles shown as dashed lines in FIGS. 1A-1F). In some other exemplary embodiments, the administration interface 118 may include a needle-free pad and/or a needle-free patch for performing a topical administration of a therapeutic agent.

Suitable injection needles that may be used in exemplary administration interfaces may have a length configured or selected to provide an administration depth suitable for the desired therapy. Subcutaneous injections typically penetrate about six to ten millimeters into the skin. In an exemplary embodiment, exemplary injection needles may have a length of about twelve mm and may be administered to a depth of about seven mm into the skin. In other exemplary embodiments, exemplary injection needles may have lengths suitable for intradermal, intramuscular therapies, and the like. Suitable injection needles may have a wall thickness suitable to provide sufficient mechanism strength, a diameter suitable to allow a desired flow rate of the substance while minimizing patient sensation, and a tip geometry suitable for the desired therapy while minimizing patient sensation.

Exemplary injection needles may be coated as needed to minimize patient sensation as allowed by therapy. The administration interface 118 may be covered, protected from mechanical damage and maintained in a sterile or septic condition by an administration interface cover 122, for example, a rigid needle shield, a soft needle shield, or both. The administration interface cover 122 may also maintain sterility of the fluid conduit formed by and coupled to the administration interface 118.

The administration interface button 116 may also bear a piercing needle 120 configured to pierce the septum and establish fluid communication with the barrel portion 106. In an exemplary embodiment, the piercing needle 120 may be aligned parallel to the longitudinal axis L of the device 100. The piercing needle 120 may have any suitable size, shape and configuration suitable for piercing the septum and is not limited to the illustrative embodiment.

In an exemplary embodiment, the administration interface 118 and the piercing needle 120 may be coupled to and in fluid communication with each other via the body of the administration interface button 116. In another exemplary embodiment, the administration interface 118 and the piercing needle 120 may be coupled to and in fluid communication with each other via one or more fluid conduits (not pictured). In another exemplary embodiment, the administration interface 118 and the piercing needle 120 may be directly coupled to and in fluid communication with each other.

In an exemplary embodiment, in a pre-administration state before administration of the therapeutic agent, the administration interface button 116 may be in a vertically raised position relative to the housing 102 such that the administration interface button 116 protrudes from the top of the housing 102, as illustrated in FIGS. 1A and 1B. In this position, the administration interface 118 may be retracted within the housing 102 and may not be applied to the patient's body. In this position, the piercing needle 120 may be aligned vertically above the septum in the cartridge stopper 114 and may not pierce the septum. At the beginning of the administration process, the administration interface button 116 may be pressed downward, for example, by a user of the device or automatically. This may push the administration interface button 116 to a vertically depressed position relative to the housing 102 closer to the patient's body such that the administration interface button 116 no longer protrudes from the top of the housing 102, as illustrated in FIGS. 1C-1E. In this position, the administration interface 118 may protrude from the bottom of the housing 102 and may be inserted into or applied to the patient's body. In this position, the piercing needle 120 may be aligned with the septum in the cartridge stopper 114 and may pierce the septum.

In an exemplary embodiment, the septum may initially be spaced from the administration interface button 116. In this embodiment, the piercing needle 120 may pierce the septum when the cartridge stopper 114 bearing the septum is advanced within the housing 102 toward the administration interface button 116. That is, in a pre-administration state before administration of the therapeutic agent, the piercing needle 120 may be spaced from the septum such that there is no fluid communication between the barrel portion 106 and the administration interface 118 coupled to the administration interface button 116. In an administration state, the barrel portion 106 may advance within the housing 102 toward the distal end of the device 100 so that the piercing needle 120 may pierce the septum and establish fluid communication between the barrel portion 106 and the administration interface 118 coupled to the administration interface button 116. This fluid communication may allow the dose of the therapeutic agent to flow from the barrel portion 106 to the patient through the piercing needle 120 and the administration interface 118 when pressure is applied to the dose by the bung 110 in an administration state during administration of the therapeutic agent.

Referring now to FIG. 1F, in an exemplary embodiment, the housing 102 of the wearable automatic injection device 100 may include a skin sensor foot 132, which is a structure housed under or in the portion of the housing 102 proximal to the administration site on or in the patient's body. Prior to and during administration of the therapeutic agent, the skin sensor foot 132 is retained within or forms a portion of the underside of the housing 102. When the wearable automatic injection device 100 is attached to the administration site on or in the patient's body and activated, the skin sensor foot 132 may be free to move but may be constrained by the administration site. When the wearable automatic injection device 100 is removed from the administration site, regardless of whether the administration of the therapeutic agent was completed, the skin sensor foot 132 is no longer constrained, and extends and projects outside the periphery of the housing 102. This, in turn, activates a retraction trigger. When the retraction trigger is activated, a retraction mechanism retracts the administration interface 120 which may also raise the administration interface button 116 from the vertically lowered position to the vertically raised position, so that the administration interface button 116 protrudes from the top of the housing 102 and the administration interface 118 is retracted within the housing 102.

FIG. 1A illustrates the wearable automatic injection device 100 in a pre-administration state, for example, as packaged, in which the barrel portion 106 may be pre-filled and/or pre-fillable with the dose 108 of the therapeutic agent and in a retracted position ready for use. The barrel portion 106 may contain the dose 108 of the therapeutic agent in the interior space defined between the wall or walls of the barrel portion 106 and the bung 110. In an embodiment, the plunger actuator 112 may store energy that, when released, may actuate the bung 110. The administration interface button 116 may be partially disposed within the housing 102 at the vertically raised position above the administration site, and the administration interface 118 may be retracted within the housing 102. The protrusion of the administration interface button 116 out of the top of the housing 102 may provide a visual indication to the patient that the wearable automatic injection device 100 is not in operation.

FIG. 1B illustrates the wearable automatic injection device 100 in a pre-administration state in which the administration interface cover 122 and the septum cover are removed. In exemplary embodiments, the protective film 128 may include a linking member that is connected to the administration interface cover 122 and the septum and piercing needle covers in the cartridge stopper 114. The linking member may include a tether, a tab or other linkage mechanism. When the protective film 128 is removed, the linking member of the protective film 128 may remove the administration interface cover 122 and the septum and piercing needle covers in the cartridge stopper 114.

FIG. 1C illustrates the wearable automatic injection device 100 in an administration state during administration of the therapeutic agent in which the administration interface button 116 is in the vertically lowered position within the housing 102. In the vertically lowered position, the administration interface button 116 may be disposed within the housing 102 at a depressed or vertically lowered location above the administration site, and the administration interface 118 may project from the housing 102 through one or more apertures or open ends in the housing 102 so that it can interface with the patient's body at the administration site. In an exemplary embodiment, a cover portion may be provided for covering the aperture or open end. In an exemplary embodiment, the aperture or open end of the housing may oppose the patient contact portion of the housing such that the administration interface button 116 may be vertically lowered to administer the therapeutic agent. In the vertically lowered state, the administration interface button 116 may not protrude from the top of the housing 102, which may provide a visual indication to the patient that the wearable automatic injection device 100 is in operation. In another exemplary embodiment, the aperture or open end in the housing 102 may not be disposed opposing the patient contact portion and may instead be disposed in a side wall of the housing. The administration interface button 116 may be moved laterally or horizontally in some exemplary embodiments to administer the therapeutic agent.

FIG. 1D illustrates the wearable automatic injection device 100 in an administration state during administration of the therapeutic agent in which the barrel portion 106 containing the dose 108 of the therapeutic agent is deployed forwardly from a retracted position to an extended position within the housing of the device 100. The advancement of the barrel portion 106 may bring the distal end of the barrel portion 106 or the cartridge stopper 114 in the vicinity of or in contact with the administration interface button 116. In an exemplary embodiment, the piercing needle 120 may pierce the septum held in the cartridge stopper 114 in order to establish fluid communication between the barrel portion 106 and the administration interface 118.

FIG. 1E illustrates the wearable automatic injection device 100 in an administration state during administration of the therapeutic agent in which the plunger actuator 112 is triggered to move the bung 110. Triggering of the plunger actuator 112 may release stored energy in the plunger actuator 112 in order to move the bung 110 within the barrel portion 106 toward the distal end of the device 100. The movement of the bung 110 may eject the dose of the therapeutic agent from the barrel portion 106 through the distal end of the barrel portion 106. Any suitable mechanism may be used to trigger the plunger actuator 112 including, but not limited to, a linking member that is coupled to and activated by the depression of the administration interface button 116 or by the removal of the administration interface cover 122, a trigger button that may be activated by the patient, and the like.

FIG. 1F illustrates the wearable automatic injection device 100 in a post-administration state, for example, after administering a therapeutically effective dose of the therapeutic agent or removal of the wearable automatic injection device 100 from the patient before administration of a therapeutically effective dose of the therapeutic agent, in which the administration interface button 116 is in the vertically raised position. In the vertically raised position, the administration interface button 116 may be disposed partly within the housing 102 at an elevated or vertically raised location above the administration site, and the administration interface 118 may be retracted within the housing 102. A portion of the administration interface button 116 may project from the top of the housing 102 to provide a visual indication to the patient that the wearable automatic injection device assembly 100 is not in operation (i.e., in a post-administration state). The barrel portion 106 may be empty of the therapeutic agent and the plunger actuator 112 may no longer store energy. A skin sensor foot 132 may extend from the bottom of the housing 102 upon removal of the device 100 from the administration site.

The housing 102 may include a retraction mechanism that automatically raises the administration interface button 116 from the vertically lowered administration state (shown in FIGS. 1C-1E) to the vertically raised post-administration state (shown in FIG. 1F). In an exemplary embodiment, the retraction mechanism may include a biasing mechanism, for example, a spring, that biases the cartridge assembly away from the administration site when the retraction mechanism is triggered.

A retraction trigger, when activated, may trigger the retraction mechanism in order to raise the administration interface button 116 from the vertically lowered state to the vertically raised state. In an exemplary embodiment, the bung 110 and/or the plunger actuator 112 may include a linking member connected to the retraction trigger. The linking member may include a tether, a tab or other linkage mechanism. The linking member may be of a suitable length such that, when the bung 110 has been moved to the end of the barrel portion 106 (in order to administer a dose of the therapeutic agent), the linking member triggers a latch that in turn activates the retraction trigger. In another exemplary embodiment, the extension of the skin sensor foot 132 from the bottom of the housing 102 may activate the retraction trigger.

In an exemplary embodiment, the retraction mechanism may include an end-of-dose retraction trigger that, when activated, triggers the retraction mechanism. The end-of-dose retraction trigger may be activated when the therapeutically effective dose of therapeutic agent in the wearable automatic injection device 100 is administered. In an exemplary embodiment, the end-of-dose retraction trigger may include a latch, for example, a flexible plastic hook, that is released upon completed administration of the therapeutic agent. The retraction mechanism may also include an early-removal retraction trigger that, when activated, triggers the retraction mechanism. The early-removal retraction trigger may be activated when the wearable automatic injection device 100 is removed from the administration site before the therapeutically effective dose of therapeutic agent is completely administered. In an exemplary embodiment, the early-removal retraction trigger may include a latch, for example, a flexible plastic hook, that is released upon removal of the wearable automatic injection device 100 from the administration site. The retraction mechanism is responsive to the end-of-dose retraction trigger and responsive to the early-removal retraction trigger to automatically retract the cartridge assembly from the administration site.

In an exemplary embodiment, raising of the administration interface button 116 to the vertically raised position may cause the piercing needle 120 to bend upward, thus preventing undesirable reuse of the piercing needle and the wearable automatic injection device.

Figure 2A:
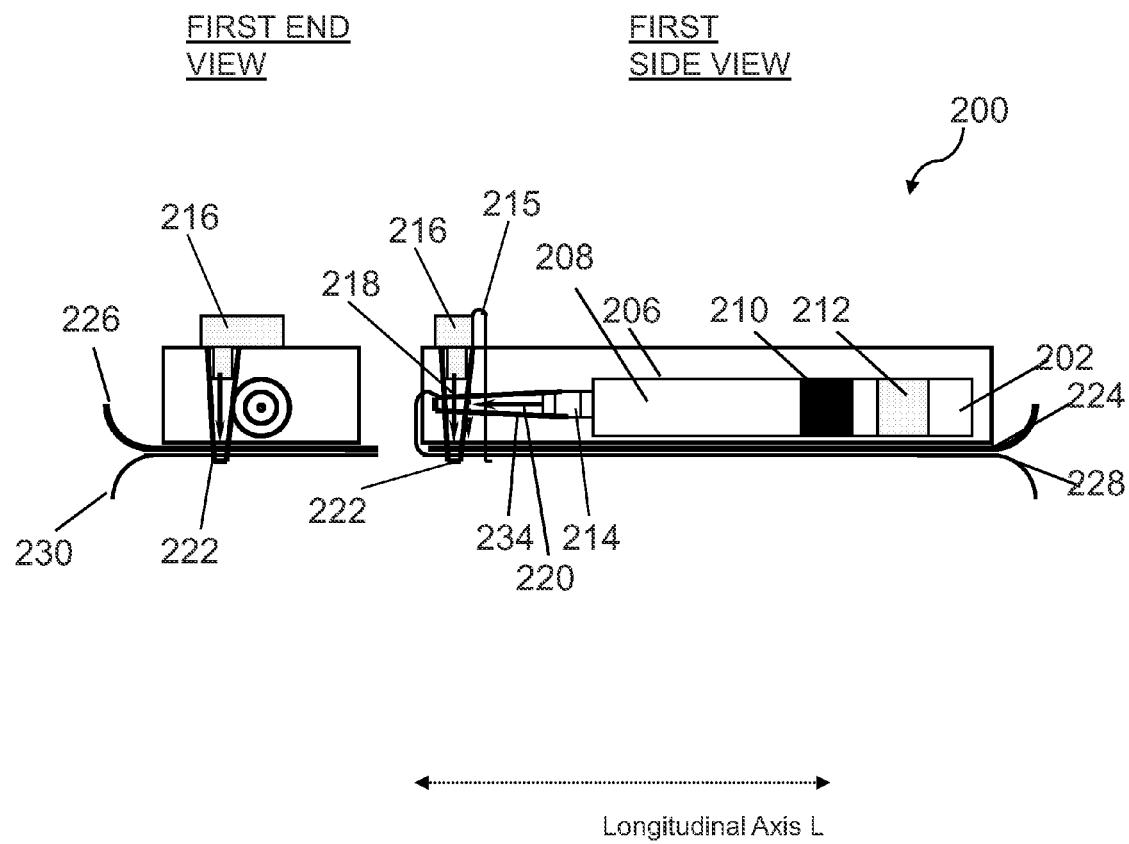
FIG. 2A illustrates a first end view and a first side view of an exemplary wearable device including a syringe assembly in a packaged pre-administration state.
Figure 2B:
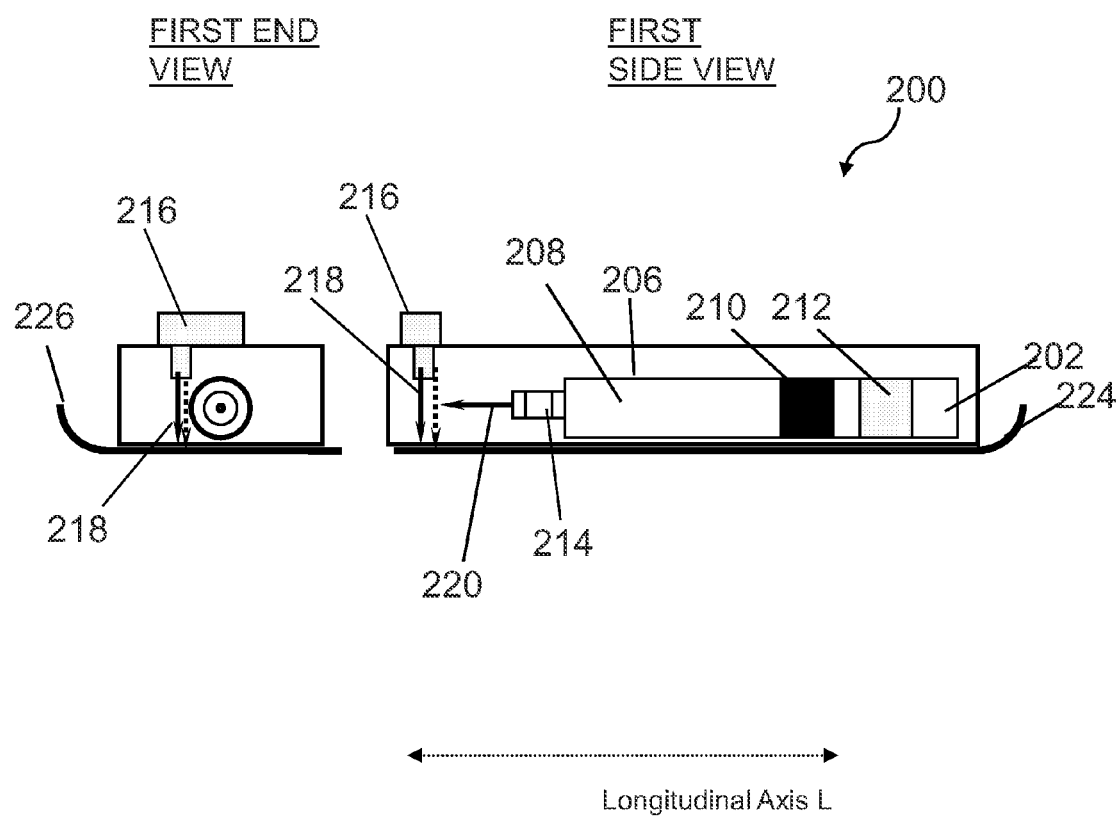
FIG. 2B illustrates the first end view and the first side view of the exemplary device of FIG. 2A in a pre-administration state before administration of a therapeutic agent in which a cover covering the administration interface is removed in preparation for administration of the therapeutic agent.
Figure 2C:
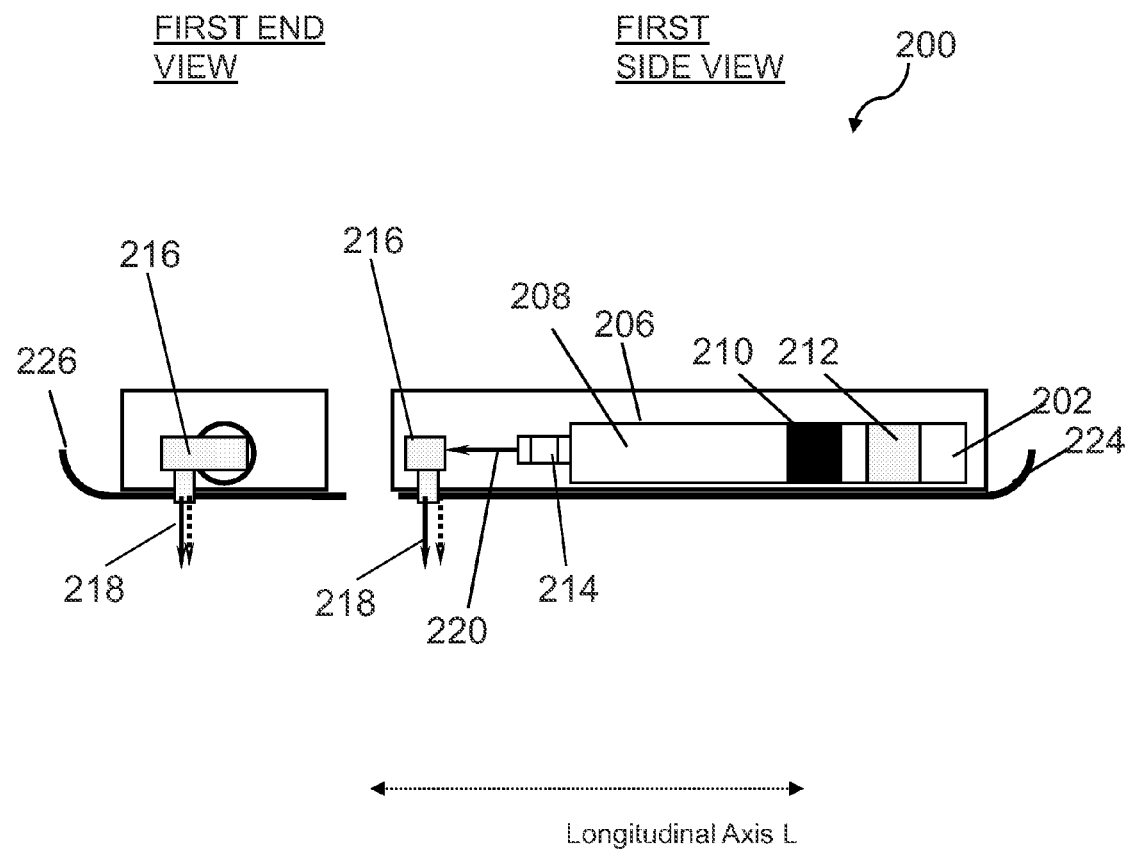
FIG. 2C illustrates the first end view and the first side view of the exemplary device of FIG. 2A in an administration state during administration of a therapeutic agent in which the administration interface interfaces with the patient's body.
Figure 2D:
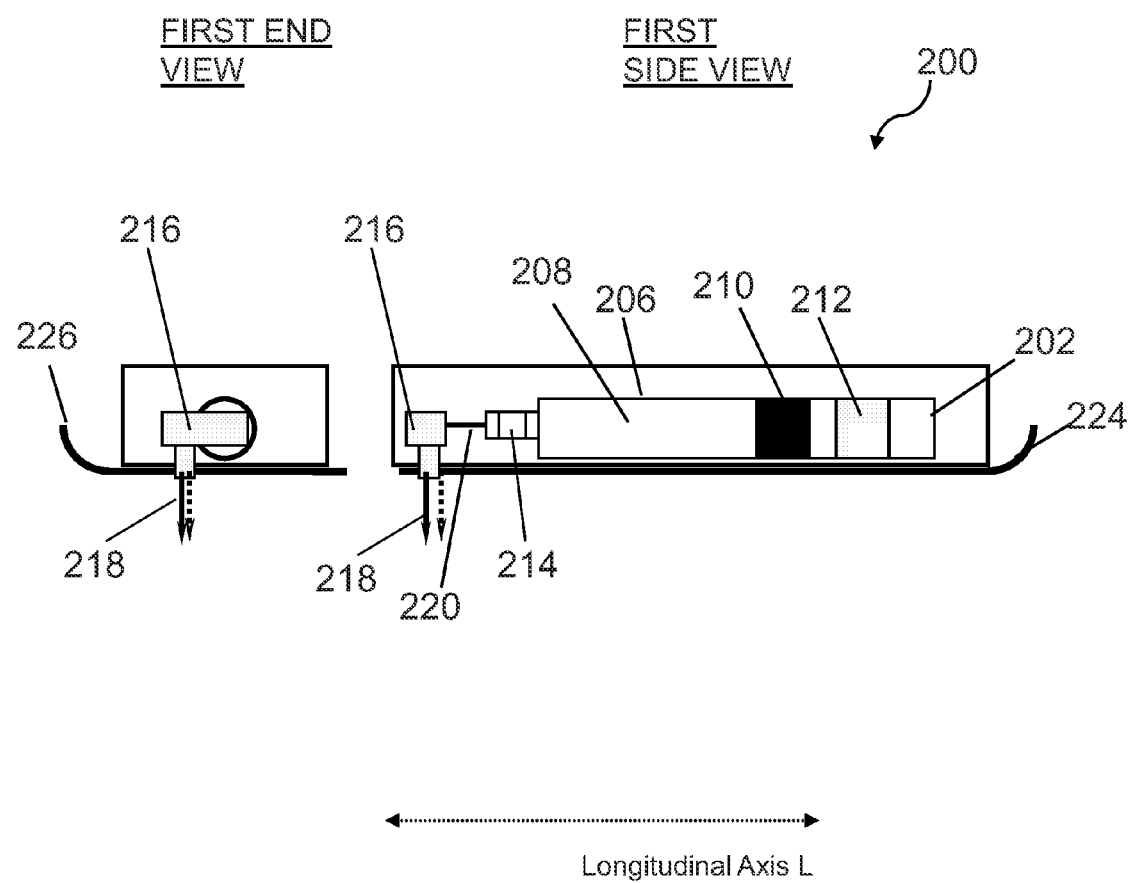
FIG. 2D illustrates the first end view and the first side view of the exemplary device of FIG. 2A in an administration state during administration of a therapeutic agent in which a barrel portion of the device containing a dose of the therapeutic agent is deployed forwardly within the housing of the device.
Figure 2E:
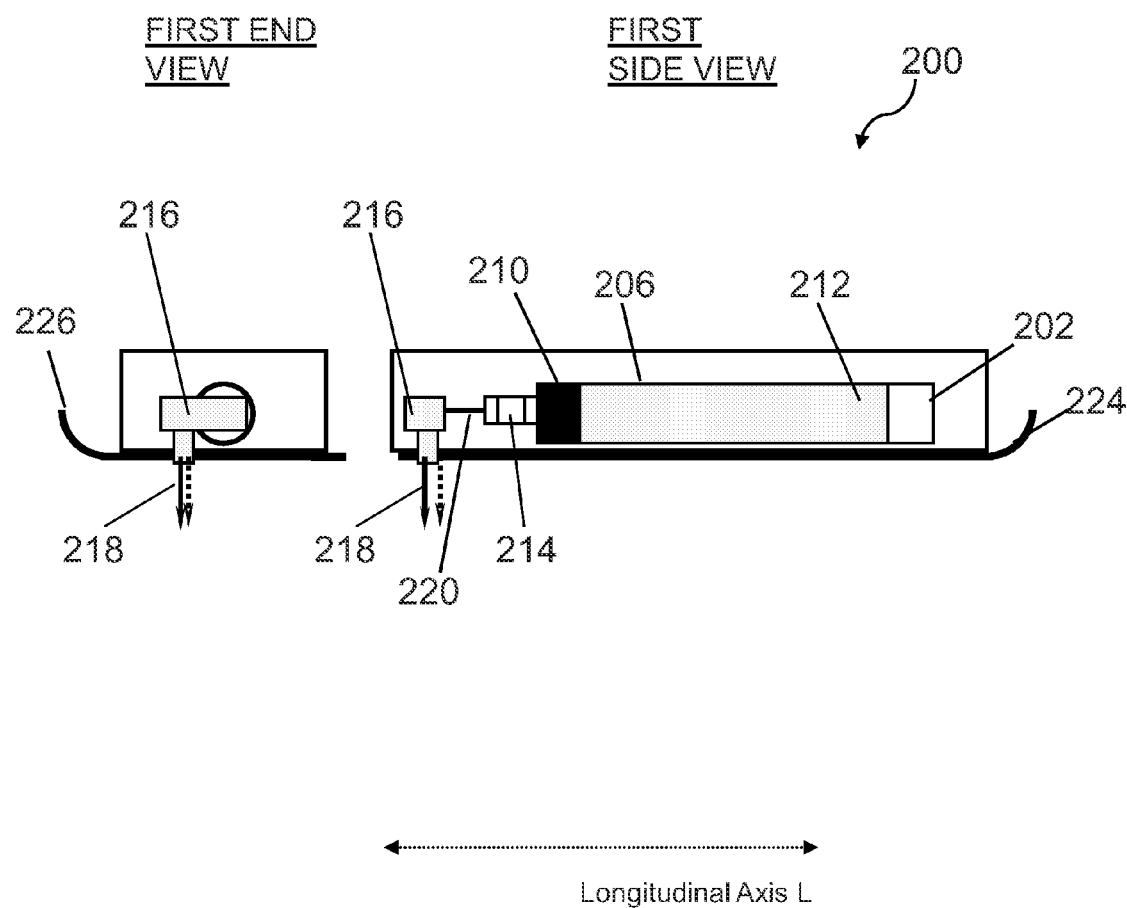
FIG. 2E illustrates the first end view and the first side view of the exemplary device of FIG. 2A in an administration state during administration of a therapeutic agent in which a bung of the device is actuated by a plunger actuator to expel the dose of the therapeutic agent from the barrel portion.
Figure 2F:
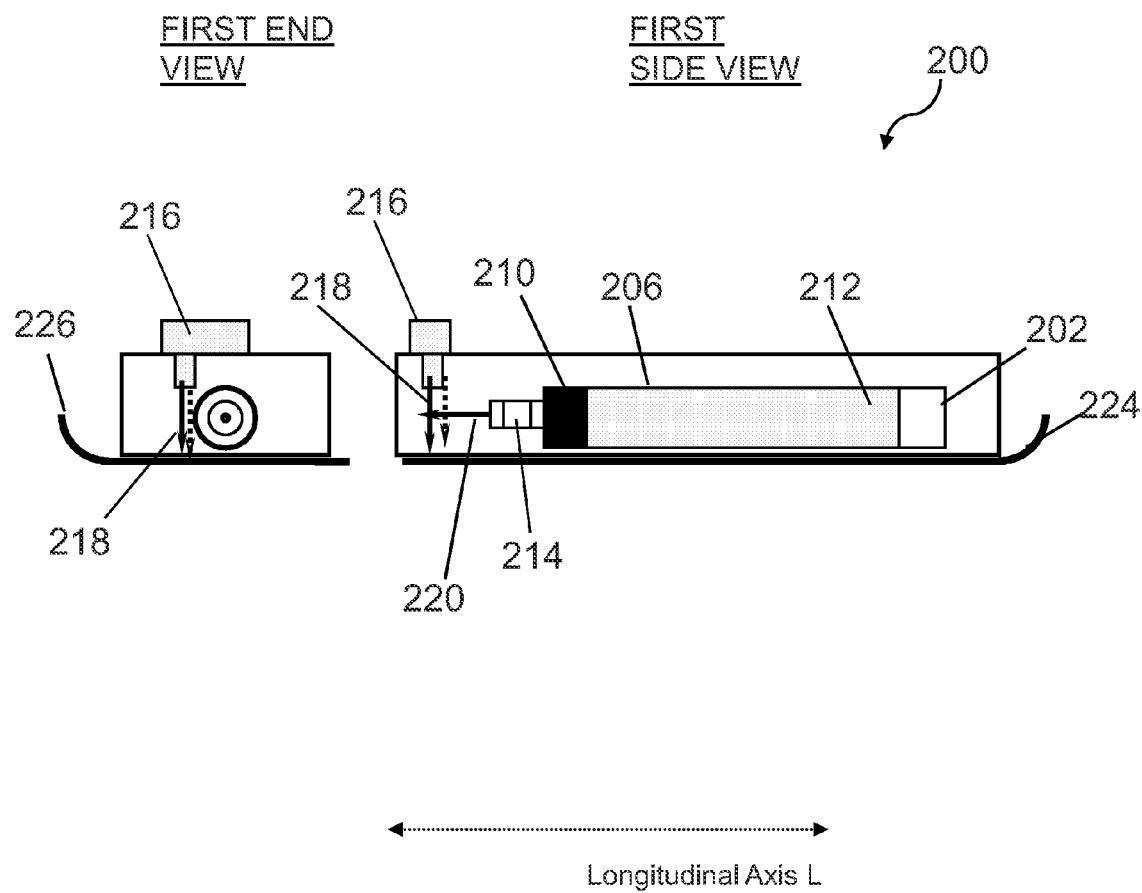
FIG. 2F illustrates the first end view and the first side view of the exemplary device of FIG. 2A in a post-administration state after administration of a therapeutic agent in which the administration interface is retracted within the housing of the device.

FIGS. 2A-2F illustrate an exemplary embodiment of a wearable automatic injection device 200 including a syringe assembly that may be used to administer a dose of a therapeutic agent to a patient. FIG. 2A illustrates a first end view and a first side view of the exemplary wearable device 200 in a packaged pre-administration state. FIG. 2B illustrates the first end view and the first side view of the exemplary device 200 in a pre-administration state in which a cover covering the administration interface is removed in preparation for administration a therapeutic agent. FIG. 2C illustrates the first end view and the first side view of the exemplary device 200 in an administration state during administration of the therapeutic agent in which the administration interface protrudes from the housing of the device to interface with the patient's body FIG. 2D illustrates the first end view and the first side view of the exemplary device 200 in an administration state during administration of the therapeutic agent in which the barrel portion containing the dose of the therapeutic agent is deployed forwardly within the housing of the device 200. FIG. 2E illustrates the first end view and the first side view of the exemplary device 200 in an administration state during administration of the therapeutic agent in which the bung is actuated by a plunger actuator to expel the dose of the therapeutic agent from the barrel portion. FIG. 2F illustrates the first end view and the first side view of the exemplary device 200 in an post-administration state after administration of the therapeutic agent in which the administration interface is retracted within the housing of the device 200.

The wearable automatic injection device 200 may include a housing 202 for accommodating an exemplary syringe assembly. The wearable automatic injection device 200 may include a housing 202 that includes a plurality of walls to define an interior portion or cavity therein for accommodating a syringe assembly. In an exemplary embodiment, one or more apertures or open ends may be provided at a side wall of the housing 202 and may be configured to receive an exemplary syringe assembly. In an exemplary embodiment, during assembly of the automatic injection device, the syringe assembly may be slid into the cavity of the housing 202 through the aperture or open end. In an exemplary embodiment, a cover portion may be provided for covering the aperture or open end.

In an exemplary embodiment, the housing 202 may have an elongated configuration, although one of ordinary skill in the art will recognize that the housing 202 may have any suitable size, shape and configuration for housing a barrel portion containing a dose of a therapeutic agent to be administered to a patient. In an exemplary embodiment, the housing 202 may be provided as a unitary cover coupled to a base that forms the patient contact portion. In an exemplary embodiment, the housing 202 may be formed of any suitable material including, but not limited to, plastic and other known materials.

The housing 202 of the wearable automatic injection device 200 may include an adhesive layer 224 disposed along a patient contact portion at the bottom of the housing 202 that is placed proximal to the skin of the patient or an article of clothing of the patient. In some exemplary embodiments, the adhesive layer 224 may be configured to be placed on the skin of the patient in order to attach the housing 202 to the patient to administer the dose of the therapeutic agent. The adhesive layer 224 may include a non-adhesive removal mechanism 226, e.g., a tab, that is not adhesive. The non-adhesive removal mechanism 226 may be gripped by the patient and pulled to remove the wearable automatic injection device 200 from the skin or clothing of the patient.

Before the wearable automatic injection device 200 is put to use, for example, in the package state illustrated in FIG. 2A, the adhesive layer 224 may be covered by a protective film 228 which preserves the adhesive nature of the adhesive layer 224. The protective film 228 may include a removal mechanism 230, e.g., a tab, which may be gripped by the patient and pulled to remove the protective film 228 from the adhesive layer 224. This exposes the adhesive layer 224, allowing the patient to attach the housing 202 to his or her skin or article of clothing by placing the side with the adhesive layer 224 on the skin or the article of clothing.

The housing 202 may house a syringe assembly extending substantially along a longitudinal axis L between a proximal end (farthest from the administration interface) and a distal end (nearest to the administration interface). The syringe assembly may include a barrel portion 206 for holding a dose 208 of a therapeutic agent to be administered to a patient. The barrel portion 206 may extend substantially along the longitudinal axis between a proximal end (farthest from the administration interface) and a distal end (nearest to the administration interface). In an exemplary embodiment, the barrel portion 206 may be a substantially cylindrical member having a circular cross-section, although one of ordinary skill in the art will recognize that the barrel portion 206 may have any suitable shape or configuration.

In an exemplary embodiment, the barrel portion 206 may be stationary within the housing 202 so that the administration process does not result in the movement of the barrel portion 206 within and relative to the housing 202. In another exemplary embodiment, the barrel portion 206 may initially, i.e., in a pre-administration state before administration of the therapeutic agent, be in a retracted position toward the proximal end of the device 200 (as illustrated in FIGS. 2A-2C), and may be actuated to an extended position toward the distal end of the device 200 in an administration state during administration of the therapeutic agent.

A bung 210 may be provided at or near the proximal end of the barrel portion 206 to seal the dose of the therapeutic agent within the barrel portion 206 and to apply a force to the dose to expel the dose from the barrel portion 206. The bung 210 may be moveable within the barrel portion 206 toward the distal end of the barrel portion 206 in order to expel the dose from the barrel portion 206 in an administration state during administration of the therapeutic agent. In an exemplary embodiment, the bung 210 may be configured to perform both functions of sealing the dose and squeezing the dose out of the barrel portion 206. In another exemplary embodiment, a bung may be provided to seal the dose within the barrel portion 206 and a separate piston may be provided to impart a force to the bung in order to squeeze the dose out of the barrel portion 206.

The syringe assembly may include, at or near its distal end, a syringe stopper or a distal portion of the syringe 214 that may include a piercing needle 220. The piercing needle 220 may be covered, protected from mechanical damage and maintained in aseptic condition, i.e., sterile condition, by a piercing needle cover 234, for example, a soft needle shield, a rigid needle shield, or both. The piercing needle cover 234 may also maintain sterility of the fluid conduit formed by and coupled to the piercing needle 220. In an exemplary embodiment, the piercing needle 220 may be aligned parallel to the longitudinal axis L of the device 200. The piercing needle 220 may have any suitable size, shape and configuration suitable for piercing the septum, and is not limited to the illustrative embodiment.

The syringe assembly may include, at or near its proximal end, a plunger actuator 212 for selectively actuating the bung 210 forwardly within the barrel portion 206 toward the distal end in order to administer the therapeutically effective dose contained in the barrel portion 206 to a patient. The plunger actuator 212 may employ an energy storage and controlled energy release mechanism to actuate the bung 210. In exemplary embodiments, the plunger actuator 212 may be located outside the barrel portion 206 or partly or fully within the barrel portion 206. In exemplary embodiments, the plunger actuator 212 may drive the bung 210 directly or indirectly though the use of a plunger disposed between the bung 210 and the plunger actuator 212.

In an exemplary embodiment, the plunger actuator 212 may include a biasing mechanism, for example, a spring, that is retracted before administration of the therapeutic agent and that is released during administration to actuate the bung 210 forwardly within the barrel portion 206. In another exemplary embodiment, the plunger actuator 212 may include a chemical gas generator, for example, an expanding foam, that is in a non-expanded phase before administration of the therapeutic agent and that expands during administration to actuate the bung 210 forwardly within the barrel portion 206. In other exemplary embodiments, the plunger actuator 212 may employ hydraulic pressure of working fluids, gas pressure of compressed gases, osmotic pressure, hydrogel expansion, and the like.

In an exemplary embodiment, the plunger actuator 212 may be moved forwardly within the barrel portion 206 in a substantially linear manner, i.e., substantially constant speed. This may allow the dose to be administered to the patient at a substantially constant administration rate. The plunger actuator 212 may include or may be coupled to a damping mechanism that may be used to absorb energy, for example, an initial release of energy, and to provide a more controlled release of energy during energy release by the plunger actuator 212. The controlled release of energy may result in a substantially linear administration profile, i.e., a substantially constant rate of administration of the dose over time, and may prevent abrupt changes in the speed of the administration. In an exemplary embodiment, a plunger actuator 212 may employ the hydraulic pressure of a working fluid and a damping mechanism may employ a flow restrictor placed in a fluid pathway between the working fluid and the bung 210. In another exemplary embodiment, a plunger actuator 212 may employ a biasing mechanism and a damping mechanism may employ a viscous damper, a swiss lever escapement, a runaway escapement, and the like. In another exemplary embodiment, a plunger actuator 212 may employ a stepper motor connected to a gear drive system to provide a constant linear administration profile.

The housing 202 of the wearable automatic injection device 200 may also house an administration interface button 216 bearing an administration interface 218 that is configured to administer a therapeutic agent on, in or through the skin to any desired depth. In an exemplary embodiment, the administration interface 218 may be aligned orthogonally to the longitudinal axis L of the device 200. In an exemplary embodiment, the administration interface 218 may be held in place by an administration interface carrier (not pictured) provided in the administration interface button 216 or separately from the administration interface button 216.

In some exemplary embodiments, the administration interface 218 may include one or more injection needles that may have any suitable size, shape and configuration suitable for piercing the skin of the patient to administer the therapeutic agent, and is not limited to the illustrative embodiment. In an exemplary embodiment, the administration interface 218 may include a single injection needle (shown as a continuous line in FIGS. 2A-2F). In another exemplary embodiment, the administration interface 218 may include two or more injection needles (the additional needles shown as dashed lines in FIGS. 2A-2F). In some other exemplary embodiments, the administration interface 218 may include a needle-free pad and/or a needle-free patch for performing a topical administration of a therapeutic agent.

Suitable injection needles that may be used in exemplary administration interfaces may have a length configured or selected to provide an administration depth suitable for the desired therapy. Subcutaneous injections typically penetrate about six to ten millimeters into the skin. In an exemplary embodiment, exemplary injection needles may have a length of about twelve mm and may be administered to a depth of about seven mm into the skin. In other exemplary embodiments, exemplary injection needles may have lengths suitable for intradermal, intramuscular therapies, and the like. Suitable injection needles may have a wall thickness suitable to provide sufficient mechanism strength, a diameter suitable to allow a desired flow rate of the substance while minimizing patient sensation, and a tip geometry suitable for the desired therapy while minimizing patient sensation.

Exemplary injection needles may be coated as needed to minimize patient sensation as allowed by therapy. The administration interface 218 may be covered, protected from mechanical damage and maintained in aseptic condition, i.e., sterile condition, by an administration interface cover 222, for example, a rigid needle shield, a soft needle shield, or both. The administration interface cover 222 may also maintain sterility of the fluid conduit formed by and connected to the administration interface 218.

The administration interface button 216 may also include a pierceable septum disposed in the vicinity of the piercing needle 220. In a pre-administration state, the piercing needle 220 does not pierce the septum, thus prevent fluid communication between the barrel portion 206 and the piercing needle 220. In an administration state, when pierced by a sharp component, for example, the piercing needle 220, the septum may allow the dose to leave the barrel portion 206 and enter the piercing needle 220. In an exemplary embodiment, one or more covers 215 may enclose the septum in a sterility barrier. The covers 215 may be pierced when the piercing needle 220 pierces the septum.

In an exemplary embodiment, the administration interface 218 and the piercing needle 220 may be coupled to and in fluid communication with each other via the body of the administration interface button 216. In another exemplary embodiment, the administration interface 218 and the piercing needle 220 may be coupled to and in fluid communication with each other via one or more fluid conduits (not pictured). In another exemplary embodiment, the administration interface 218 and the piercing needle 220 may be directly coupled to and in fluid communication with each other.

In an exemplary embodiment, before administration in a pre-administration state, the administration interface button 216 may be in a vertically raised position relative to the housing 202 such that the administration interface button 216 protrudes from the top of the housing 202, as illustrated in FIGS. 2A and 2B. In this position, the administration interface 218 may be retracted within the housing 202 and may not interface with the patient's body. In this position, the piercing needle 220 may be aligned vertically below the septum in the syringe stopper 214 and may not pierce the septum. At the beginning of the administration process, the administration interface button 216 may be pressed downward, for example, by a user of the device or automatically. This may push the administration interface button 216 to a vertically depressed position relative to the housing 202 closer to the patient's body such that the administration interface button 216 no longer protrudes from the top of the housing 202, as illustrated in FIGS. 2C-2E. In this position, the administration interface 218 may protrude from the bottom of the housing 202 and may be interface with the patient's body, e.g., by penetrating the patient's body. In this position, the piercing needle 220 may be aligned with the septum in the syringe stopper 214 and may pierce the septum.

In an exemplary embodiment, the septum may initially be spaced from the administration interface button 216. In this embodiment, the piercing needle 220 may pierce the septum when the syringe stopper 214 bearing the piercing needle 220 is advanced within the housing 202 toward the septum. That is, before administration in a pre-administration state, the piercing needle 220 may be spaced from the septum such that there is no fluid communication between the barrel portion 206 and the administration interface 218 coupled to the administration interface button 216. In an administration state, the barrel portion 206 may advance within the housing 202 toward the distal end of the device 200 such that that the piercing needle 220 may pierce the septum and establish fluid communication between the barrel portion 206 and the administration interface 218 coupled to the administration interface button 216. This fluid communication may allow the dose of the therapeutic agent to flow from the barrel portion 206 to the patient through the piercing needle 220 and the administration interface 218 when pressure is applied to the dose by the bung 210 during administration in an administration state.

Referring now to FIG. 2F, in an exemplary embodiment, the housing 202 of the wearable automatic injection device 200 may include a skin sensor foot 232, which is a structure housed under or in the portion of the housing 202 proximal to the administration site. Prior to administration of the therapeutic agent and during administration, the skin sensor foot 232 is retained within or forms a portion of the underside of the housing 202. When the wearable automatic injection device 200 is attached to the administration site and activated, the skin sensor foot 232 may be free to move but may be constrained by the administration site. When the wearable automatic injection device 200 is removed from the administration site, regardless of whether administration of the therapeutic agent was completed, the skin sensor foot 232 is no longer constrained, and extends and projects outside the periphery of the housing 202. This, in turn, activates a retraction trigger. When the retraction trigger is activated, a retraction mechanism retracts the administration interface 220 which may also raise the administration interface button 216 from the vertically lowered position to the vertically raised position, so that the administration interface button 216 protrudes from the top of the housing 202 and the administration interface 218 is retracted within the housing 202.

FIG. 2A illustrates the wearable automatic injection device 200 in a pre-administration state, for example, as packaged, in which the barrel portion 206 may be pre-filled with the dose 208 of the therapeutic agent and in a retracted position ready for use. The barrel portion 206 may contain the dose 208 of the therapeutic agent in the interior space defined between the wall or walls of the barrel portion 206 and the bung 210. In an embodiment, the plunger actuator 212 may store energy that, when released, may actuate the bung 210. The administration interface button 216 may be partially disposed within the housing 202 at the vertically raised position above the administration site, and the administration interface 218 may be retracted within the housing 202. The protrusion of the administration interface button 216 out of the top of the housing 202 may provide a visual indication to the patient that the wearable automatic injection device 200 is not in operation.

FIG. 2B illustrates the wearable automatic injection device 200 in a pre-administration state before administration of the therapeutic agent in which the administration interface cover 222 and the septum cover are removed. In exemplary embodiments, the protective film 228 may include a linking member that is connected to the administration interface cover 222, the septum cover and the piercing needle cover in the syringe stopper 224. The linking member may include a tether, a tab or other linkage mechanism. When the protective film 228 is removed, the linking member of the protective film 228 may automatically remove the administration interface cover 222, the septum cover and the piercing needle cover in the syringe stopper 214.

FIG. 2C illustrates the wearable automatic injection device 200 in an administration state during administration of the therapeutic agent in which the administration interface button 216 is in the vertically lowered position within the housing 202. In the vertically lowered position, the administration interface button 216 may be disposed within the housing 202 at a depressed or vertically lowered location above the administration site, and the administration interface 218 may project from the housing 202 through one or more apertures or open ends in the housing 202 so that it can interface with the patient's body at the administration site. In an exemplary embodiment, a cover portion may be provided for covering the aperture or open end. In an exemplary embodiment, the aperture or open end of the housing may oppose the patient contact portion of the housing such that the administration interface button 216 may be vertically lowered to administer the therapeutic agent. In the vertically lowered state, the administration interface button 216 may not protrude from the top of the housing 202, which may provide a visual indication to the patient that the wearable automatic injection device 200 is in operation. In another exemplary embodiment, the aperture or open end in the housing 202 may not be disposed opposing the patient contact portion and may instead be disposed in a side wall of the housing. The administration interface button 216 may be moved laterally or horizontally in some exemplary embodiments to administer the therapeutic agent.

FIG. 2D illustrates the wearable automatic injection device 200 in an administration state during administration of the therapeutic agent in which the barrel portion 206 containing the dose 208 of the therapeutic agent is deployed forwardly from a retracted position to an extended position within the housing of the device 200. The advancement of the barrel portion 206 may bring the distal end of the barrel portion 206 or the syringe stopper 214 in the vicinity of or in contact with the administration interface button 216. In an exemplary embodiment, the piercing needle 220 may pierce the septum held in the syringe stopper 214 in order to establish fluid communication between the barrel portion 206 and the administration interface 218.

FIG. 2E illustrates the wearable automatic injection device 200 in an administration state during administration of the therapeutic agent in which the plunger actuator 212 is triggered to move the bung 210. Triggering of the plunger actuator 212 may release stored energy in the plunger actuator 212 in order to move the bung 210 within the barrel portion 206 toward the distal end of the device 200. The movement of the bung 210 may eject the dose of the therapeutic agent from the barrel portion 206 through the distal end of the barrel portion 206. Any suitable mechanism may be used to trigger the plunger actuator 212 including, but not limited to, a linking member that is coupled to and activated by the depression of the administration interface button 216 or by the removal of the administration interface cover 222, a trigger button that may be activated by the patient, and the like.

FIG. 2F illustrates the wearable automatic injection device 200 in a post-administration state after administration of a therapeutic agent, for example, after administering a therapeutically effective dose of the therapeutic agent or removal of the wearable automatic injection device 200 from the patient before administration of a therapeutically effective dose of the therapeutic agent, in which the administration interface button 216 is in the vertically raised position. In the vertically raised position, the administration interface button 216 may be disposed partly within the housing 202 at an elevated or vertically raised location above the administration site, and the administration interface 218 may be retracted within the housing 202. A portion of the administration interface button 216 may project from the top of the housing 202 to provide a visual indication to the patient that the wearable automatic injection device assembly 200 is not in operation (i.e., in a post-administration state). The barrel portion 206 may be empty of the therapeutic agent and the plunger actuator 212 may no longer store energy. A skin sensor foot 232 may extend from the bottom of the housing 202 upon removal of the device 200 from the administration site.

The housing 202 may include a retraction mechanism that automatically raises the administration interface button 216 from the vertically lowered administration state (shown in FIGS. 2C-2E) to the vertically raised post-administration state (shown in FIG. 2F). In an exemplary embodiment, the retraction mechanism may include a biasing mechanism, for example, a spring, that biases the syringe assembly away from the administration site when the retraction mechanism is triggered.

A retraction trigger, when activated, may trigger the retraction mechanism in order to raise the administration interface button 216 from the vertically lowered state to the vertically raised state. In an exemplary embodiment, the bung 210 and/or the plunger actuator 212 may include a linking member connected to the retraction trigger. The linking member may include a tether, a tab or other linkage mechanism. The linking member may be of a suitable length such that, when the bung 210 has been moved to the end of the barrel portion 206 (in order to administer a dose of the therapeutic agent), the linking member triggers a latch that in turn activates the retraction trigger. In another exemplary embodiment, the extension of the skin sensor foot 232 from the bottom of the housing 202 may activate the retraction trigger.

In an exemplary embodiment, the retraction mechanism may include an end-of-dose retraction trigger that, when activated, triggers the retraction mechanism. The end-of-dose retraction trigger may be activated when the therapeutically effective dose of therapeutic agent in the wearable automatic injection device 200 is administered. In an exemplary embodiment, the end-of-dose retraction trigger may include a latch, for example, a flexible plastic hook, that is released upon completed administration of the therapeutic agent. The retraction mechanism may also include an early-removal retraction trigger that, when activated, triggers the retraction mechanism. The early-removal retraction trigger may be activated when the wearable automatic injection device 200 is removed from the administration site before the therapeutically effective dose of therapeutic agent is completely administered. In an exemplary embodiment, the early-removal retraction trigger may include a latch, for example, a flexible plastic hook, that is released upon removal of the wearable automatic injection device 200 from the administration site. The retraction mechanism is responsive to the end-of-dose retraction trigger and responsive to the early-removal retraction trigger to automatically retract the syringe assembly from the administration site.

In an exemplary embodiment, raising of the administration interface button 216 to the vertically raised position may cause the piercing needle 220 to bend upward, thus preventing undesirable reuse of the piercing needle and the wearable automatic injection device 200.

In exemplary embodiments, the barrel portion of the wearable automatic injection device 100 (in FIG. 1)/200 (in FIG. 2) may be pre-filled with any suitable volume of a therapeutic agent. In an exemplary embodiment, the barrel portion 106 may be pre-filled with a volume of between about 0.1 milliliters and about 3.0 milliliters, although exemplary devices are not limited to this exemplary range of therapeutic agent volumes. In an exemplary embodiment in which the volume to be administered is larger than the capacity of the barrel portion of the device, two or more barrel portions may be provided in the device for holding the entire volume of the therapeutic agent. Other components in the device may be configured to eject the therapeutic agent from the multiple barrel portions out through an administration interface for administration to the patient. In another exemplary embodiment, two or more automatic injection devices, each including a barrel portion, may be provided to administer the entire volume of the therapeutic agent.

In exemplary embodiments, the wearable automatic injection device 100 (in FIG. 1)/200 (in FIG. 2) may be used to administer a therapeutically effective amount of therapeutic agent over a period of time ranging from about twenty seconds to about twelve hours. Certain other exemplary embodiments provide actuation devices and systems that cause actuation of the syringe plunger at fast rate in order to administer the therapeutic agent to a patient at a fast rate. Exemplary fast embodiments may administer therapeutic agent volumes of about 0.5 milliliters to about 1 milliliter in about one second to about twenty seconds, although exemplary administration rates are not limited to this exemplary range.

Exemplary embodiments may provide a linear administration profile for the therapeutic agent so that the administration rate is substantially constant over time. In some cases, a linear administration profile may reduce discomfort experienced by the patient. In an exemplary embodiment, the therapeutic agent may be administered in a single fast bolus.

The rate of administration of the therapeutic agent may be dependent on the ambient temperature. At room temperature, i.e., about 72° F., the accuracy of the administration time may range between about three percent and about ten percent.

Exemplary dimensions of exemplary devices are described with reference to Tables 1-6. However, one of ordinary skill in the art will recognize that the exemplary dimensions are provided for illustrative purposes, and that exemplary automatic injection devices are not limited to the illustrative dimensions.

In an exemplary embodiment, a wearable automatic injection device may have an exemplary length of about 4.37 inches, an exemplary width of about 2.12 inches, and an exemplary height of about 1.25 inches. In an exemplary embodiment, the diameter of the barrel portion is about 1.470 inches and the length of the barrel portion is about 2.520 inches. Tables 1-3 summarize the components of the length, width and height, respectively, for two exemplary types of the exemplary device.

TABLE 1

Summary of components of the length of an exemplary device (inch)

| Element | Type 1 | Type 2 |
|---|---|---|
| Wall thickness | 0.185 | 0.120 |
| Septum | 0.397 | 0.272 |
| Needle | 0.500 | 0.500 |
| Barrel portion | 2.520 | 2.520 |
| Advance spring | 0.470 | 0.322 |
| Hydraulic connection | 0.113 | 0.113 |
| Wall thickness | 0.185 | 0.120 |
| Total | 4.370 | 3.968 |

TABLE 2

Summary of components of the width of an exemplary device (inch)

| Element | Type 1 | Type 2 |
|---|---|---|
| Wall thickness | 0.185 | 0.120 |
| Administration interface lock | 1.045 | 0.935 |
| Barrel portion width | 0.470 | 0.470 |
| Syringe lock | 0.235 | 0.235 |
| Wall thickness | 0.185 | 0.120 |
| Total | 2.120 | 1.880 |

TABLE 3

Summary of components of the height of an exemplary device (inch)

| Element | Type 1 | Type 2 |
|---|---|---|
| Wall thickness | 0.100 | 0.120 |
| Needle cover | 0.431 | 0.431 |
| Septum | 0.400 | 0.350 |
| Spring solid height | 0.200 | 0.000 |
| Wall thickness | 0.185 | 0.125 |
| Total | 1.316 | 1.026 |

In an exemplary embodiment, the diameter of the barrel portion in production may be increased from about 1.470 inches by about 0.125 inches, and the length of the barrel portion may be decreased in production from about 2.520 inches by about 0.732 inches. Tables 4-6 summarize the components of the length, width and height, respectively, for two exemplary types of the exemplary device.

TABLE 4

Summary of components of the length of an exemplary device (inch)

| Element | Type 1 | Type 2 |
|---|---|---|
| Wall thickness | 0.185 | 0.120 |
| Septum | 0.397 | 0.272 |
| Needle | 0.500 | 0.250 |
| Barrel portion | 2.520 | 1.788 |
| Advance spring | 0.470 | 0.322 |
| Hydraulic connection | 0.113 | 0.113 |
| Wall thickness | 0.185 | 0.120 |
| Total | 4.370 | 2.986 |

TABLE 5

Summary of components of the width of
an exemplary device (inch)

| Element | Type 1 | Type 2 |
|---|---|---|
| Wall thickness | 0.185 | 0.120 |
| Administration interface lock | 1.045 | 0.935 |
| Barrel portion width | 0.470 | 0.595 |
| Syringe lock | 0.235 | 0.235 |
| Wall thickness | 0.185 | 0.120 |
| Total | 2.120 | 2.005 |

TABLE 6

Summary of components of the height of
an exemplary device (inch)

| Element | Type 1 | Type 2 |
|---|---|---|
| Wall thickness | 0.100 | 0.120 |
| Needle cover | 0.431 | 0.493 |
| Septum | 0.400 | 0.350 |
| Spring solid height | 0.200 | 0.000 |
| Wall thickness | 0.185 | 0.125 |
| Total | 1.316 | 1.088 |

Figure 3:
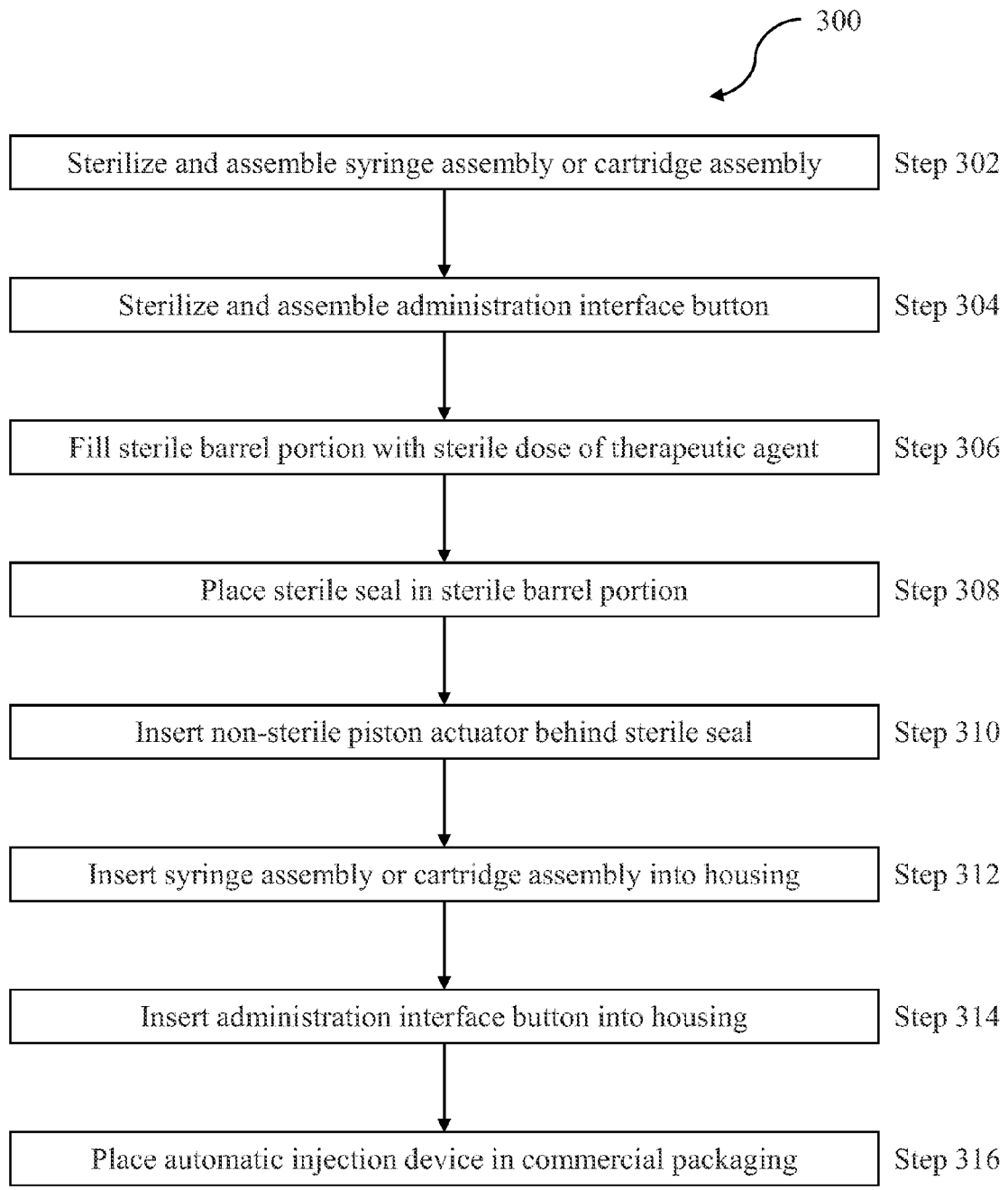
FIG. 3 is a flow chart of an exemplary method of assembling an exemplary wearable automatic injection device.

FIG. 3 is a flow chart of an exemplary method 300 of assembling an exemplary automatic injection device 100.

In step 302, a syringe assembly or a cartridge assembly may be sterilized and assembled.

In step 304, an administration interface button may be sterilized and assembled. In an exemplary embodiment in which the therapeutic agent is contained in a cartridge assembly, the administration interface button may include and/or hold an administration interface, a piercing needle and a fluid pathway provided between the piercing needle and the administration interface. In this exemplary embodiment, the administration interface, the piercing needle and the fluid pathway of the administration interface button may be sterilized before assembly. In an exemplary embodiment, a sterile piercing needle cover, e.g., a foil, a soft or rigid needle cover, etc., may be used to cover the piercing needle and maintain the piercing needle in a sterile condition. In an exemplary embodiment, a sterile cover, e.g., a foil, a soft or rigid needle cover, etc., may be used to cover the administration interface and maintain the administration interface in a sterile condition. The sterile piercing needle, the sterile piercing needle cover, the sterile administration interface and the sterile administration interface cover may provide sterility barriers to maintain sterility of the fluid pathway within the administration interface button during and after assembly of the automatic injection device. Thus, the inner surfaces and fluid pathway within the administration interface button may be maintained in a sterile condition during and after assembly of the automatic injection device so that a sterile therapeutic agent may be administered in a sterile manner.

In another exemplary embodiment in which the therapeutic agent is contained in a syringe assembly, the administration interface button may include and/or hold an administration interface and a fluid pathway for coupling the syringe assembly to the administration interface. In this exemplary embodiment, the administration interface and the fluid pathway of the administration interface button may be sterilized before assembly. In an exemplary embodiment, a sterile cover, e.g., a foil, a soft or rigid needle cover, etc., may be used to cover the administration interface and maintain the administration interface in a sterile condition. In an exemplary embodiment, the administration interface may also include a sterile septum covered by a sterile septum cover for covering and maintaining sterility of the septum. The sterile administration interface, the sterile administration interface cover, the sterile septum and the sterile septum cover may provide sterility barriers to maintain sterility of the fluid pathway within the administration interface button during and after assembly of the automatic injection device. Thus, the inner surfaces and fluid pathway within the administration interface button may be maintained in a sterile condition during and after assembly of the automatic injection device so that a sterile therapeutic agent may be administered in a sterile manner.

In step 306, the sterile barrel portion of the syringe assembly or the cartridge assembly may be filled with a sterile dose of a therapeutic agent that is to be administered to a patient. In step 308, a sterile bung may be placed at a proximal portion (farther from the administration interface) within the barrel portion of the syringe or cartridge assembly to seal the dose of the therapeutic agent within the barrel portion.

In an exemplary embodiment in which the therapeutic agent is contained in a cartridge assembly, a sterile septum covered by a sterile septum cover may be provided at a distal portion (closer to the administration interface) of the barrel portion of the cartridge assembly. The sterile bung and the sterile septum may collectively seal the sterile dose of the therapeutic agent inside the sterile barrel portion. The sterile barrel portion, the sterile bung, the sterile septum and the sterile septum cover may provide sterility barriers to maintain sterility of the fluid pathway within the cartridge assembly during and after assembly of the automatic injection device. Thus, the containment of the therapeutic agent within the sterile barrel portion by the sterile bung and the sterile septum covered by the sterile septum cover maintains sterility of the therapeutic agent during and after assembly of the automatic injection device.

In another exemplary embodiment in which the therapeutic agent is contained in a syringe assembly, a sterile piercing needle may be attached to a distal portion of the barrel portion of the syringe assembly. In an exemplary embodiment, a sterile piercing needle cover, e.g., a foil, a soft or rigid needle cover, etc., may be used to cover the piercing needle and maintain the piercing needle in a sterile condition. The piercing needle cover may also maintain sterility of the fluid conduit formed by and coupled to the piercing needle. The sterile barrel portion, the sterile bung, the sterile piercing needle and the sterile piercing needle cover may provide sterility barriers to maintain sterility of the fluid pathway within the syringe assembly. Thus, the containment of the therapeutic agent within the sterile barrel portion by the sterile bung and the sterile piercing needle covered by the sterile piercing needle cover maintains sterility of the therapeutic agent during and after assembly of the automatic injection device.

Using the exemplary embodiments described above, sterility is maintained in a fluid pathway within and extending between the barrel portion of the syringe or cartridge assembly and the administration interface button. Sterility is maintained during and after assembly of the automatic injection device so that the device may be used to perform a sterile administration of a therapeutic agent. In this manner, exemplary embodiments ensure that, during administration of a sterile therapeutic agent, the therapeutic agent takes or follows a sterile fluid pathway from the syringe or cartridge assembly through the administration interface button to the patient.

In an exemplary embodiment, the remaining components of the wearable automatic injection device may be assembled in a non-sterile environment, while maintaining sterility of the fluid pathway within the device. In another exemplary embodiment, the remaining components may be sterilized before assembly.

In step 310, a non-sterile plunger actuator, for example, a biasing mechanism, may be inserted behind the bung for actuating the bung in an administration state to eject the therapeutic agent from the barrel portion.

In step 312, the syringe or cartridge assembly may be inserted into a non-sterile housing. The housing may be pre-assembled with one or more other non-sterile components, for example, an adhesive layer, a protective film, a skin sensor foot, and the like.

In step 314, the administration interface button (with an enclosed sterile fluid pathway and a sterile administration interface in an exemplary embodiment) may be inserted into the non-sterile housing.

In step 316, the assembled automatic injection device may be placed in an outer packaging, if necessary, and may then be commercially packaged for sale. In an exemplary embodiment, a portion of the device may be attached to a portion of the inner surface of the packaging.

Figure 4:
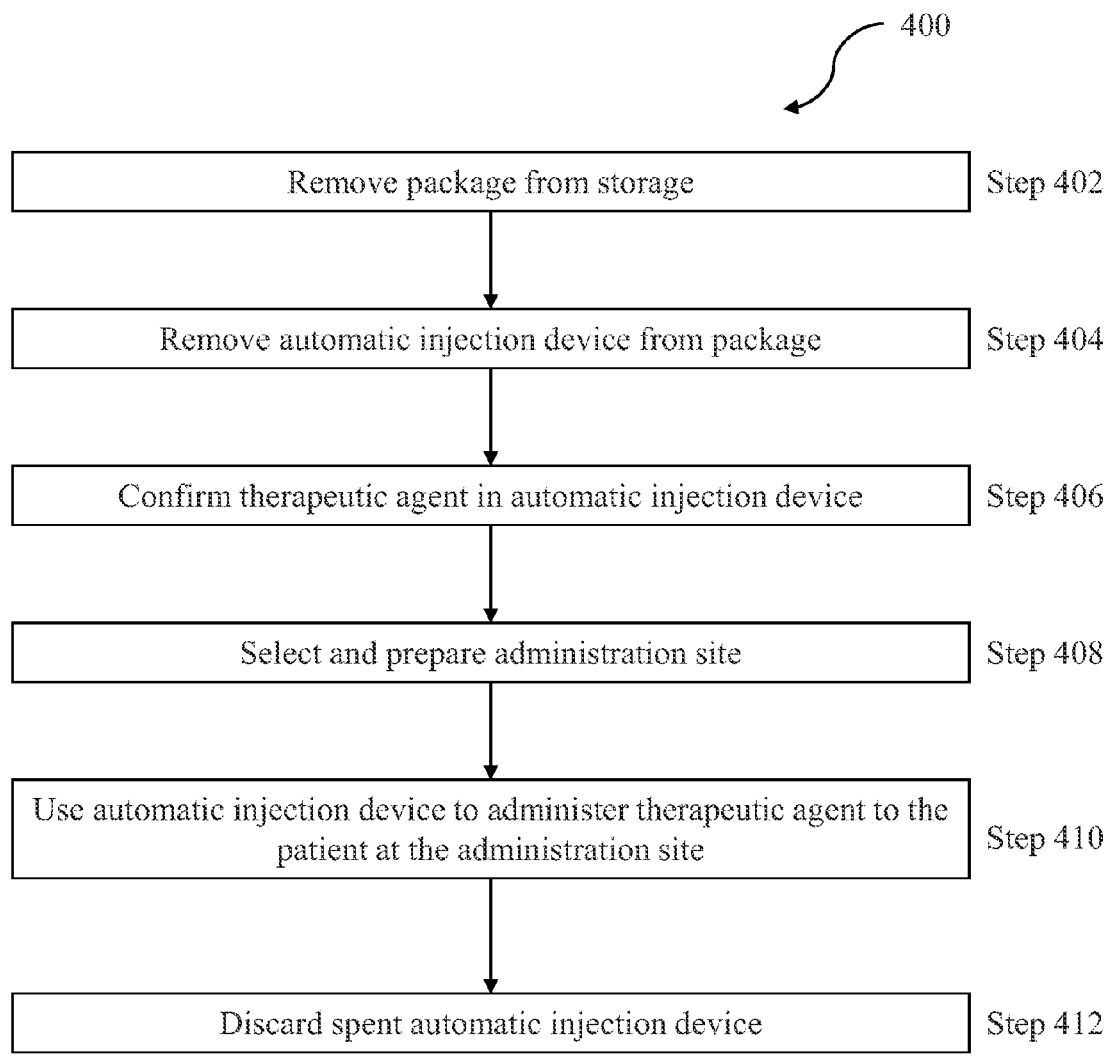
FIG. 4 is a flow chart of an exemplary method of using an exemplary automatic wearable injection device.

FIG. 4 is a flow chart of an exemplary method 400 of using an exemplary automatic injection device. The wearable automatic injection device packaged and pre-filled with a therapeutic agent may be generally stored in refrigerated storage before use. In step 402, the packaged automatic injection device may be removed from storage. In step 404, the wearable automatic injection device may be removed from its packaging and any over-wrap, and warmed to room temperature, for example, by leaving the wearable device outside the packaging at room temperature or by warming the wearable device. In step 406, the patient may confirm that the barrel portion contains a volume of the therapeutic agent through an therapeutic agent inspection window disposed in the device housing, and may also confirm the clarity of the therapeutic agent if necessary.

In step 408, the administration site on the body of the patient may be selected to and prepared for the administration of the therapeutic agent. In step 410, the patient uses the wearable automatic injection device to administer the therapeutic agent to the patient at the administration site. The steps generally involved within step 410 are described below in connection with FIG. 5. In step 412, after administering the therapeutic agent, the wearable automatic injection device may be removed from the patient and discarded in an appropriate manner.

Figure 5:
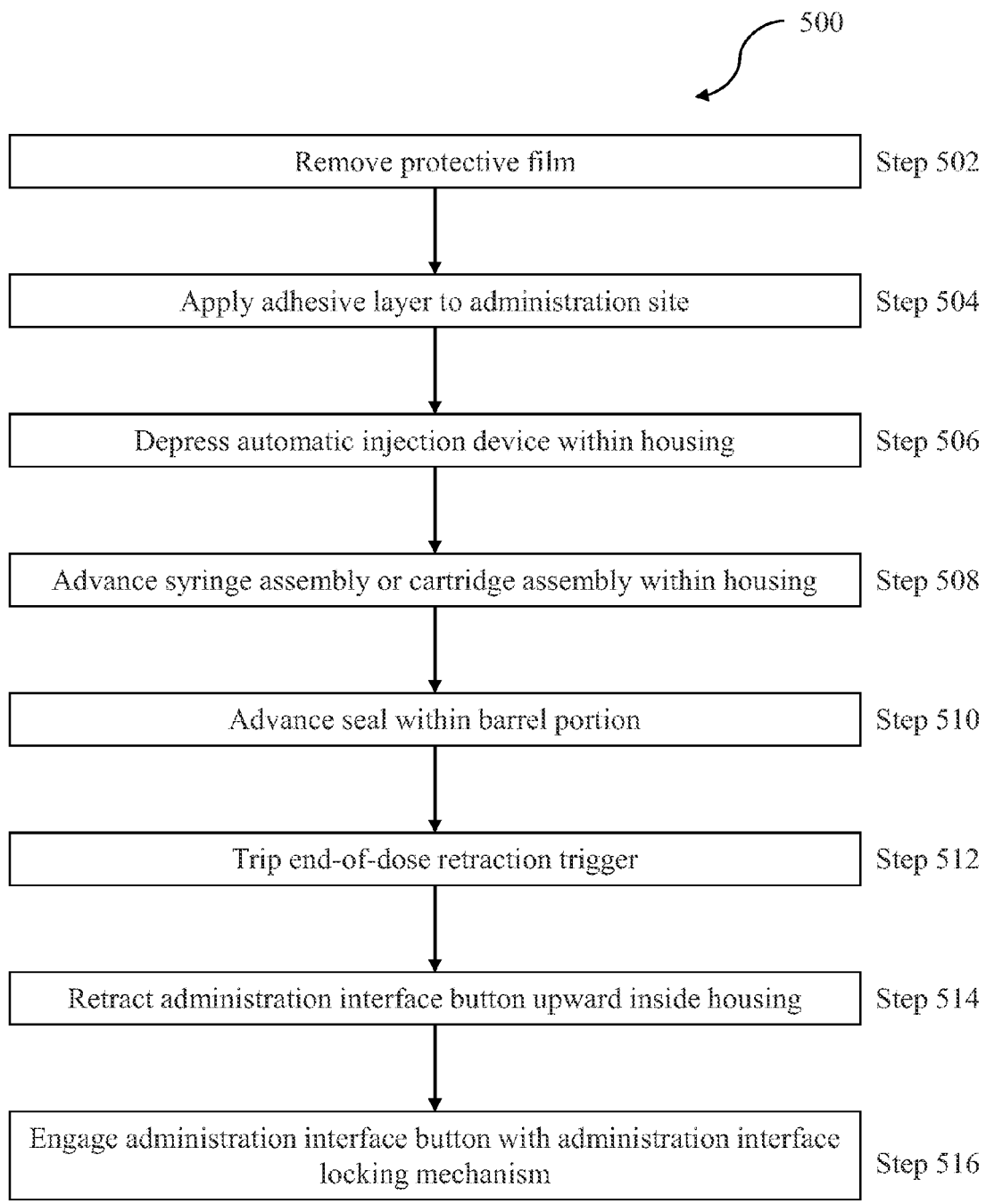
FIG. 5 is a flow chart of an exemplary method of using an exemplary wearable automatic injection device to administer a therapeutic agent to a patient.

FIG. 5 is a flow chart of an exemplary method 500 of using an exemplary automatic injection device to administer a therapeutically effective amount of a therapeutic agent to a patient. Exemplary method 500 is a detailed outline of step 410 in FIG. 4.

In step 502, the patient removes the protective film that covers and protects the adhesive layer of the wearable automatic injection device. In an exemplary embodiment, a portion of the protective film may be attached to the inner surface of the packaging of the device, and removal of the device from the packaging may automatically remove the protective film. In some exemplary embodiments, removal of the protective film also removes the administration interface cover, the piercing needle cover and the septum cover in the syringe or cartridge stopper.

In step 504, the patient applies the patient contact portion of the wearable automatic injection device with the adhesive layer to the administration site on the patient's body (or an article of clothing around the administration site) so that the device is reliably retained on the administration site during the administration of the therapeutically effective dose of therapeutic agent.

In step 506, once the wearable automatic injection device is attached to the administration site, the patient may depress the administration interface button from a vertically raised position in the pre-administration state to a vertically lowered position in the administration state within the housing. In the vertically raised position, the end of the administration interface button bearing the administration interface is retracted within the housing and is not exposed to the outside of the housing. When depressed, the end of the administration interface button bearing the administration interface is moved downward either linearly or rotationally within the housing so that the administration interface emerges from an aperture in the housing and is exposed outside the housing. This allows the administration interface to interface with the patient's body, e.g., by penetrating the patient's body to an appropriate depth, for administration of the therapeutic agent. The downward movement of the administration interface button in the housing may be linear (i.e., a vertical downward movement) or rotary (i.e., in a circular movement about a pivot point).

In an exemplary embodiment, the administration interface button is depressed into the housing by the patient manually pushing down the administration interface button. In another exemplary embodiment, the patient may activate an administration trigger, for example, a trigger button located in a conveniently accessible location such as the top of the housing, which causes the administration trigger to automatically depress the administration interface button into the housing and in turn, cause the administration interface to interface with the patient's body, e.g., by piercing the body of the patient. In an exemplary embodiment, pressing the trigger button may release a latch in the administration trigger that allows a spring to bias the administration interface button downwardly in the housing. The same motion of the administration interface button may cause the administration interface to be inserted into or applied to the administration site on the patient's body to an appropriate depth.

In step 508, depressing the administration interface button may trigger a syringe or cartridge actuator that moves the syringe or cartridge assembly, more specifically, the barrel portion, forwardly within and relative to the housing from a retracted position (in which the distal end of the syringe or cartridge assembly is spaced from the administration interface button) to an extended position (in which the distal end of the syringe or cartridge assembly is adjacent to and/or in contact with the administration interface button). In another exemplary embodiment, the syringe or cartridge actuator is triggered not by depressing the administration interface button, but by the patient activating a trigger, for example, in the form of a trigger button. In an exemplary embodiment, movement of the syringe or cartridge assembly toward the administration interface button may cause the piercing needle to pierce the septum.

In step 510, the plunger actuator may break the static friction (i.e., stiction) between the bung and the inside wall or walls of the barrel portion and cause the bung to move forwardly toward the piercing needle in the administration interface button to administer the therapeutic agent via the administration interface. The plunger actuator may overcome the bung stiction in one step and actuate the bung in a subsequent step, or the plunger actuator may overcome the bung stiction and actuate the bung concurrently. Movement of the bung may cause the dose to be released through the piercing needle into the administration interface, and the dose may thereby be administered to the patient.

In an exemplary embodiment, the forward advancement of the syringe or cartridge assembly within the housing and the forward advancement of the bung within the barrel portion may take place in separate steps. In another exemplary embodiment, the forward advancement of the syringe or cartridge assembly within the housing and the forward advancement of the bung within the barrel portion may take place in the same step, for example, simultaneously.

The rate of therapeutic agent administration may depend on the characteristics of the plunger actuator. The plunger actuator may take the form of several exemplary embodiments. In some exemplary embodiments, the plunger actuator may employ means of energy storage and release, for example, biasing mechanisms (including, but not limited to, one or more springs, for example, spiral springs or helical compression springs), compressed gases, chemical gas generators (such as expanding foams), osmotic pressure, hydrogel expansion, and the like. A damping or control mechanism (including, but not limited to, a viscous damper or an escapement) may be used to absorb energy, for example, an initial release of energy, and to provide a more controlled release of energy during energy release by the plunger actuator. A flow restrictor placed in a fluid pathway between the administration interface and the bung may be used to further regulate the rate of therapeutic agent administration, for example, where the plunger actuator administers an unconstrained spring force via a working fluid. Thus, an appropriate plunger actuator and an appropriate control mechanism may be selected to administer the dose at a controlled rate, for example, in a single fast bolus, free of or substantially free of any burning sensation to the patient.

In an exemplary embodiment, depressing the administration interface button may arm the retraction mechanism which, when triggered, retracts the administration interface button into the housing 102 after administration in a post-administration state.

In step 512, upon administration of the therapeutically effective dose, the bung and/or the plunger actuator may activate the end-of-dose retraction trigger of the retraction mechanism. The bung and/or the plunger actuator may include a linking member connected to the end-of-dose retraction trigger. The linking member may include a tether, a tab or other linkage mechanism. The linking member may be of a suitable length such that, when the bung has been moved to the end of the syringe or cartridge assembly (in order to administer a dose of the therapeutic agent), the linking member triggers a latch that in turn activates the retraction trigger.

In step 514, once the end-of-dose retraction trigger is activated, the retraction mechanism may retract the administration interface button upward inside the housing and away from the patient contact portion so that the syringe or cartridge assembly enters a post-administration state. In an exemplary embodiment, the movement of the administration interface button from the administration state to the post-administration state creates an audible sound, for example, a "click," which provides an aural indication of the completion of therapeutic agent administration. Once retracted, the administration interface button protrudes outside the housing, which provides a visual indication of the state of the wearable automatic injection device, for example, completion of therapeutic agent administration or a visual indication of the device in the post-administration state.

However, if the wearable device is removed from the body of the patient before the completion of therapeutically effective dose of the therapeutic agent, the skin sensor foot may extend to the outside of the housing and activate the early-removal retraction trigger of the retraction mechanism. Once the early-removal retraction trigger is activated, the retraction mechanism deploys the administration interface button upward in the housing away from the patient contact portion so that the syringe or cartridge assembly enters a post-administration state. In an exemplary embodiment, the plunger actuator may continue to move forwardly in the barrel portion toward the piercing needle when the device is removed from the patient before completion of administration of a therapeutically effective dose of the therapeutic agent.

In step 516, upon retraction, an administration interface locking mechanism engages with the administration interface to prevent redeployment of the administration interface after administration of the therapeutic agent in order to provide needle-stick protection. The administration interface lock may be a member that prevents the administration interface from protruding outside the housing once engaged, and may be located in the housing near the administration interface. Exemplary administration interface locks may include, but are not limited to, a plastic plate, a metal plate, a clip, and the like.

Figure 6A:
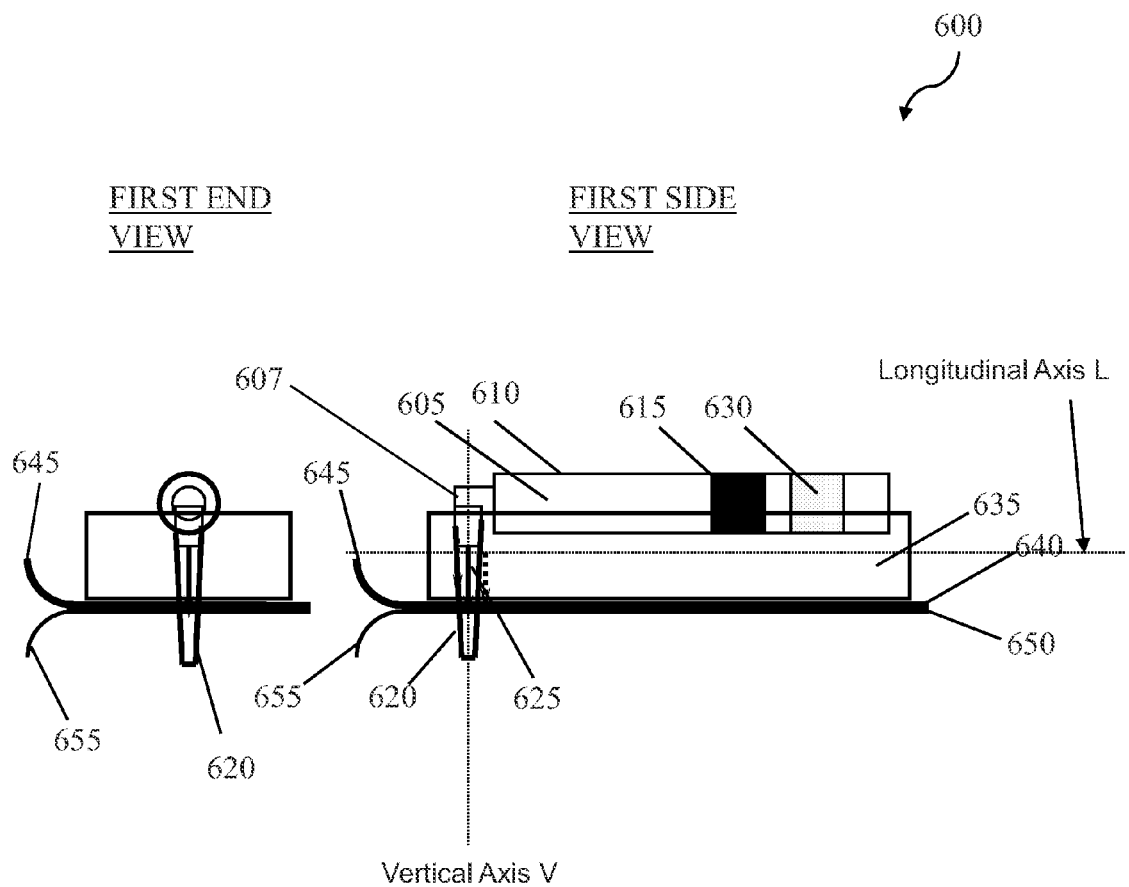
FIG. 6A illustrates an exemplary wearable automatic injection device suitable for linear insertion into or application to a patient's body in a pre-administration state.
Figure 6B:
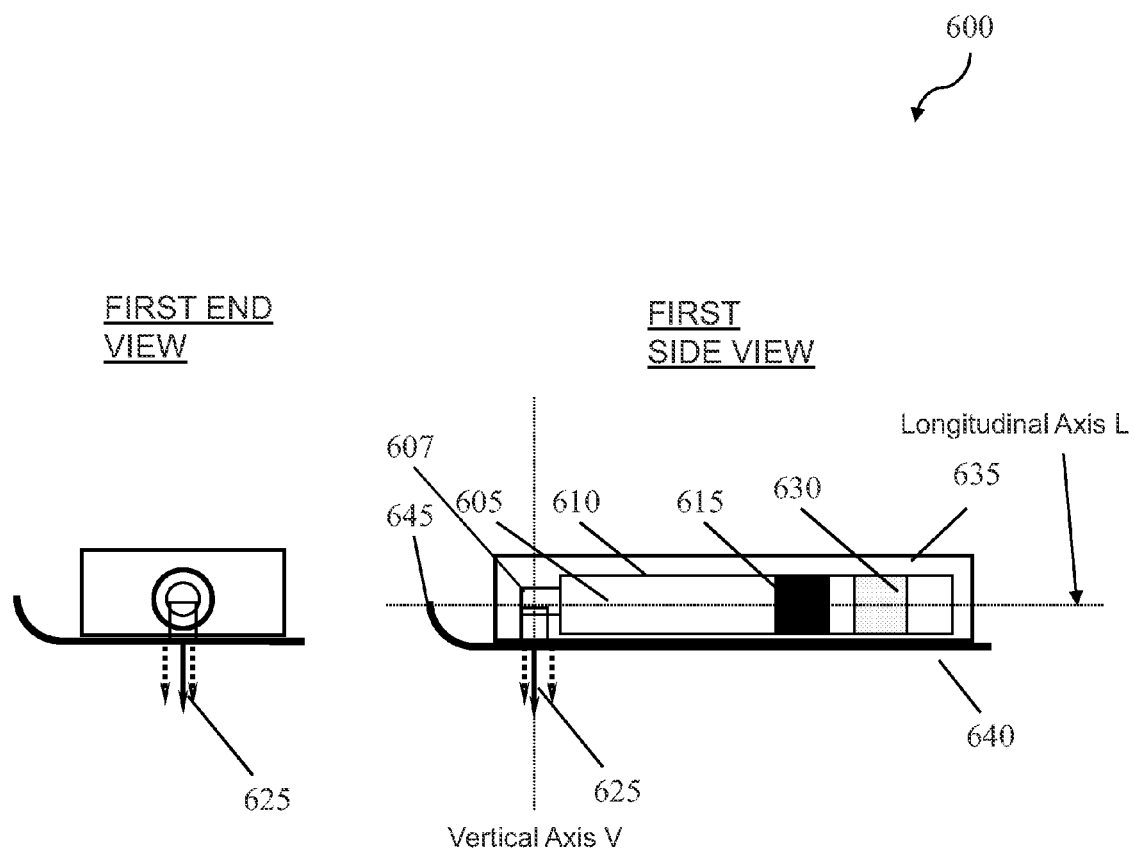
FIG. 6B illustrates the exemplary device of FIG. 6A in an administration state ready to administer or in the process of administering a dose of a therapeutic agent to a patient.
Figure 6C:
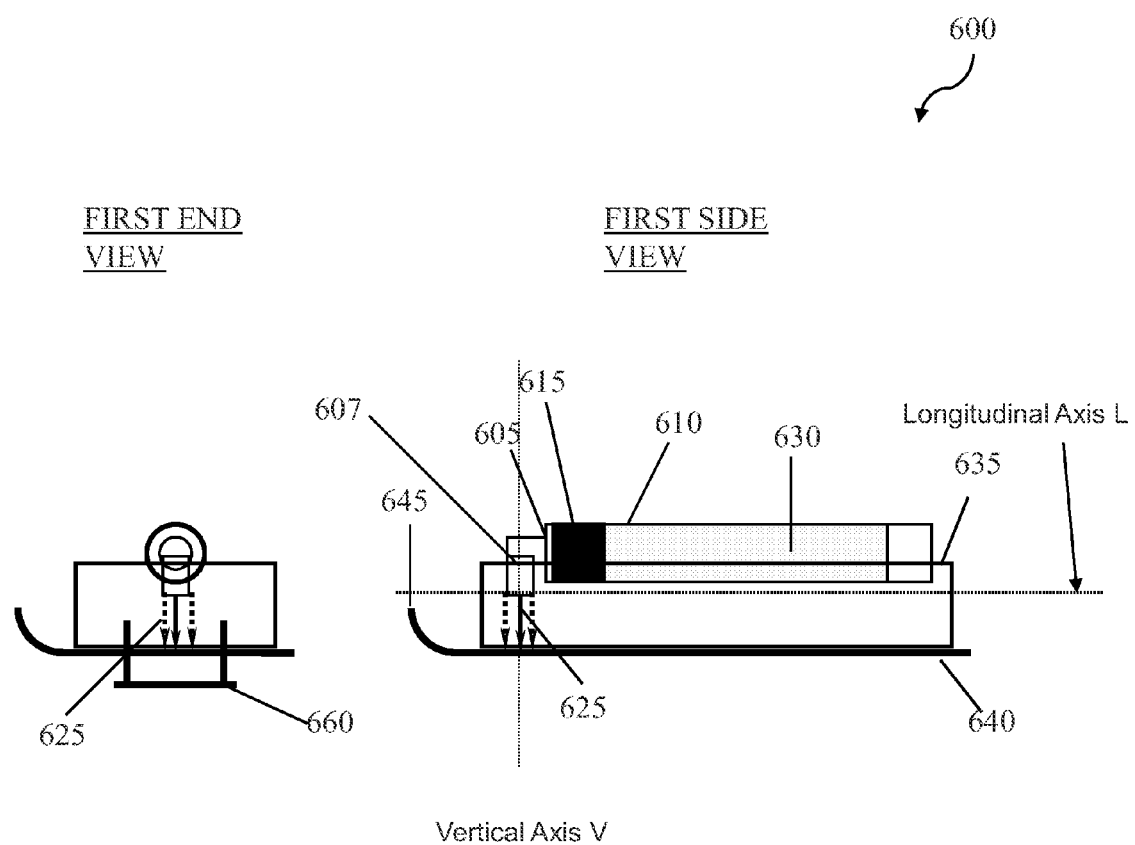
FIG. 6C illustrates the exemplary device of FIGS. 6A and 6B in a post-administration state after it has completed administering the therapeutic agent to the patient or removed from the patient prior to completion of the administration of the therapeutic agent.

FIGS. 6A-6C illustrate an exemplary embodiment of a wearable automatic injection device 600 suitable for linear insertion or application of an administration interface to a patient. By linear insertion, the end of a cartridge assembly bearing an administration interface descends linearly within a housing of the wearable automatic injection device so that the administration interface is inserted into or applied to the patient. More specifically, FIG. 6A illustrates the exemplary wearable device in a pre-administration state, for example, as packaged; FIG. 6B illustrates the exemplary wearable device in an administration state just before, while or just after it administers a therapeutic agent to a patient; and FIG. 6C illustrates the exemplary wearable device in a post-administration state after it has completed administration of the therapeutic agent to the patient or removed from the patient prior to completion of administration of the therapeutic agent. In some of FIGS. 6A-6C, the administration interface is represented as a single injection needle. However, exemplary administration interfaces are not limited to the illustrative embodiments shown in FIGS. 6A-6C.

The wearable automatic injection device 600 includes a housing 635 for housing a therapeutic agent cartridge assembly 610 which contains a dose of a therapeutic agent for administering to a patient. In an exemplary embodiment, the outside of the therapeutic agent cartridge assembly 610 may be provided with one or more ridges, and the inside of the housing 635 may be provided with one or more grooves or channels that provide a smooth pathway for the ridges of the cartridge assembly 610 as the cartridge assembly moves within the housing 635. The one or more ridges on the outside of the cartridge assembly 610 may take the form of raised lines on the cartridge assembly 610. The one or more grooves or channels on the inside of the housing 635 may take the formed of U-shaped depressed or trough-like lines. The top portion of the grooves or channels may be open so that the ridges may slide in and out of the top portion of the grooves or channels. In the linear insertion embodiment illustrated in FIGS. 6A-6C, the ridges and grooves/channels may be straight lines. In the rotary insertion embodiment illustrated in FIGS. 7A-7C, the ridges and grooves/channels may be lines that are curved about the center of rotation, i.e., the pivot point of the cartridge assembly 610.

In another exemplary embodiment, the outside of the cartridge assembly 610 may not have any ridges, and the inside of the housing 635 may not have any grooves or channels.

The housing 635 preferably has an elongated configuration, though one of ordinary skill in the art will recognize that the housing 635 may have any suitable size, shape and configuration for housing a barrel portion for holding a dose of a therapeutic agent and couplable to an administration interface for administering the therapeutic agent to a patient. The housing 635 may be formed of any suitable material including, but not limited to, plastic and other known materials. In another embodiment, the therapeutic agent cartridge 610 may be formed of any compatible material suitable for sterilization including, but not limited to, glass and other known materials.

The housing 635 includes an adhesive layer 640 disposed along a patient contact portion of the housing 635 that is placed proximal to the skin of the patient or an article of clothing of the patient. In some embodiments, the adhesive layer 640 is configured to be placed on the skin of the patient to attach the housing 635 to the patient to administer a therapeutic agent. The adhesive layer 640 includes a non-adhesive removal mechanism 645, e.g., a tab, which is not adhesive. The non-adhesive removal mechanism 645 may be gripped by the patient and pulled to remove the adhesive layer 640 and thus the wearable automatic injection device 600 from the skin or clothing of the patient.

Before the wearable automatic injection device 600 is put to use, for example, in the pre-administration state, the adhesive layer 640 is covered by a protective film 650 which preserves the adhesive nature of the adhesive layer 640. The protective film 650 may include a removal mechanism 655, e.g., a tab, which may be gripped by the patient and pulled to remove the protective film 650 from the adhesive layer 640. This exposes the adhesive layer 640, allowing the patient to attach the housing 635 to his or her skin or an article of clothing by placing the side with the adhesive layer 640 on the skin or the article of clothing.

Figure 7A:
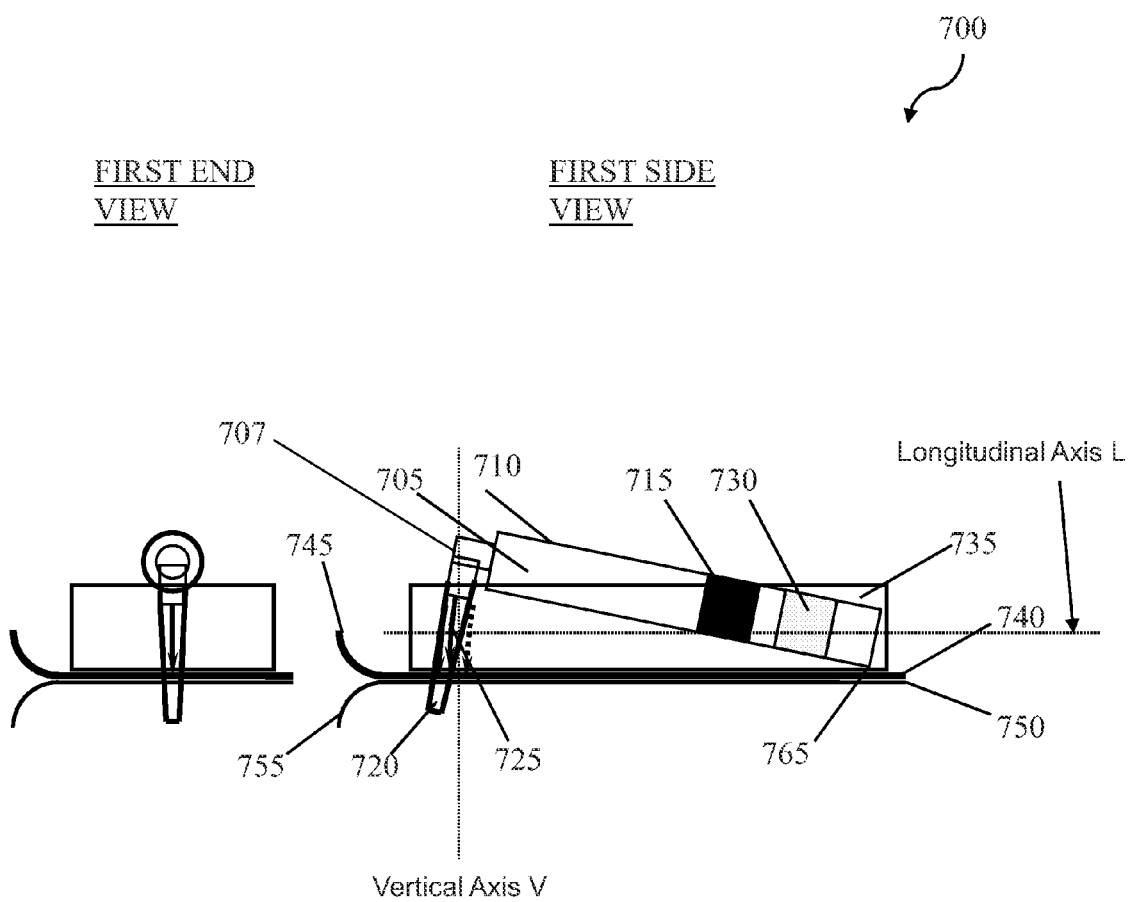
FIG. 7A illustrates an exemplary wearable automatic injection device suitable for rotary insertion in a pre-administration state ready for use by a patient.

In exemplary embodiments, the protective film 650 (in FIG. 6A)/750 (in FIG. 7A) may include a linking member that is connected to the plunger actuator 630 (in FIG. 6A)/730 (in FIG. 7A). The linking member may include a tether, a tab or other linkage mechanism. When the protective film 650 (in FIG. 6A)/750 (in FIG. 7A) is removed, the linking member of the protective film 650 (in FIG. 6A)/750 (in FIG. 7A) relieves static friction between the bung 615 (in FIG. 6A)/715 (in FIG. 7A) and the interior wall of the barrel 605 (in FIG. 6A)/705 (in FIG. 7A), and triggers the plunger actuator 630 (in FIG. 6A)/730 (in FIG. 7A).

The therapeutic agent cartridge assembly 610 may include a hollow barrel portion 605 for holding a therapeutically effective dose of the therapeutic agent to be administered to a patient. The illustrative barrel portion 605 is substantially cylindrical in shape, although one of ordinary skill in the art will recognize that the barrel portion 605 may have any suitable shape or configuration. A bung 615 seals the dose of the therapeutic agent within the barrel portion 605. The therapeutic agent cartridge assembly 610 may also include an administration interface 625 couplable or coupled to, and in fluid communication with, the barrel portion 605, through which the dose can be ejected by applying pressure to the bung 615.

In some exemplary embodiments, the administration interface 625 may include one or more injection needles having any suitable size, shape and configuration suitable for piercing the skin of the patient to administer the therapeutic agent, and is not limited to the illustrative embodiment. In an exemplary embodiment, the administration interface 625 may include a single injection needle (shown as a continuous line in FIGS. 6A-6C). In another exemplary embodiment, the administration interface 625 may include two or more injection needles (the additional needles shown as dashed lines in FIGS. 6A-6C). In some other exemplary embodiments, the administration interface 625 may include a needle-free pad and/or a needle-free patch for performing a topical administration of a therapeutic agent.

Suitable needles that may be used in exemplary administration interfaces may have a length configured or selected to provide an administration depth suitable for the desired therapy. Subcutaneous injections typically penetrate about six to ten millimeters into the skin. In an exemplary embodiment, exemplary injection needles may have a length of about twelve mm and may be administered to a depth of about seven mm into the skin. In other exemplary embodiments, exemplary injection needles may have lengths suitable for intradermal, other subcutaneous, or intramuscular therapies. Suitable needles may have a wall thickness suitable to provide sufficient mechanism strength, a diameter suitable to allow a desired flow rate of the substance while minimizing patient sensation, and a tip geometry suitable for the desired therapy while minimizing patient sensation.

Exemplary injection needles may be coated as needed to minimize patient sensation as allowed by therapy. The administration interface 625 may be covered and maintained in a septic condition by an administration interface cover 620, for example, a soft needle shield, a rigid needle shield or both.

In the exemplary embodiment illustrated in FIGS. 6A-6C, the administration interface 625 projects substantially at a right angle to the longitudinal axis of the wearable device 600. In this exemplary embodiment, the barrel portion 605 includes an elbow 607 that extends substantially at a right angle to the longitudinal axis of the device 600. In this embodiment, the administration interface 625 is connected to the elbow 607.

The wearable automatic injection device 600 may include a plunger actuator 630 for selectively actuating the bung 615 forwardly toward the distal end of the therapeutic agent cartridge assembly 610 to administer the therapeutically effective dose contained in the barrel portion 605 to the patient. The plunger actuator 630 may employ an energy storage and controlled energy release mechanism to actuate the bung 615. In an exemplary embodiment, the plunger actuator 630 may include a biasing mechanism, for example, a spring, that is retracted before administration and that is released during administration to actuate the bung 615 forwardly in the barrel portion 605. In another exemplary embodiment, the plunger actuator 630 may include a chemical gas generator, for example, an expanding foam, that is in a non-expanded phase before administration and that expands during administration to actuate the bung 615 forwardly in the barrel portion 605 toward the distal end of the therapeutic agent cartridge assembly 610. In other exemplary embodiments, the plunger actuator 630 may employ compressed gases, osmotic pressure, hydrogel expansion, and the like. A damping mechanism may be used to absorb energy, for example, an initial release of energy, and to provide a controlled release of energy during energy release by the plunger actuator 630 (in FIG. 6A)/730 (in FIG. 7A).

A flow restrictor placed in a fluid pathway between the administration interface and the bung 615 (in FIG. 6A)/715 (in FIG. 7A) may be used to further regulate the rate of therapeutic agent administration, for example, where the plunger actuator 630 (in FIG. 6A)/730 (in FIG. 7A) administers an unconstrained spring force.

In an exemplary embodiment, the plunger actuator 630 may be advanced forwardly inside the barrel portion 605 in a constant linear motion. Any number of mechanisms, internal or external to the wearable automatic injection device 600, may be used to provide a constant linear motion including, but not limited to, a stepper motor connected to a gear drive system.

The bung 615 (in FIG. 6A)/715 (in FIG. 7A) and/or the plunger actuator 630 (in FIG. 6A)/730 (in FIG. 7A) may include a linking member connected to the retraction trigger. The linking member may include a tether, a tab or other linkage mechanism. The linking member may be of a suitable length such that, when the bung 615 (in FIG. 6A)/715 (in FIG. 7A) has been moved to the end of the cartridge assembly 610 (in FIG. 6A)/710 (in FIG. 7A) (in order to administer a dose of the therapeutic agent), the linking member triggers a latch that in turn activates the retraction trigger.

Referring now to FIG. 6C, in an exemplary embodiment, the housing 635 includes a skin sensor foot 660, which is a structure housed under or in the portion of the housing 635 proximal to the administration site. Prior to administration of the therapeutic agent and during administration, the skin sensor foot 660 is retained within or forms a portion of the underside of the housing 635. When the wearable automatic injection device 600 is attached to the administration site and activated, the skin sensor foot 660 may be free to move but may be constrained by the administration site. When the wearable automatic injection device 600 is removed from the administration site, regardless of whether administration of the therapeutic agent was completed, the skin sensor foot 660 is no longer constrained, and extends and projects outside the periphery of the housing 635. This, in turn, activates the removal retraction trigger.

FIG. 6A illustrates the wearable automatic injection device 600 in a pre-administration state, for example, as packaged and ready for use or as ready for packaging. The device 600 may include a pre-fillable and/or pre-filled syringe or cartridge assembly. In an exemplary embodiment, in a pre-administration state, the syringe or cartridge assembly may be in a retracted position ready for use. In the pre-administration state, the therapeutic agent cartridge assembly 610 is partially disposed within the housing 635 at an elevated location distal from the administration site, and the administration interface 625 is retracted within the housing 635. Visual indications to the patient that the wearable automatic injection device 600 is not in operation may include a portion of the therapeutic agent cartridge assembly 610 projecting outside the housing 635 in the pre-administration state. The barrel portion 605 contains a dose of a therapeutic agent which is contained by the interior space defined between the wall or walls of the barrel portion 605 and the bung 615. In an embodiment, the plunger actuator 630 stores energy.

FIG. 6B illustrates the wearable automatic injection device 600 in an administration state ready to administer, in the process of administering or just after administering a therapeutically effective dose of a therapeutic agent, in which the therapeutic agent cartridge assembly 610 is in a depressed position. In the depressed position, the therapeutic agent cartridge assembly 610 is disposed within the housing 635 at a depressed location proximal to the administration site, and the administration interface 625 projects outside the housing 635 through an aperture in the housing 635 so that it can penetrate the body at the administration site. In the administration state, the therapeutic agent cartridge assembly 610 does not project outside the housing 635 to provide a visual indication to the patient that the wearable automatic injection device 600 is in operation. The plunger actuator 630 releases its stored energy to actuate the bung 615. This cooperative movement of the plunger actuator 630 and the bung 615 ejects the therapeutic agent in the barrel portion 605 out through the administration interface 625.

FIG. 6C illustrates the wearable automatic injection device 600 in a post-administration state, for example, after administering a therapeutically effective dose of the therapeutic agent or removal of the wearable automatic injection device 600 from the patient before administration of a therapeutically effective dose of the therapeutic agent, in which the therapeutic agent cartridge assembly 610 is in a retracted position. In the retracted position, the therapeutic agent cartridge assembly 610 is disposed within the housing 635 at an elevated location distal from the administration site, and the administration interface 625 is retracted within the housing 635. A portion of the therapeutic agent cartridge assembly 610 projects outside the housing 635 to provide a visual indication to the patient that the wearable automatic injection device assembly 600 is not in operation (i.e., in a post-administration state). The barrel portion 605 may be empty of the therapeutic agent, and the plunger actuator 630 may no longer store energy.

The housing 635 includes a retraction mechanism that automatically raises the therapeutic agent cartridge assembly 610 from the administration state (depressed position shown in FIG. 6B) to the post-administration state (retracted position shown in FIG. 6C). In an exemplary embodiment, the retraction mechanism may include a biasing mechanism, for example, a spring, that biases the cartridge assembly away from the administration site when the retraction mechanism is triggered.

The retraction mechanism includes an end-of-dose retraction trigger that, when activated, triggers the retraction mechanism. The end-of-dose retraction trigger is activated when the therapeutically effective dose of therapeutic agent in the wearable automatic injection device is administered. In an exemplary embodiment, the end-of-dose retraction trigger may include a latch, for example, a flexible plastic hook, that is released upon completed administration of the therapeutic agent. The retraction mechanism also includes an early-removal retraction trigger that, when activated, triggers the retraction mechanism. The early-removal retraction trigger is activated when the wearable automatic injection device is removed from the administration site before the therapeutically effective dose of therapeutic agent is completely administered. In an exemplary embodiment, the early-removal retraction trigger may include a latch, for example, a flexible plastic hook, that is released upon removal of the wearable automatic injection device 600 from the administration site. The retraction mechanism is responsive to the end-of-dose retraction trigger and responsive to the early-removal retraction trigger to automatically retract the cartridge assembly from the administration site.

Figure 7B:
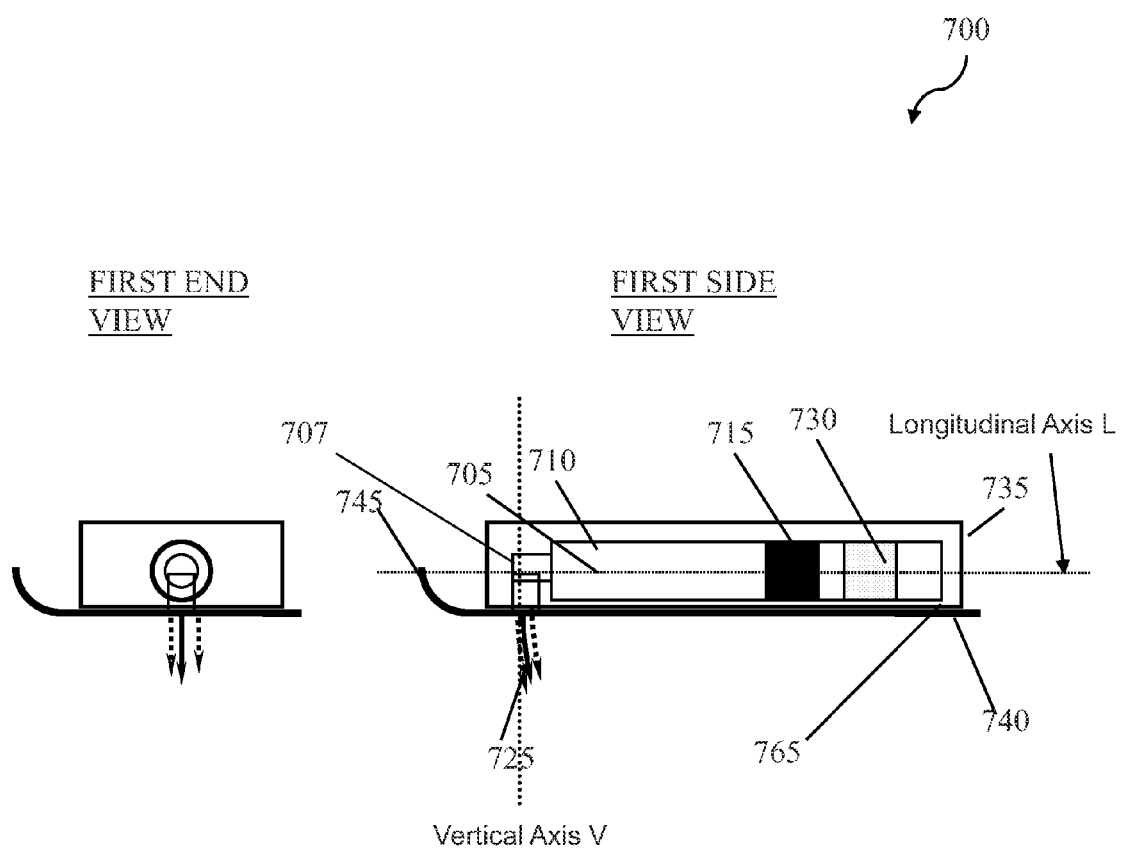
FIG. 7B illustrates the exemplary device of FIG. 7A in an administration state ready to administer or in the process of administering a dose of a therapeutic agent to a patient.
Figure 7C:
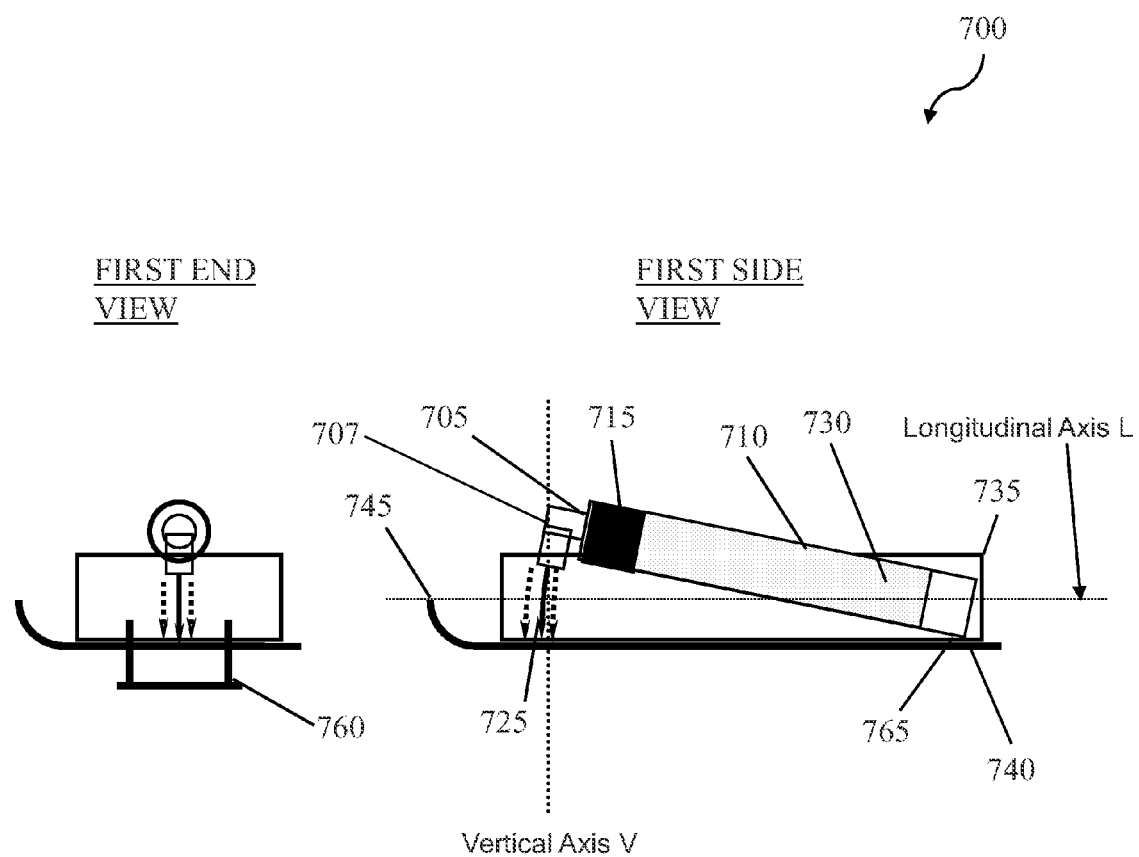
FIG. 7C illustrates the exemplary device of FIGS. 7A and 7B in a post-administration state after it has completed administering the therapeutic agent to the patient or removed from the patient prior to completion of the administration of the therapeutic agent.

FIGS. 7A-7C illustrate an exemplary embodiment of a wearable automatic injection device 700 suitable for rotary insertion or application of the administration interface to a patient. In rotary insertion, the end of a therapeutic agent cartridge assembly 710 bearing an administration interfaces 725 descends in a rotary fashion about a pivot point to insert or apply the administration interface 725 to the patient. The administration interface 725 may be configured to administer a therapeutic agent on, in or through the skin to any desired depth. More specifically, FIG. 7A illustrates the exemplary wearable device in a pre-administration state, for example, as packaged with a pre-filled and curved administration interface and barrel portion holding a therapeutic agent; FIG. 7B illustrates the exemplary wearable device while in an administration state just before, while or just after administering a therapeutic agent to a patient; and FIG. 7C illustrates the exemplary wearable device in a post-administration state after administration of the therapeutic agent to the patient or removal of the wearable device from the patient prior to completing administration of the therapeutic agent to the patient. In some of FIGS. 7A-7C, the administration interface is represented as a single injection needle. However, exemplary administration interfaces are not limited to the illustrative embodiments shown in FIGS. 7A-7C.

The therapeutic agent cartridge assembly 710 is rotatably movable within the housing 735 about a pivot point 765 in the housing. In an exemplary embodiment, the outside of the therapeutic agent cartridge assembly 710 may be provided with one or more ridges, and the inside of the housing 735 may be provided with one or more grooves or channels that provide a pathway for the ridges of the cartridge 710 as the cartridge moves within the housing 735 amongst the various states. In another exemplary embodiment, the outside of the cartridge assembly 710 is free of ridges, and the inside of the housing 735 is free of grooves or channels.

When the therapeutic agent cartridge assembly 710 is depressed into the housing 735, the therapeutic agent cartridge assembly 710 moves rotatably downward about the pivot point 765 such that the administration interface 725 becomes exposed and penetrates the skin of the patient. In an exemplary embodiment, the administration interface 725 may include a single injection needle (shown as a continuous line in FIGS. 7A-7C). In another exemplary embodiment, the administration interface 725 may include two or more injection needles (the additional needles shown as dashed lines in FIGS. 7A-7C). In some other exemplary embodiments, the administration interface 725 may include a needle-free pad and/or a needle-free patch for performing a topical administration of a therapeutic agent.

In the exemplary embodiment illustrated in FIGS. 7A-7C, the administration interface 725 penetrates the skin of the patient at an angle offset from 90°. Similarly, when the therapeutic agent cartridge assembly 710 is retracted, the therapeutic agent cartridge assembly 710 moves rotatably upward about the pivot point 765 such that the administration interface 725 retracts within the housing 735. The mechanism to implement this rotational motion of the therapeutic agent cartridge assembly 710 may be simpler and more robust than the mechanism required for the linear insertion of FIGS. 6A-6C.

In an exemplary embodiment, the administration interface 725 is curved, with a radius defined by the pivot point 765 and the distance from the administration interface 725 to the pivot point 765 along the longitudinal axis of the housing 735. The curvature of the administration interface 725 increases the comfort of the patient during application of the administration interface. For example, in an exemplary embodiment, the curvature of the administration interface 725 increases comfort of the patient during insertion of one or more injection needles of an exemplary administration interface into the patient's body. In an exemplary embodiment in which the administration interface 725 includes one or more injection needles, the administration interface 725 may be preferentially oriented with the sharp needle tip closest to the pivot point 765.

Features in FIGS. 7A-7C similar to those illustrated in FIGS. 6A-6C are described above in connection with FIGS. 6A-6C.

In exemplary embodiments, the therapeutic agent cartridge assembly 610 and 720 of FIGS. 6A-6C and 7A-7C, respectively, may be pre-filled with any volume of a therapeutic agent, for example, a therapeutic antibody. In an exemplary embodiment, the cartridge assembly 610 and 720 may be pre-filled with a volume of about 0.1 to about 3.0 milliliters, although exemplary cartridge assemblies are not limited to these exemplary volumes. In another exemplary embodiment, the cartridge assembly 610 and 720 may be pre-filled with a volume of up to about 1 milliliter.

In exemplary embodiments, the wearable automatic injection device 600 (in FIG. 6A)/700 (in FIG. 7A) may be used to administer the therapeutically effective amount of therapeutic agent over a period of time ranging from about twenty seconds to about twelve hours. In an exemplary embodiment, the therapeutic agent may be administered at a fixed rate for an administration time of between about five minutes and about thirty minutes. The wearable automatic injection device 600 (in FIG. 6A)/700 (in FIG. 7A) may be used to administer a volume of therapeutic agent in a single fast bolus.

The rate of administration of the therapeutic agent may be dependent on the ambient temperature. At room temperature, i.e., about 72° F., the accuracy of the administration time may range between about three percent and about ten percent.

Figure 8:
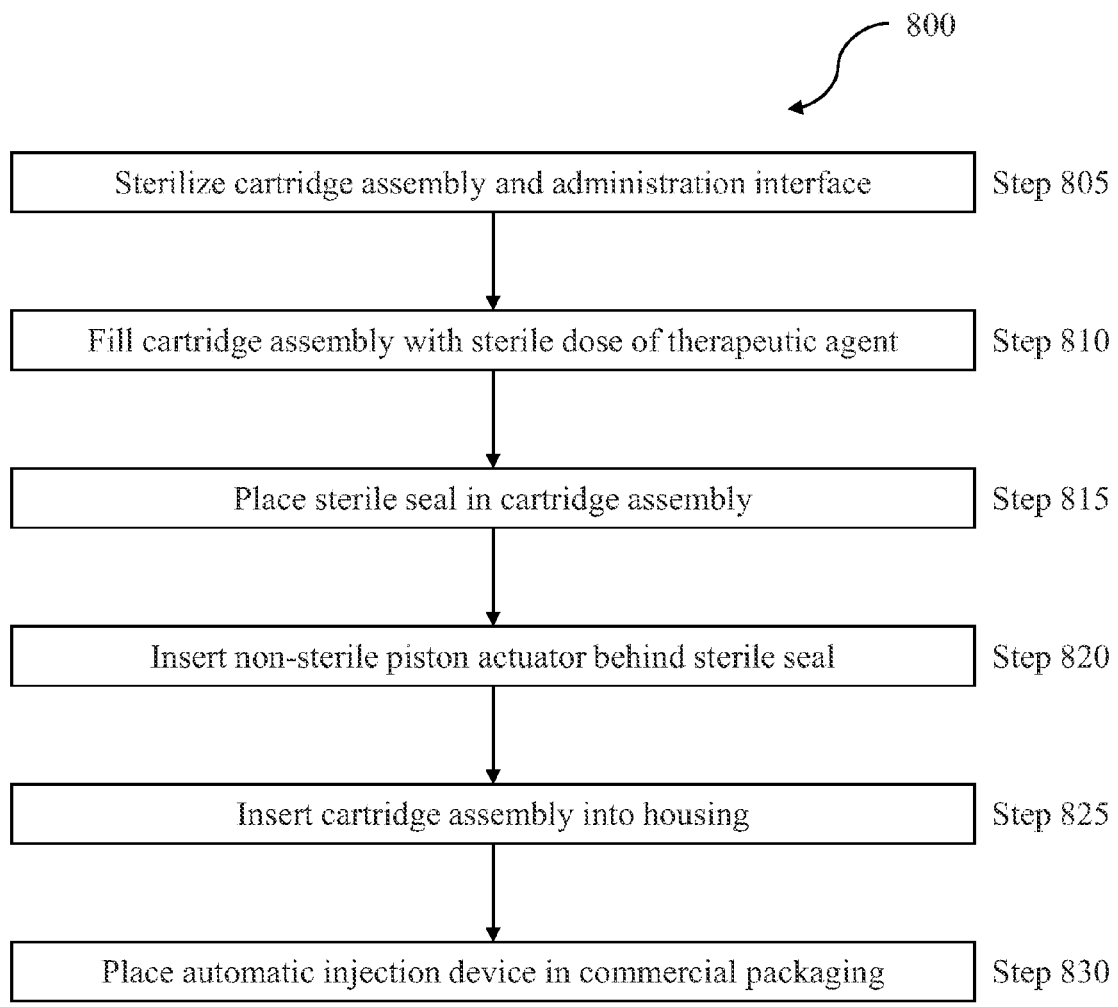
FIG. 8 is a flow chart of an exemplary method of assembling an exemplary wearable automatic injection device.

FIG. 8 is a flow chart of an exemplary method 800 of assembling an exemplary wearable automatic injection device 600 or 700.

In step 805, the barrel portion 605/705 of the cartridge assembly, administration interface 625/725 and administration interface cover 620/720 are sterilized. In step 810, the barrel portion 605/705 is filled with a sterile dose of the therapeutic agent that is to be administered to the patient. In step 815, a sterile bung 615/715 is placed in the barrel portion 605/705 to seal the therapeutic agent inside the barrel portion 605/705. The containment of the therapeutic agent inside the wearable automatic injection device 600 or 700 by the sterile barrel portion 605/705, the sterile bung 615/715, the administration interface 625/725, and the cover assembly 620/720 provide sterility barriers to maintain sterility of a fluid pathway of the therapeutic during and after assembly of the device.

In an exemplary embodiment, the remaining components of the wearable automatic injection device may be assembled in a non-sterile environment after the barrel portion 605/705 is pre-filled with a therapeutic agent, while maintaining sterility of the fluid pathway within the device. In another exemplary embodiment, the remaining components of the wearable automatic injection device may be assembled in a sterile environment.

In step 820, a non-sterile plunger actuator 630/730 is inserted behind the bung 615/715 in the therapeutic agent cartridge assembly 610/710 for actuating the bung in an administration state to eject the therapeutic agent from the barrel portion.

In step 825, the therapeutic agent cartridge assembly 610/710 is inserted into a non-sterile housing 635/735. The housing 635/735 may be pre-assembled with one or more other non-sterile components, for example, the adhesive layer 640/740, the protective film 650/750, the skin sensor foot 660/760.

In step 830, the assembled wearable automatic injection device 600/700 may be placed in an outer packaging, if necessary, and is then commercially packaged for sale. In an exemplary embodiment, a portion of the device may be attached to a portion of the inner surface of the packaging.

Figure 9:
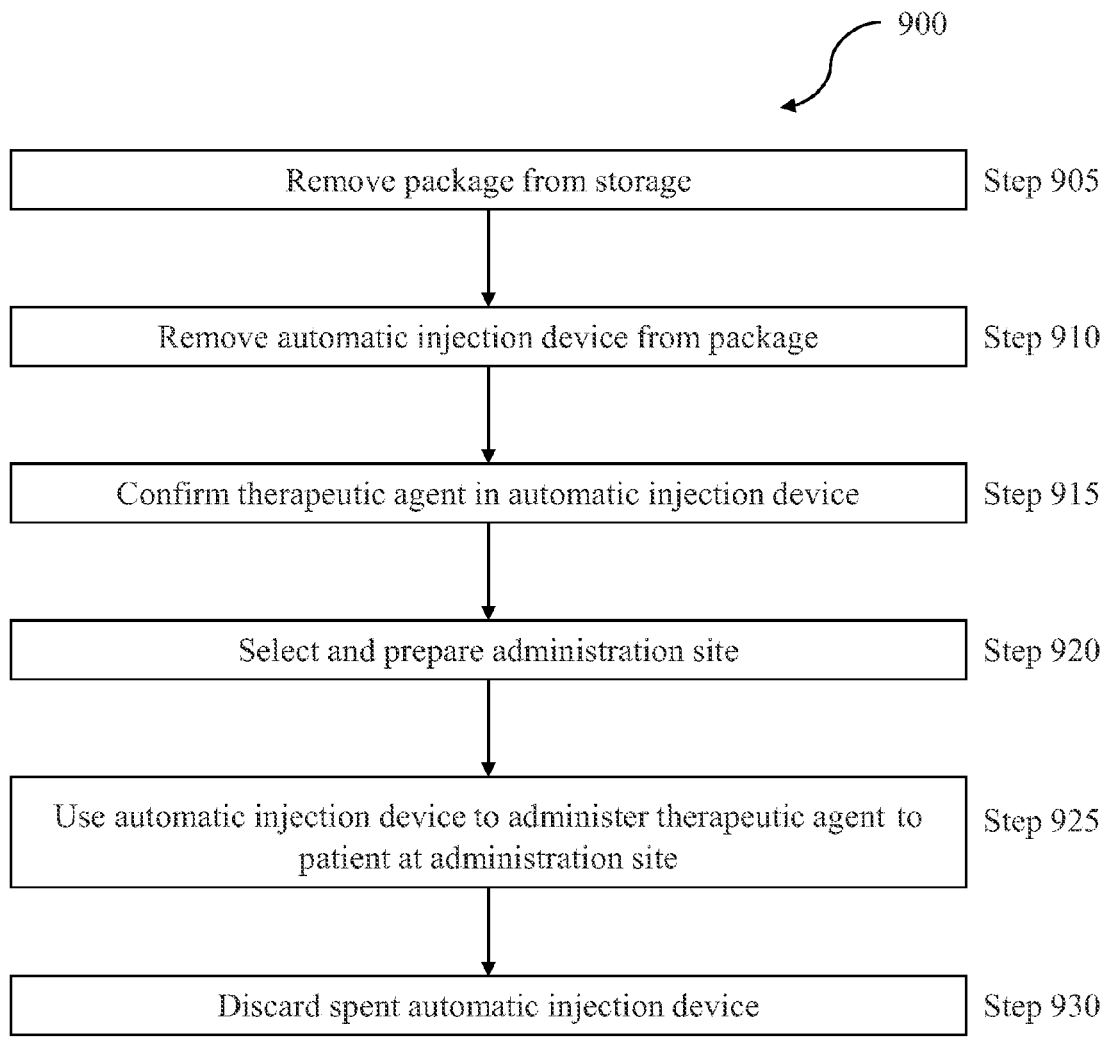
FIG. 9 is a flow chart of an exemplary method of using an exemplary wearable automatic injection device.

FIG. 9 is a flow chart of an exemplary method 900 of using an exemplary wearable automatic injection device 600 or 700. The wearable automatic injection device 600/700 packaged and pre-filled with a therapeutic agent is generally stored in refrigerated storage before use. In step 905, the packaged wearable automatic injection device 600/700 is removed from storage. In step 910, the wearable automatic injection device 600/700 is removed from its packaging and any over-wrap and warmed to room temperature, for example, by leaving the wearable device outside the packaging at room temperature or by warming the wearable device. In step 915, the patient confirms the therapeutic agent cartridge assembly 610/710 includes a volume of the therapeutic agent in the wearable device 600/700 through an therapeutic agent inspection window disposed in the wearable device housing and may also confirm the clarity of the therapeutic agent, if necessary. In step 920, the administration site on the patient's body is selected and prepared for the administration of the therapeutic agent. In step 925, the patient uses the wearable automatic injection device 600/700 to administer the therapeutic agent to the administration site on the patient. The steps generally involved within step 920 are described below in connection with FIG. 10. In step 930, after the wearable automatic injection device 600/700 is removed from the patient, the removed wearable automatic injection device 600/700 is discarded in an appropriate manner.

Figure 10:
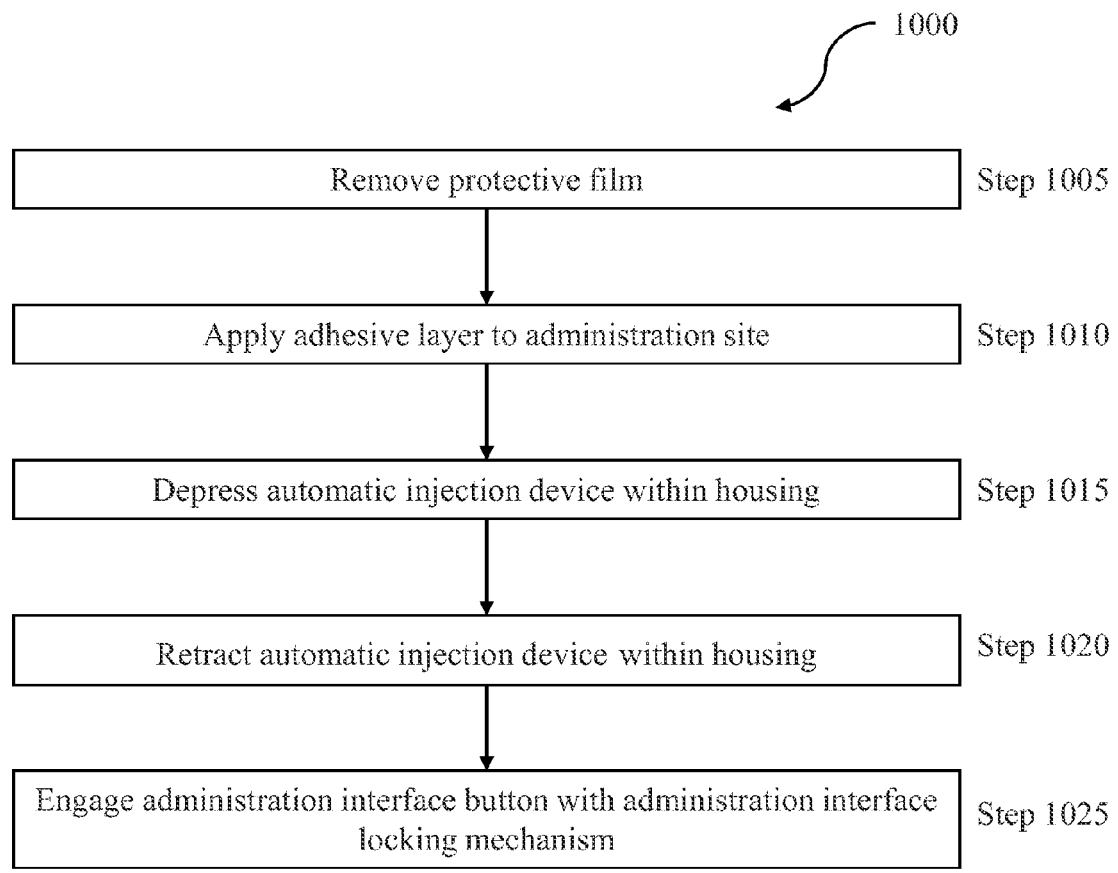
FIG. 10 is a flow chart of an exemplary method of using an exemplary wearable automatic injection device to administer a therapeutic agent to a patient.

FIG. 10 is a flow chart of an exemplary method 1000 of using an exemplary wearable automatic injection device 600 or 700 to administer a therapeutically effective amount of a therapeutic agent to a patient. Exemplary method 1000 is a detailed outline of step 920 in FIG. 9. In step 1005, the patient removes the protective film 650/750 that covers and protects the adhesive layer 640/740 of the wearable automatic injection device 600/700. In an exemplary embodiment, a portion of the protective film may be attached to the inner surface of the packaging, and removal of the device from the packaging may automatically remove the protective film. In some exemplary embodiments, removal of the protective film 650/750 also removes the cover assembly 620/720 and exposes the administration interface 625/725 for administering the therapeutic agent to the patient. In some exemplary embodiments, removal of the protective film 650/750 also breaks static friction (i.e., stiction) between the bung 615/715 and the interior wall of the barrel 605/705 and triggers the plunger actuator 630/730. In exemplary embodiments, the protective film 650/750 may include a linking member that is connected to the plunger actuator 630/730. The linking member may include a tether, a tab or other linkage mechanism. When the protective film 650/750 is removed, the linking member of the protective film 650/750 relieves static friction between the bung 615/715 and the interior wall of the barrel 605/705, and triggers the plunger actuator 630/730.

In step 1010, the patient applies the patient contact portion of the wearable automatic injection device 600/700 with the adhesive layer 640/740 to the administration site (or an article of clothing around the administration site) so that the wearable device is reliably retained on the administration site during the administration of the therapeutically effective dose of therapeutic agent.

In step 1015, once the wearable automatic injection device 600/700 is attached to the administration site, the therapeutic agent cartridge assembly 610/710 is depressed from a ready position in the pre-administration state to a depressed position in the administration state within the housing 635/735. In the ready position, the end of the therapeutic agent cartridge assembly 610/710 bearing the administration interface 625/725 is retracted within the housing 635/735 and is not exposed to the outside of the housing. When depressed, the end of the therapeutic agent cartridge assembly 610/710 bearing the administration interface 625/725 is moved downward either linearly or rotationally within the housing 635/735 so that the administration interface 625/725 emerges from an aperture in the housing 635/735 and is exposed. This allows the administration interface 625/725 to penetrate the body of the patient to an appropriate depth for administration of the therapeutic agent. The downward movement of the therapeutic agent cartridge assembly 610/710 in the housing 635/735 may be linear (i.e., a vertical downward movement) or rotary (i.e., in a circular movement about a pivot point). FIGS. 6B and 7B illustrate exemplary embodiments of the wearable automatic injection device 600 and 700 in an administration state with the therapeutic agent cartridge 610/710 depressed into the housing 635/735 after step 1015 is performed.

In an exemplary embodiment, the therapeutic agent cartridge assembly 610/710 is depressed into the housing 635/735 by the patient manually pushing down the therapeutic agent cartridge assembly 610/710. In another exemplary embodiment, the patient may activate an insertion trigger, for example, a trigger button located in a conveniently accessible location such as the top of the housing 635/735, which causes an insertion trigger to automatically depress the therapeutic agent cartridge assembly 610/710 into the housing 635/735 and in turn, cause the administration interface 625/725 to pierce the body of the patient. In an exemplary embodiment, pressing the trigger button may release a latch in the trigger that allows a spring to bias the cartridge assembly 610/710 downwardly in the housing 635/735. The same motion of the cartridge assembly 610/710 may cause the administration interface 625/725 to be inserted into or applied to the administration site on the patient to an appropriate depth.

In an exemplary embodiment, depressing the therapeutic agent cartridge assembly 610/710 triggers the plunger actuator 630/730 to begin movement of the bung 615/715 to cooperatively administer the therapeutically effective dose to the patient. Depression of the therapeutic agent cartridge assembly 610/710 causes the plunger actuator 630/730 to break the static friction (i.e., stiction) between the bung 615/715 and the inside wall or walls of the barrel portion 605/705 and cause the bung 615/715 to move forwardly toward the administration interface 625/725 in the therapeutic agent cartridge assembly 610/710 to administer the therapeutic agent via the administration interface 625/725. The plunger actuator 630/730 may overcome the bung stiction in one step and actuate the bung in a subsequent step, or the plunger actuator 630/730 may overcome the bung stiction and actuate the bung concurrently. In another exemplary embodiment, the plunger actuator 630/730 is triggered not by depressing the therapeutic agent cartridge, but by the patient activating an administration trigger, for example, in the form of a trigger button.

The rate of therapeutic agent administration may depend on the characteristics of the plunger actuator 630/730. The plunger actuator 630/730 may take the form of several exemplary embodiments. In some exemplary embodiments, the plunger actuator 630/730 may employ means of energy storage and release, for example, biasing mechanisms (such as springs), compressed gases, chemical gas generators (such as expanding foams), osmotic pressure, hydrogel expansion, and the like. A damping mechanism may be used to absorb energy, for example, an initial release of energy, and to provide a more controlled release of energy during energy release by the plunger actuator 630/730. A flow restrictor placed in a fluid pathway between the administration interface and the bung 615/715 may be used to further regulate the rate of therapeutic agent administration, for example, where the plunger actuator 630/730 administers an unconstrained spring force. Thus, an appropriate plunger actuator 630/730 and an appropriate flow restrictor may be selected to administer the dose at a controlled rate, for example, in a single fast bolus free, of or substantially free of any burning sensation to the patient.

In an exemplary embodiment, depressing the therapeutic agent cartridge assembly 610/710 also arms the retraction mechanism which, when triggered, retracts the therapeutic agent cartridge assembly 610/710 into the housing 635/735.

In step 1020, the therapeutic agent cartridge assembly 610/710 is retracted from the depressed position to a retracted position in a post-administration state so that it protrudes outside the housing 635/735 and the administration interface 625/725 is retracted within the housing 635/735 or protected by the skin sensor foot 660/760 or both. FIGS. 6C and 7C illustrate exemplary embodiments of automatic injection device 600 and 700, respectively, in a retracted position after step 1020. Step 1020 is performed either when the therapeutically effective dose of therapeutic agent is administered or when the wearable automatic injection device 600/700 is removed from the administration site before the therapeutically effective dose is completely administered.

Upon administration of the therapeutically effective dose, the bung 615/715 and/or the plunger actuator 630/730 activates the end-of-dose retraction trigger of the retraction mechanism. The bung 615/715 and/or the plunger actuator 630/730 may include a linking member connected to the retraction trigger. The linking member may include a tether, a tab or other linkage mechanism. The linking member may be of a suitable length such that, when the bung 615/715 has been moved to the end of the cartridge assembly 610/710 (in order to administer a dose of the therapeutic agent), the linking member triggers a latch that in turn activates the retraction trigger.

Once the end-of-dose retraction trigger is activated, the retraction mechanism deploys the therapeutic agent cartridge assembly 610/710 upward inside the housing 635/735 and away from the patient contact portion so that the therapeutic agent cartridge assembly 610/710 enters a post-administration state. In an exemplary embodiment, the movement of the therapeutic agent cartridge assembly 610/710 from the administration state to the post-administration state creates an audible sound, for example, a "click," which provides an aural indication of the completion of therapeutic agent administration. Once retracted, the therapeutic agent cartridge assembly 610/710 protrudes outside the housing 635/735 (as shown in FIGS. 6C and 7C), which provides a visual indication of the state of the wearable automatic injection device 600/700, for example, completion of therapeutic agent administration or a visual indication of the device in the post-administration state.

However, if the wearable device 600/700 is removed from the body of the patient before the completion of therapeutically effective dose of the therapeutic agent, the skin sensor foot 660/760 extends to the outside of the housing 635/735 and activates the early-removal retraction trigger of the retraction mechanism. Once the early-removal retraction trigger is activated, the retraction mechanism deploys the therapeutic agent cartridge assembly 610/710 upward in the housing 635/735 away from the patient contact portion so that the therapeutic agent cartridge assembly 610/710 is returned to a retracted position. In an exemplary embodiment, the plunger actuator 630/730 may continue to move forwardly in the therapeutic agent cartridge 610/720 toward the administration interface 625/725 when the wearable device 600/700 is removed from the patient before completion of administration of a therapeutically effective dose of the therapeutic agent.

In step 1025, upon retraction, an automatic administration interface lock engages with the administration interface 625/725 to prevent its redeployment to provide needle-stick protection. The administration interface lock may be a member that prevents the administration interface 625/725 from exiting the housing 635/735 once engaged, and may be located in the housing 635/735 near the administration interface 625/725. Exemplary administration interface locks may include, but are not limited to, a plastic plate, a metal plate, a clip, and the like.

Figure 11A:
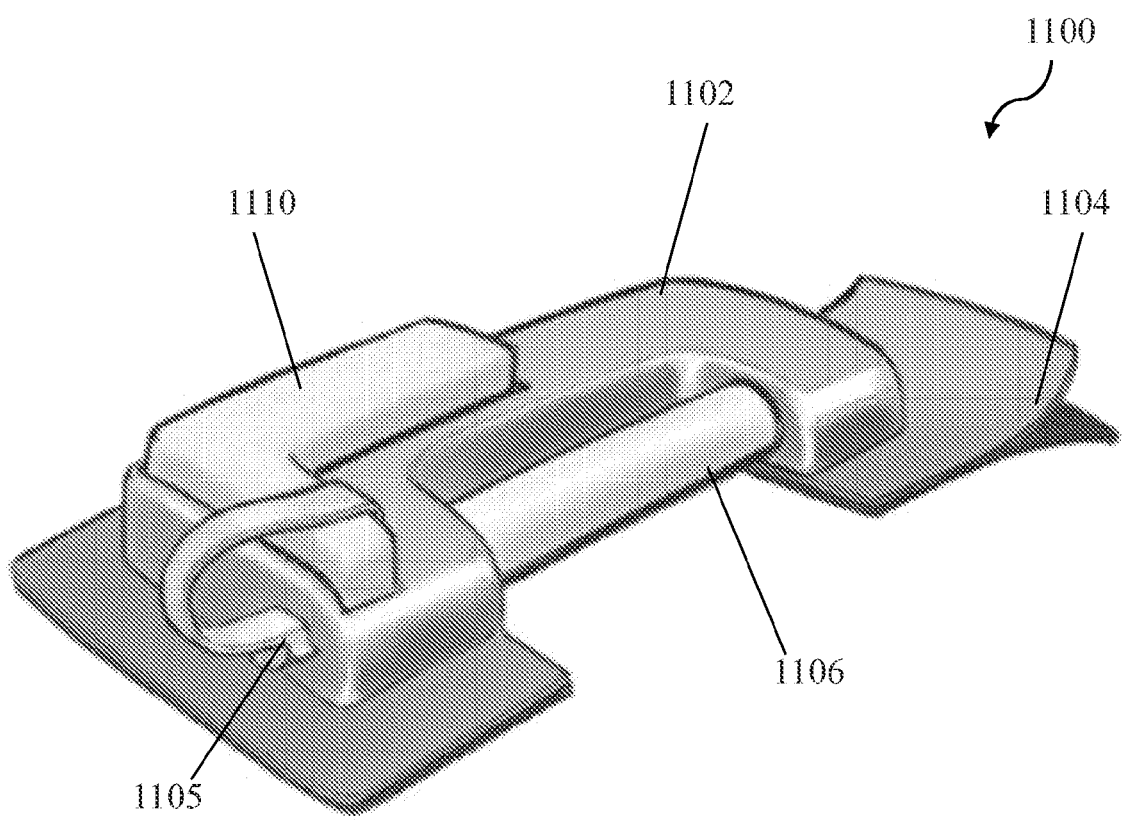
FIG. 11A illustrates a perspective view of an exemplary wearable automatic injection device.
Figure 11B:
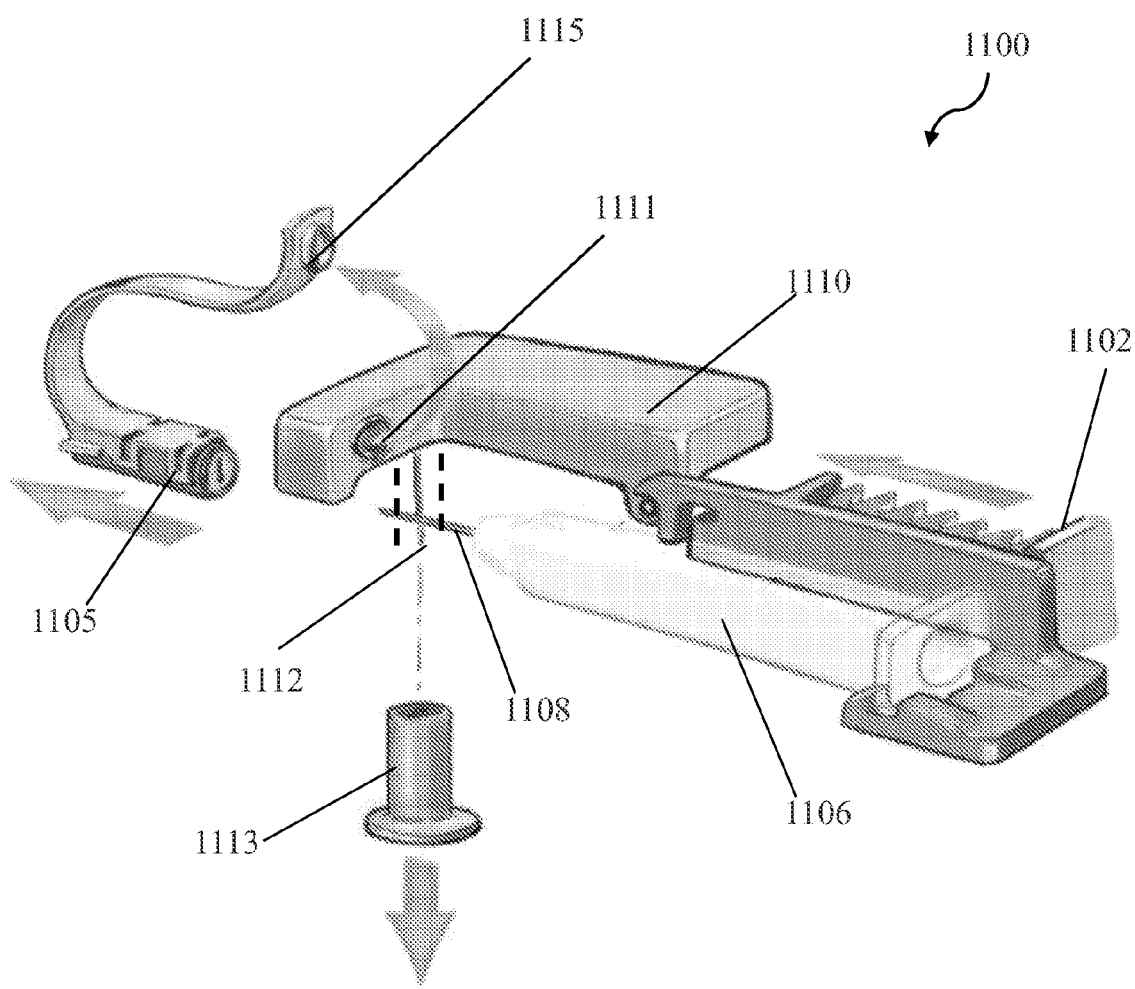
FIG. 11B illustrates an exploded view showing the components of the device of FIG. 11A.

FIGS. 11A and 11B illustrate an exemplary wearable automatic injection device including a syringe and an exemplary transfer mechanism. FIG. 11A illustrates a perspective view of the device. FIG. 11B illustrates a disassembled view showing the components of the device. The automatic injection device 1100 includes a housing portion 1102 that includes an adhesive layer 1104 provided at a patient contact portion that may be used to attach the device to a patient's body or clothing.

The housing portion 1102 holds a syringe 1106 in a stationary or moveable manner in the device 1100. The syringe 1106 holds a dose of a therapeutic agent and is coupled to a piercing needle 1108 at its distal end. The piercing needle 1108 may extend substantially along the longitudinal axis of the syringe 1106. In a packaged pre-administration state, the piercing needle 1108 may be covered by a piercing needle cover 1105, which may be removed by a patient before administration so that the piercing needle 1108 is uncovered in an administration state. The piercing needle cover 1105 may maintain sterility of the piercing needle and a fluid conduit formed by and coupled to the piercing needle 1108. In an exemplary embodiment, removal of the adhesive layer 1104 may also remove the piercing needle cover 1105.

An administration interface button 1110 is provided in the vicinity of the piercing needle 1108. The administration interface button 1110 holds an administration interface 1112 configured to administer a therapeutic agent on, in or through the skin to any desired depth. The administration interface 1112 may be configured at substantially 90 degrees relative to the piercing needle 1108, and may include a transfer mechanism that provides a fluid conduit between the piercing needle 1108 and the administration interface 1112. In an exemplary embodiment, the administration interface 1112 may include a single injection needle (shown as a continuous line in FIG. 11B). In another exemplary embodiment, the administration interface 1112 may include two or more injection needles (the additional needles shown as dashed lines in FIG. 11B). In other exemplary embodiments, the administration interface 1112 may include a needle-free pad and/or needle-free patch for performing a topical administration of a therapeutic agent.

In a packaged pre-administration state, the administration interface 1112 may be covered by an administration interface cover 1113, which may be removed by a patient before administration of the therapeutic agent. In an administration state, the administration interface 1112 may be uncovered. In an exemplary embodiment, removal of the adhesive layer 1104 may also remove the administration interface cover 1113.

The administration interface button 1110 also includes a septum 1111 that prevents the piercing needle 1108 from establishing fluid communication with the fluid conduit in the administration interface button 1110. A cover 1115 may be provided to cover the septum 1111 in a pre-administration state, which may be removed by a patient before administration. In an exemplary embodiment, the septum cover 1115 and the piercing needle cover 1105 may be coupled so that removal of one also removes the other.

In an exemplary embodiment, in a pre and post-administration state, the piercing needle cover 1105 may cover the piercing needle 1108 and the administration interface button 1110 may be in a vertically raised position as displaced by the piercing needle cover 1105 such that the administration interface 1112 is retracted within the housing 1102. In this state, the septum 1111 of the administration interface button 1110 may be disposed vertically above the piercing needle 1108. In addition, the syringe 1106 may be in a retracted position along the longitudinal axis of the assembly 1106 spaced from the septum 1111 of the administration interface button 1110.

When the piercing needle cover 1105 is removed from the piercing needle 1108, the administration interface button 1110 is lowered to a vertically lowered position such that the administration interface 1112 protrudes outside the housing 1102 at the administration site. In an exemplary embodiment, the administration interface button 1110 may be automatically lowered by the removal of the piercing needle cover 1105. In another exemplary embodiment, the administration interface button 1110 may be lowered by the patient pushing downward on the administration interface button 1110.

In an exemplary embodiment, the lowering of the administration interface button 1110 aligns the piercing needle 1108 with the septum 1111 of the administration interface button 1110. The lowering of the administration interface button 1110 also triggers a syringe actuator that advances the syringe 1106 along its longitudinal axis toward the septum 1111 of the administration interface button 1110. This causes the piercing needle 1108 to pierce the septum 1111 and establish fluid communication with the administration interface 1112.

Figure 12A:
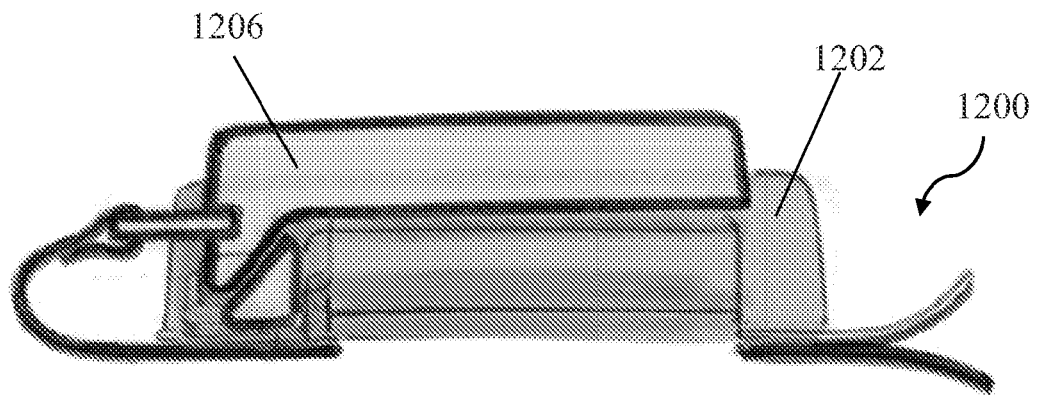
FIG. 12A illustrates a side view of an exemplary wearable automatic injection device.
Figure 12B:
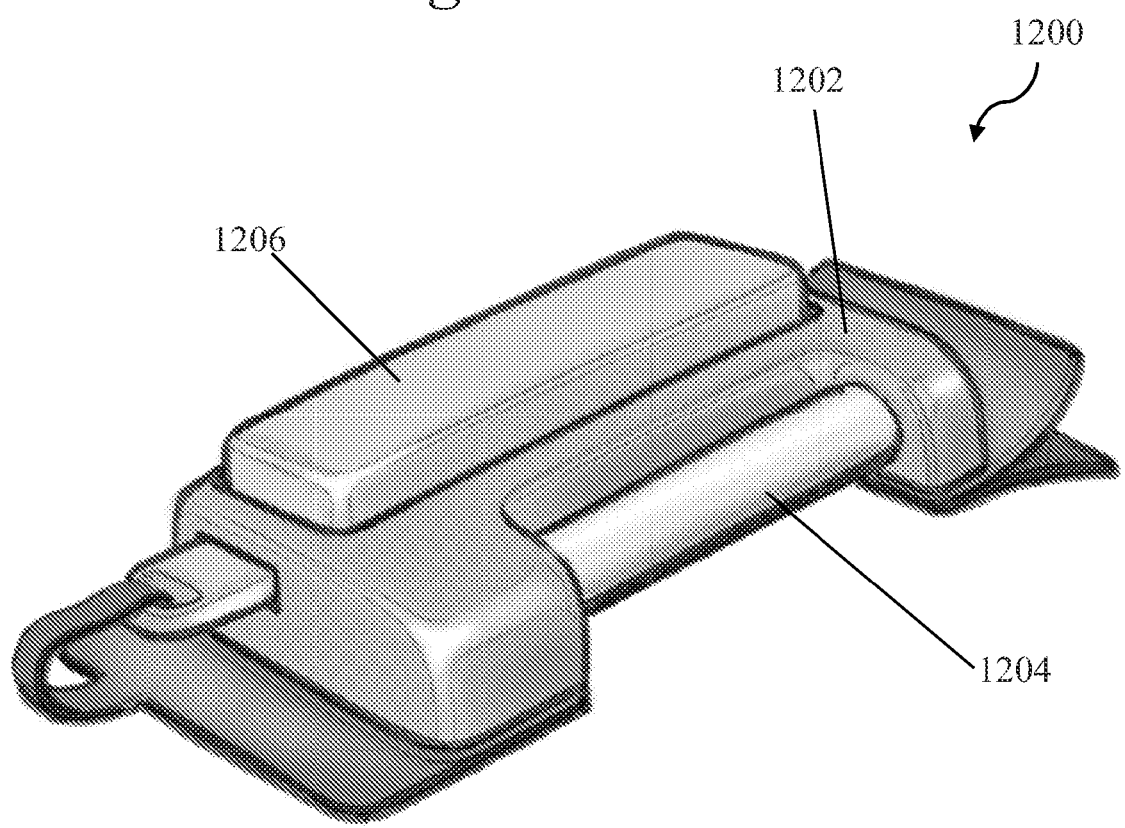
FIG. 12B illustrates a perspective view showing the components of the device of FIG. 12A.

FIGS. 12A and 12B illustrate an exemplary wearable automatic injection device. FIG. 12A illustrates a side view of the device. FIG. 12B illustrates a perspective view showing the components of the device. The automatic injection device 1200 includes a housing 1202 holding a syringe 1204 in a stationary or moveable manner relative to the housing 1202. An administration interface button 1206 is provided in the housing 1202 in the vicinity of the syringe 1204 and holds an administration interface (not pictured). The housing 1202 includes an adhesive layer 1208 for attachment at or near an administration site.

Other components in the device 1200 similar to the components in the device 1200 are described with reference to FIGS. 11A and 11B.

Figure 13A:
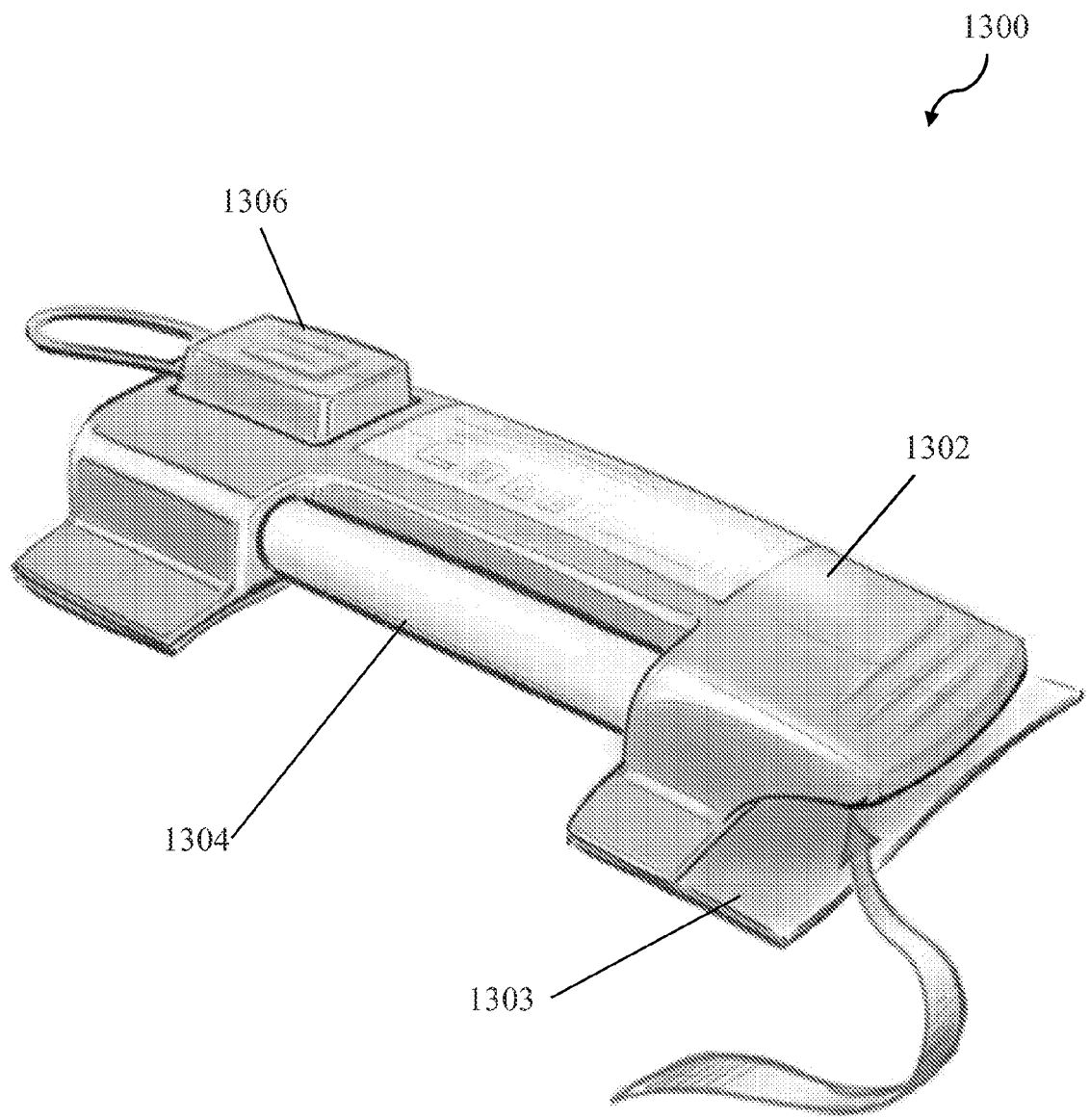
FIG. 13A illustrates a perspective view of an exemplary wearable automatic injection device.
Figure 13B:
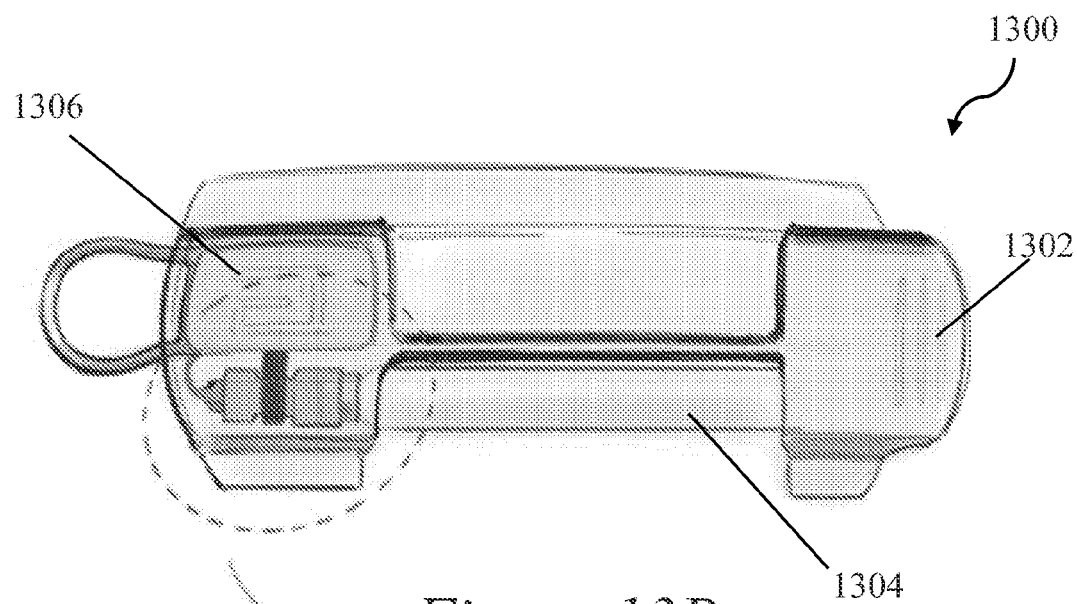
FIG. 13B illustrates a top view of the device of FIG. 13A.
Figure 13C:
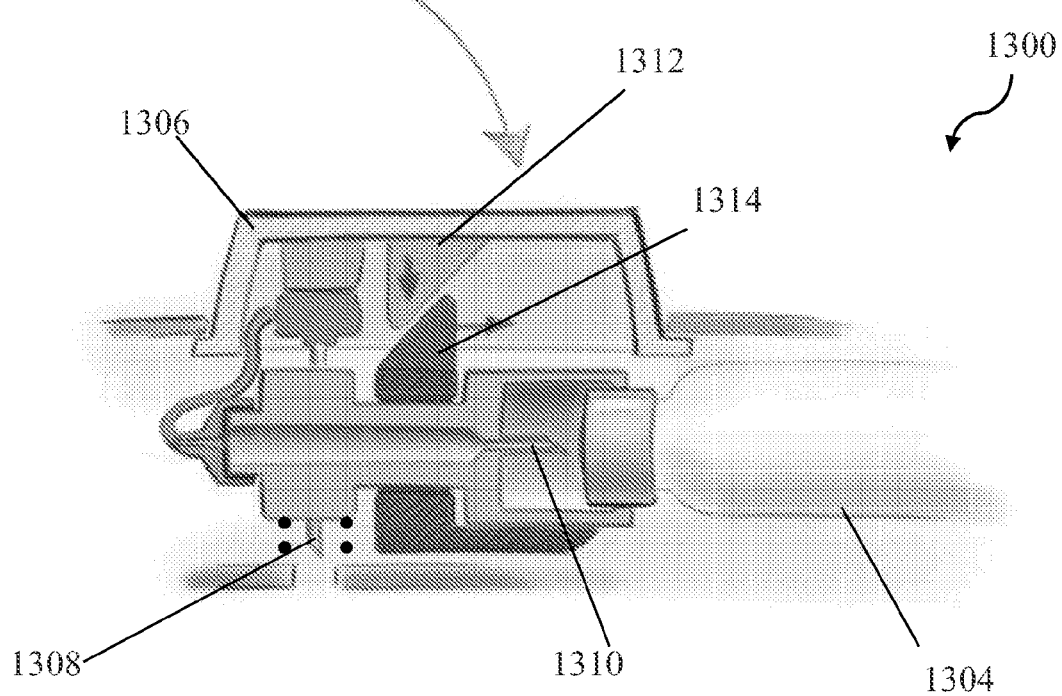
FIG. 13C illustrates a sectional side view of the transfer mechanism of the device of FIG. 13A.

FIGS. 13A-13C illustrate an exemplary wearable automatic injection device. FIG. 13A illustrates a perspective view of the device. FIG. 13B illustrates a top view of the device. FIG. 13C illustrates a side view of the transfer mechanism of the device. The automatic injection device 1300 includes a housing 1302 having an adhesive layer 1303 for attachment at or near an administration site. The housing 1302 holds a cartridge 1304 in a stationary or moveable manner relative to the housing 1302. The cartridge 1304 is configured to hold a dose of a therapeutic agent.

An administration interface button 1306 is provided in the housing 1302 in the vicinity of the cartridge 1304. The administration interface button 1306 may hold or be coupled to one or more administration interfaces 1308 that are configured to administer a therapeutic agent on, in or through the skin to any desired depth. The administration interface 1308 may extend substantially at 90 degrees relative to the longitudinal axis of the cartridge 1304, and a piercing needle 1310 may extend substantially parallel to the longitudinal axis of the cartridge 1304. In an exemplary embodiment, the administration interface 1308 may include a single injection needle (shown as a continuous line in FIG. 13C). In another exemplary embodiment, the administration interface 1308 may include two or more injection needles (the additional needles shown as dashed lines in FIG. 13C). In other exemplary embodiments, the administration interface 1308 may include a needle-free pad and/or needle-free patch for performing a topical administration of a therapeutic agent. The administration interface button 1306 may form or include a transfer mechanism that establishes fluid communication between the cartridge 1304 to the administration interface 1308 through the piercing needle 1310.

The administration interface button 1306 may include a housing engagement portion 1312 that engages with a housing portion 1314 of the housing 1302 when the administration interface button 1306 is pressed down during administration in an administration state. In an exemplary embodiment illustrated in FIG. 13C, the engagement between the housing engagement portion 1312 and the housing portion 1314 causes the housing portion 1314 to move parallel to the longitudinal axis of the cartridge 1304 toward the distal end of the cartridge 1304, thus allowing the piercing needle 1310 to establish fluid communication with the barrel portion of the cartridge 1304. In another exemplary embodiment, the engagement between the housing engagement portion 1312 and the housing portion 1314 causes the cartridge 1304 to move parallel to the longitudinal axis of the cartridge 1304 toward the piercing needle 1310, thus allowing the piercing needle 1310 to establish fluid communication with the barrel portion of the cartridge 2004. In another exemplary embodiment, the engagement between the housing engagement portion 1312 and the housing portion 1314 causes the cartridge 1304 and the administration interface button 1306 to move toward each other, thus allowing the piercing needle 1310 to establish fluid communication with the barrel portion of the cartridge 2004.

Other components in the device 1300 similar to the components in the device 1100 are described with reference to FIGS. 11A and 11B.

Figure 14A:
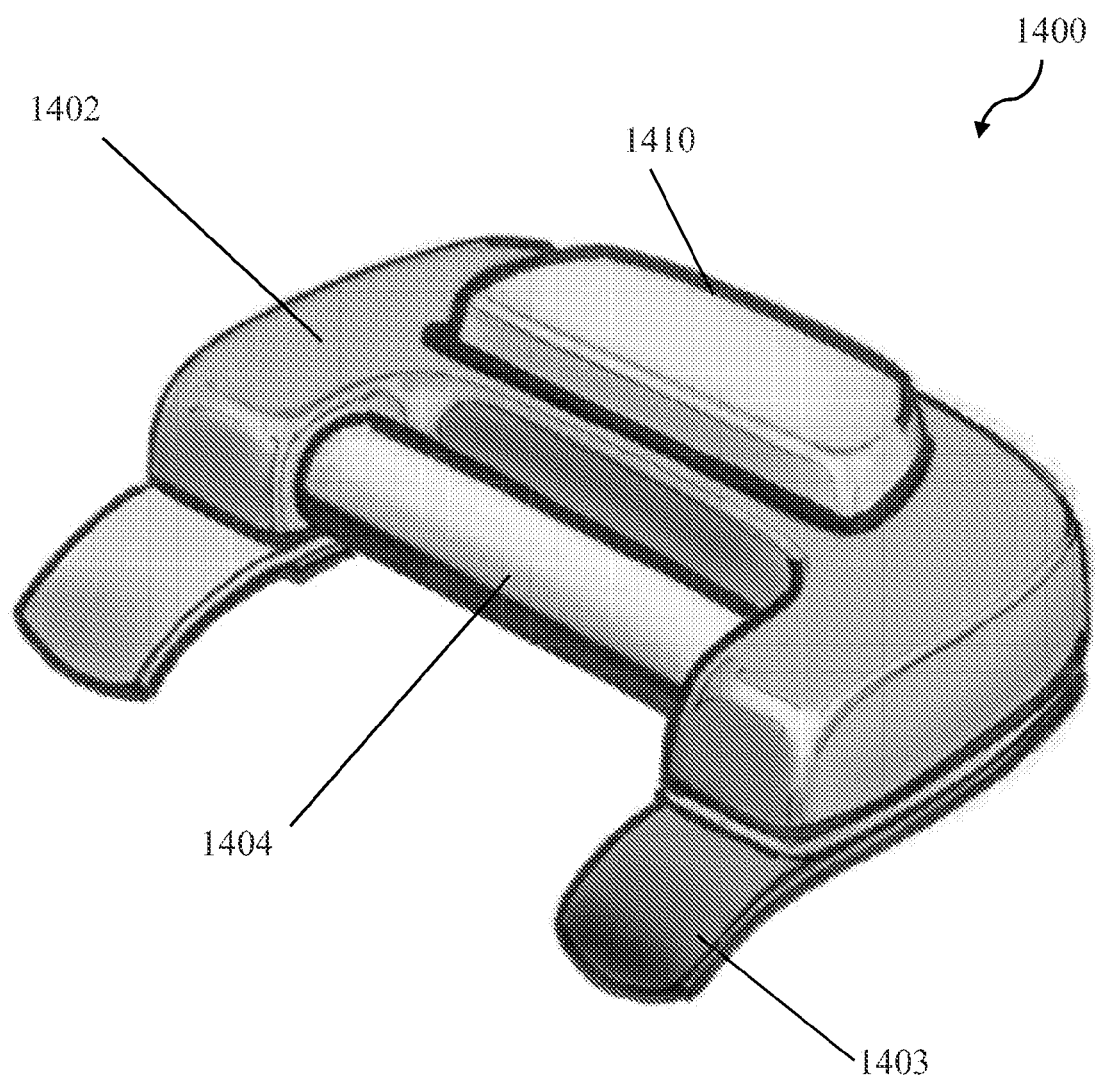
FIG. 14A illustrates a perspective view of an exemplary wearable automatic injection device including an exemplary cartridge assembly.
Figure 14B:
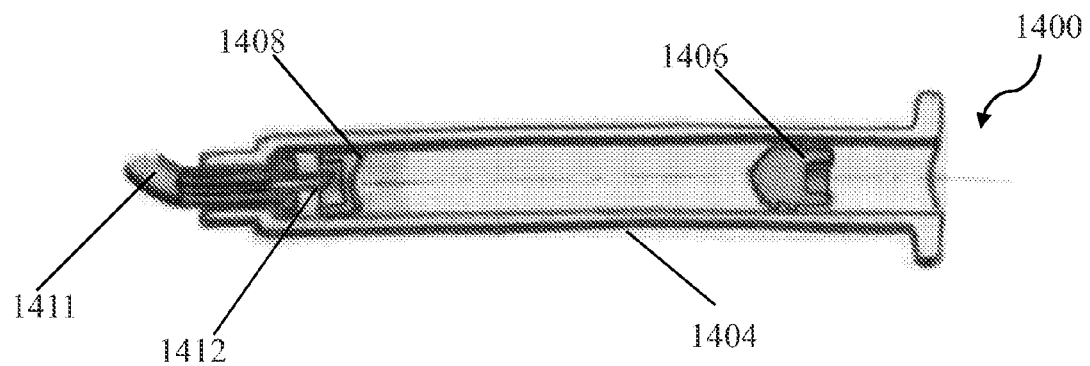
FIG. 14B illustrates a sectional side view of the exemplary cartridge assembly of FIG. 14A taken along the longitudinal axis.
Figure 14C:
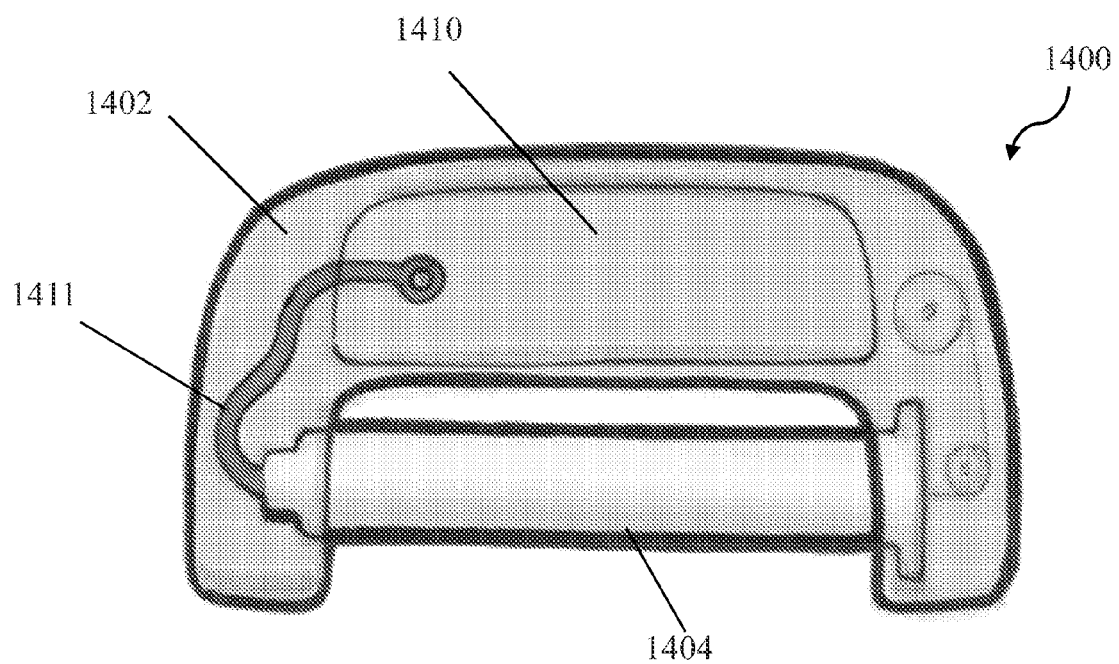
FIG. 14C illustrates a transparent top view of the device of FIG. 14A.

FIGS. 14A-14C illustrate an exemplary wearable automatic injection device including an exemplary cartridge assembly. FIG. 14A illustrates a perspective view of the device. FIG. 14B illustrates a sectional side view of the cartridge assembly taken along a longitudinal axis. FIG. 14C illustrates a transparent top view of the device. The automatic injection device 1400 includes a housing 1402 having an adhesive layer 1403 for attachment at or near an administration site. The housing 1402 holds a cartridge 1404 in a stationary or moveable manner relative to the housing 1402. The cartridge 1404 is configured to hold a dose of a therapeutic agent. A proximal end of the cartridge 1404 includes a bung 1406 and a distal end of the cartridge 1404 includes a septum 1408 that cooperatively seal the dose within the cartridge 1404.

An administration interface button 1410 is provided in the housing 1402 in the vicinity of the cartridge 1404. The administration interface button 1410 holds an administration interface at a distal end that extends substantially at 90 degrees relative to the longitudinal axis of the cartridge 1404. The administration interface button 1410 is coupled to a transfer mechanism 1411 that holds a piercing needle 1412 in the vicinity of the cartridge 1404. The piercing needle 1412 extends substantially parallel to the longitudinal axis of the cartridge 1404. The transfer mechanism 1411 includes a fluid conduit to establish fluid communication between the cartridge 1404 and the administration interface through the piercing needle 1412. In a pre-administration state, the piercing needle 1412 may extend partly into a distal end of the cartridge 1404 but may be spaced from the septum 1408. In an administration state, the bung 1406 may be moved within the cartridge 1404 such that the fluid pressure in the cartridge 1404 moves the septum 1408 forward toward the piercing needle 1412. This causes the piercing needle 1412 to pierce the septum 1408 and establishes fluid communication between the cartridge 1404 and the administration interface through the piercing needle 1412.

Other components in the device 1400 similar to the components in the device 1100 are described with reference to FIGS. 11A and 11B.

III. Exemplary Administration Systems

Exemplary embodiments provide different exemplary administration systems and assemblies for administering a dose of a therapeutic agent to a patient. In some exemplary embodiments, an administration interface—coupled to a barrel portion of an exemplary automatic injection device containing the dose—may be inserted into or applied to the patient's body to administer the dose to the patient. In other exemplary embodiments, a piercing needle may be coupled to a barrel portion containing the dose to conduct the dose out of the barrel portion, and an administration interface coupled to the piercing needle may be inserted into or applied to the patient's body to administer the dose to the patient.

Figure 15:
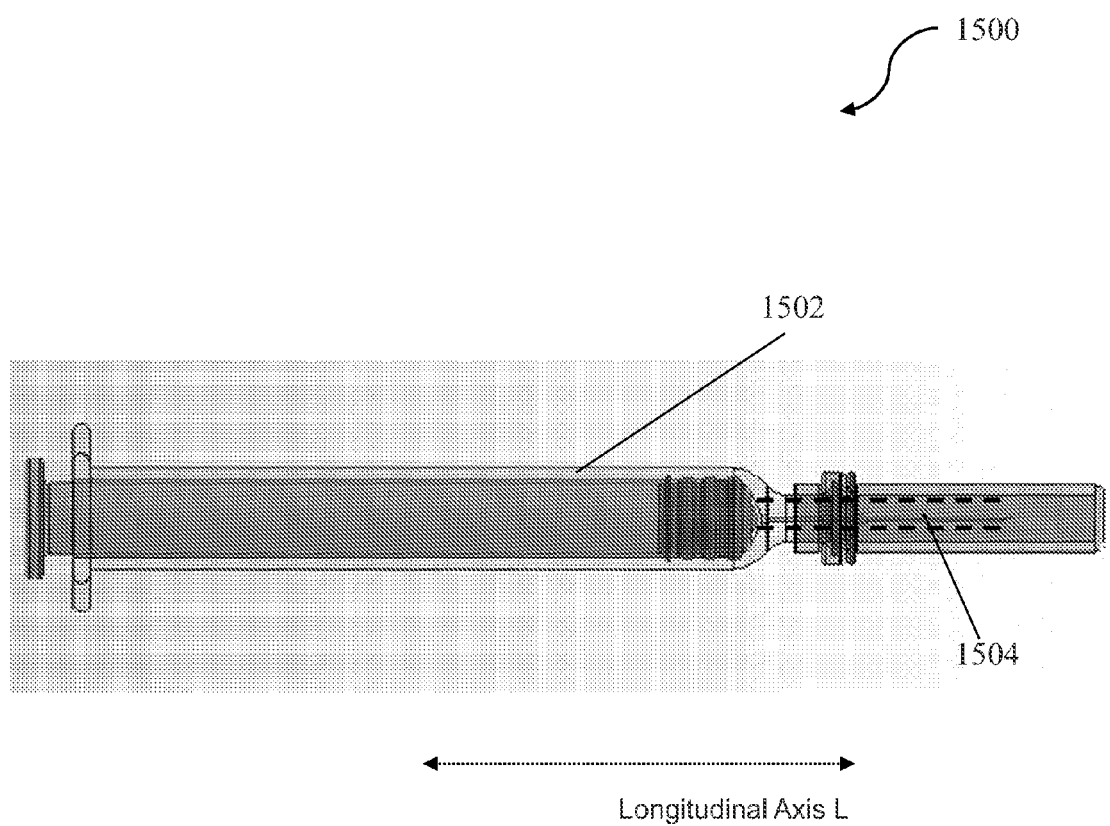
FIG. 15 illustrates an exemplary barrel portion in which a distal end of the barrel portion bears an administration interface that extends substantially along the longitudinal axis of the barrel portion.
Figure 16:
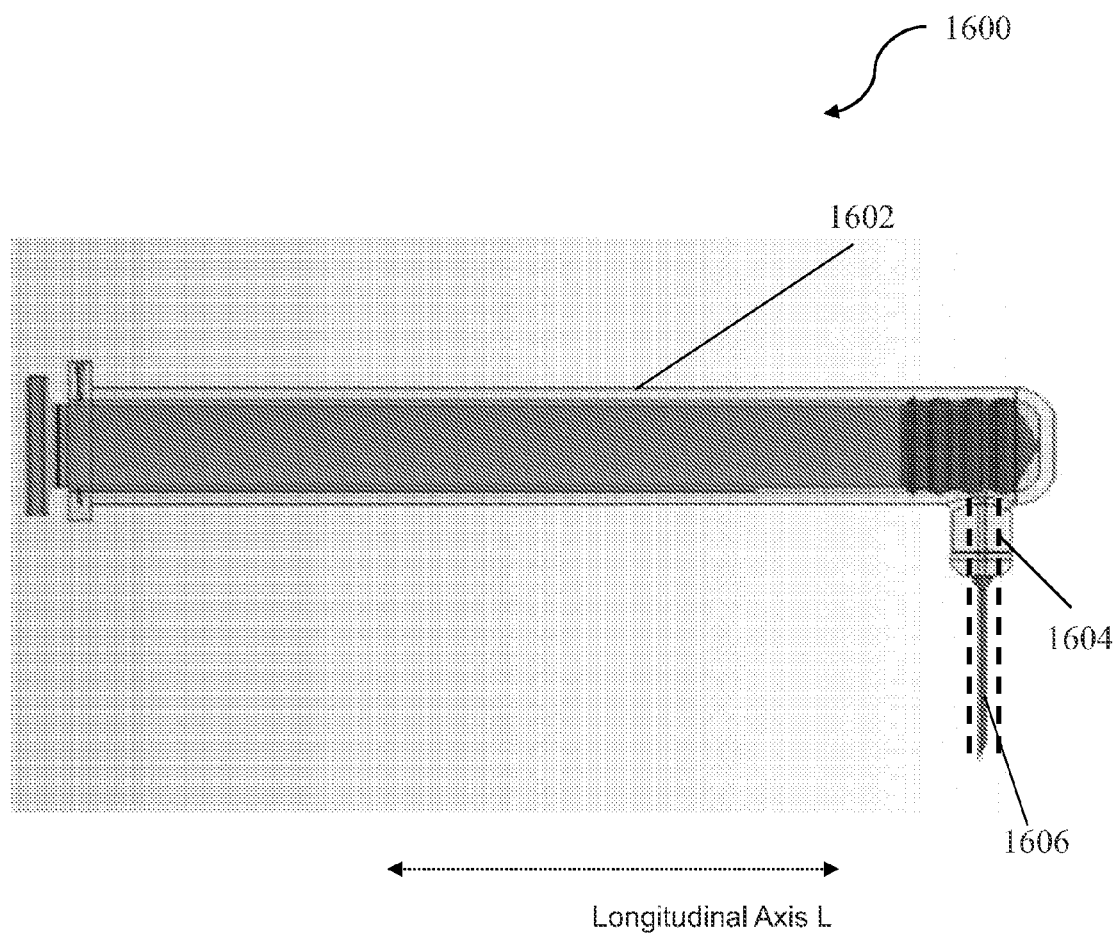
FIG. 16 illustrates an exemplary barrel portion in which a distal end of the barrel portion bears an administration interface that extends at about 90 degrees relative to the longitudinal axis of the barrel portion.

In some exemplary embodiments, as illustrated in FIGS. 15 and 16, a syringe may include a barrel portion and an administration interface coupled to a distal end of the barrel portion. The administration interface may interface with the patient's body, e.g., by insertion into or application to the patient, to administer a therapeutic agent contained in the barrel portion of the syringe. The administration interface may be aligned at any suitable angle relative to the longitudinal axis of the barrel portion ranging from about 0 degrees to about 180 degrees, but is not limited to this exemplary range.

FIG. 15 illustrates an exemplary syringe 1500 suitable for use in an exemplary automatic injection device. The syringe 1500 includes a barrel portion 1502 configured to hold a dose of a therapeutic agent and extending between a proximal end and a distal end along a longitudinal axis L. A distal end of the barrel portion 1502 is coupled to one or more administration interfaces 1504 that extend along the longitudinal axis L. In an exemplary embodiment, the administration interface 1504 may include a single injection needle (shown as a continuous line in FIG. 15). In another exemplary embodiment, the administration interface 1504 may include two or more injection needles (the additional needles shown as dashed lines in FIG. 15). In other exemplary embodiments, the administration interface 1504 may include a needle-free pad and/or a needle-free patch for performing a topical administration of a therapeutic agent.

FIG. 16 illustrates an exemplary syringe 1600 suitable for use in an exemplary automatic injection device. The syringe 1600 includes a barrel portion 1602 configured to hold a dose of a therapeutic agent and extending between a proximal end and a distal end along a longitudinal axis L. A distal end of the barrel portion 1602 may include an elbow portion 1604 that extends substantially at 90 degrees from the longitudinal axis L. A distal end of the elbow portion 1604 is coupled to an administration interface 1606 that extends substantially at 90 degrees from the longitudinal axis L. The administration interface 1606 may be configured to administer a therapeutic agent on, in or through the skin to any desired depth. One of ordinary skill in the art will recognize that exemplary automatic injection devices may include administration interfaces that extend along the longitudinal axis L of the syringe or that extend at any suitable angle relative to the longitudinal axis L of the syringe. Exemplary angles may include, but are not limited to, about 70 degrees to about 110 degrees. In an exemplary embodiment, the administration interface 1606 may include a single injection needle (shown as a continuous line in FIG. 16). In another exemplary embodiment, the administration interface 1606 may include two or more injection needles (the additional needles shown as dashed lines in FIG. 16). In other exemplary embodiments, the administration interface 1606 may include a needle-free pad and/or a needle-free patch for performing a topical administration of a therapeutic agent.

Figure 17:
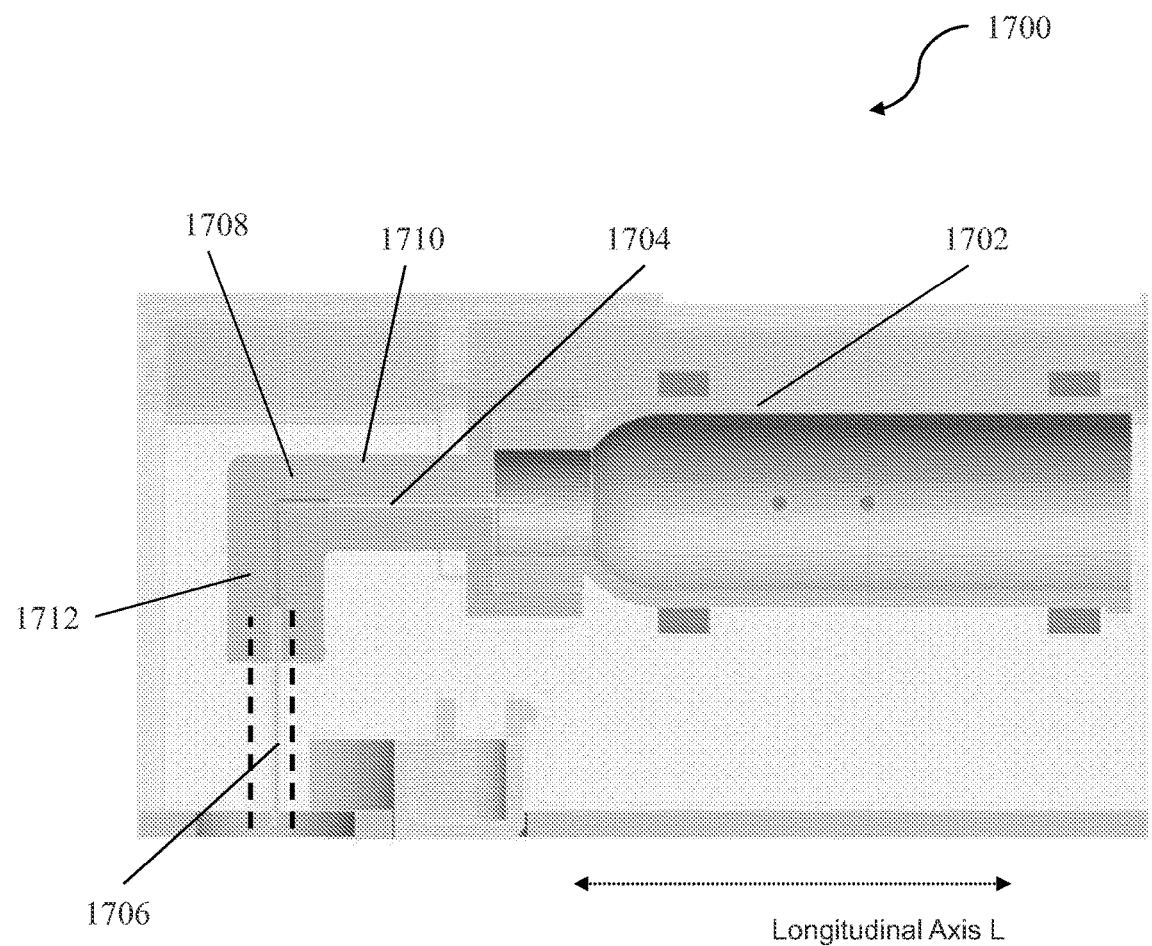
FIG. 17 illustrates an exemplary assembly in which an exemplary adapter couples a piercing needle to an administration interface.
Figure 18:
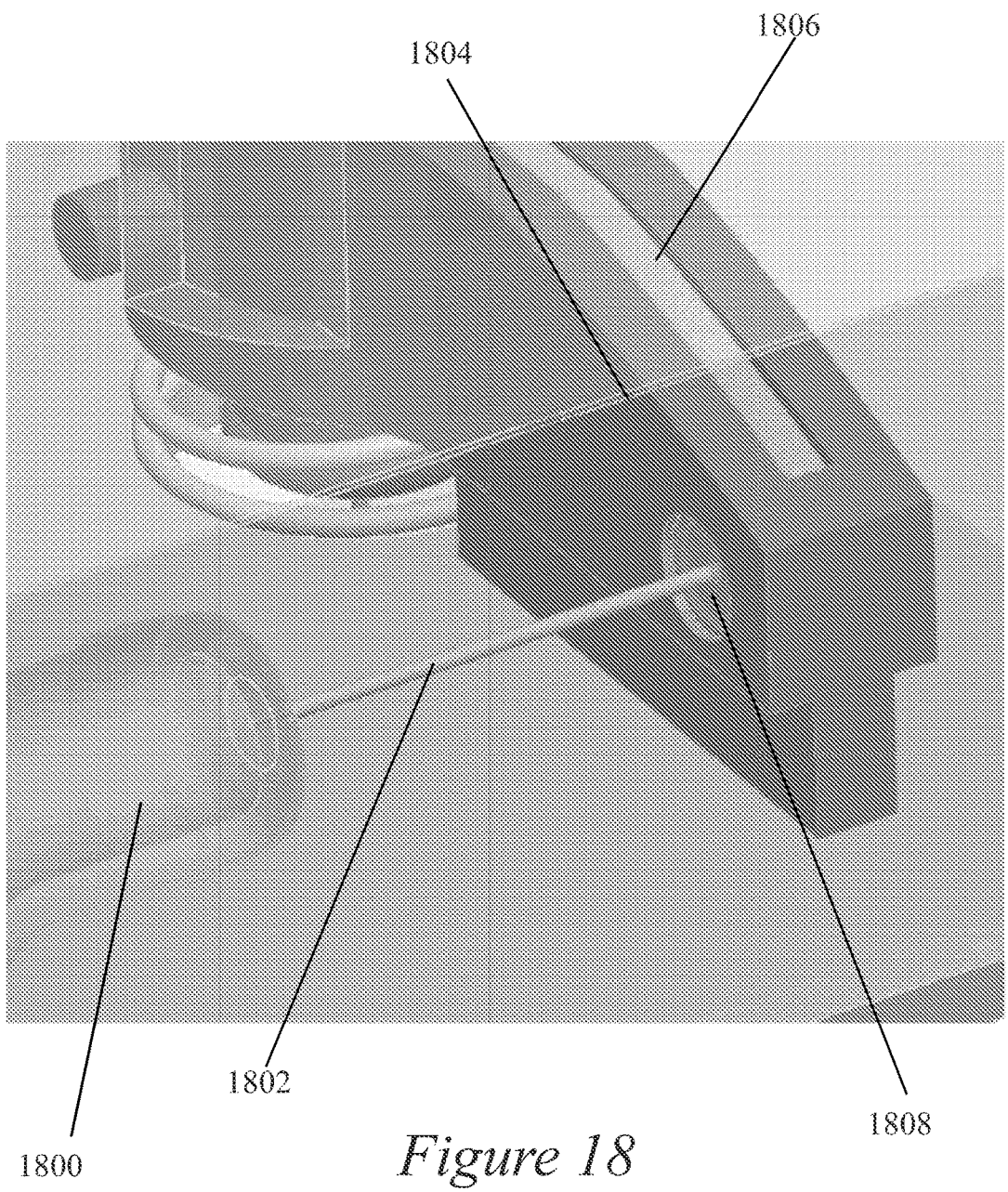
FIG. 18 illustrates an exemplary assembly in which a fluid conduit couples a piercing needle to an administration interface.

In some exemplary embodiments, as illustrated in FIGS. 17 and 18, a syringe may include a barrel portion and an administration interface coupled to a distal end of the barrel portion. The administration interface may interface with the patient's body, e.g., by insertion into or application to the patient's body, to administer a therapeutic agent contained in the barrel portion of the syringe. The administration interface may be aligned at any suitable angle relative to the longitudinal axis of the barrel portion ranging from about 0 degrees to about 180 degrees, but is not limited to this exemplary range.

In some exemplary embodiments, as illustrated in FIGS. 17 and 18, a syringe may include a barrel portion and an administration interface coupled directly or indirectly to a distal end of the barrel portion. The piercing needle may convey a therapeutic agent contained in the barrel portion of the syringe to the administration interface, and the administration interface may administer the therapeutic agent to a patient. A coupling between the piercing needle and the administration interface may be provided by one or more intermediate components. An exemplary coupling component may include, for example, an adapter, provided between the distal end of the barrel portion and the administration interface.

FIG. 17 illustrates an exemplary syringe 1700 suitable for use in an exemplary automatic injection device. The syringe 1700 includes a barrel portion 1702 configured to extend from a proximal end to a distal end along a longitudinal axis L and configured to hold a dose of a therapeutic agent. A distal end of the barrel portion 1702 is coupled to a piercing needle 1704. The piercing needle 1704 is, in turn, coupled to one or more administration interfaces 1706 through an exemplary intermediate adapter 1708. The administration interface 1706 may be configured to administer a therapeutic agent on, in or through the skin to any desired depth. More specifically, a proximal portion of the adapter 1708 is coupled to the piercing needle 1704 and a distal portion of the adapter 1708 is coupled to the administration interface 1706. The adapter 1708 may establish a substantially 90 degree alignment between the longitudinal axis L of the barrel portion 1702 and the administration interface 1706. In an exemplary embodiment, the administration interface 1706 may include a single injection needle (shown as a continuous line in FIG. 17). In another exemplary embodiment, the administration interface 1706 may include two or more injection needles (the additional needles shown as dashed lines in FIG. 17). In other exemplary embodiments, the administration interface 1706 may include a needle-free pad and/or a needle-free patch for performing a topical administration of a therapeutic agent.

The exemplary adapter 1708 is a component that includes a first portion 1710 that extends from the barrel portion 1702 substantially parallel to the longitudinal axis L, and a second portion 1712 that extends from the first portion 1710 substantially perpendicular to the longitudinal axis L. More specifically, a proximal end of the first portion 1710 is coupled to a distal end of the barrel portion 1702. In an exemplary embodiment, the proximal end of the first portion 1710 may envelope the distal end of the barrel portion 1702. A distal end of the first portion 1710 is coupled to a proximal end of the second portion 1712. A distal end of the second portion 1712 is coupled to a proximal end of the administration interface 1706. In an exemplary embodiment, the first portion 1710 and the second portion 1712 of the adapter 1708 may be formed integrally.

Exemplary adapters may be formed of a rigid material including, but not limited to, plastic materials, steel, and the like. Exemplary adapters may alternatively be formed of a flexible material including, but not limited to, rubber and the like.

The configuration of the adapter 1708 coupled to the administration interface 1706 allows the administration interface 1706 to extend at about 90 degrees relative to the longitudinal axis L of the syringe. This configuration simplifies the manufacturing of the wearable automatic injection device as it eliminates the need for a bent administration interface. The exemplary administration interface 1706 maintains a low profile against the patient while allowing for proper insertion into or application to the patient's body. One of ordinary skill in the art will recognize that exemplary administration interfaces may be bent from the longitudinal axis of the syringe to any suitable angle not limited to about 90 degrees, for example, about 70 degrees to about 110 degrees.

In some exemplary embodiments, one or more fluid conduits may be disposed between the piercing needle and the administration interface to allow a flow of the therapeutic agent from the barrel portion to the administration needle through the piercing needle. Any suitable fluid conduit or fluid transfer mechanism may be used to establish the one or more fluid conduits between the piercing needle and the administration interface. In an exemplary embodiment, a pierceable septum in its intact state may separate the piercing needle from fluid communication from the administration interface. When the piercing needle pierces the septum during administration in an administration state, fluid communication may be established between the piercing needle and the administration interface through the fluid conduit.

FIG. 18 illustrates a portion of an exemplary automatic injection device in which a fluid conduit within a transfer mechanism couples a piercing needle and an administration interface. The device includes a syringe or cartridge assembly having a barrel portion 1800 holding a dose of a therapeutic agent. A distal end of the barrel portion 1800 is coupled to a piercing needle 1802. A transfer mechanism 1804 is provided in contact with or in the vicinity of the piercing needle 1802, and also in contact with or in the vicinity of an administration interface (not pictured). The transfer mechanism 1804 includes a fluid conduit or passageway 1806 that establishes fluid communication between the piercing needle 1802 and the administration interface. In another exemplary embodiment, the piercing needle and the administration interface may be coupled directly without an intervening transfer mechanism.

In an exemplary embodiment, the transfer mechanism 1804 includes a pierceable septum 1808 that separates the piercing needle 1802 from the fluid conduit 1806 in the transfer mechanism 1804 before administration in a pre-administration state. In an exemplary embodiment, during administration in an administration state, the syringe or cartridge may be moved toward the transfer mechanism 1804 so that the piercing needle 1802 pierces the septum 1808 to create a fluid communication path among the barrel portion 1800, the fluid conduit 1806 of the transfer mechanism 1804, and the administration interface. The therapeutic agent may thereby flow out of the barrel portion 1800 through the piercing needle 1802 into the fluid conduit 1806. The therapeutic agent may then be transmitted through the fluid conduit 1806 into the administration interface for administration of the therapeutic agent to a patient.

Figure 19:
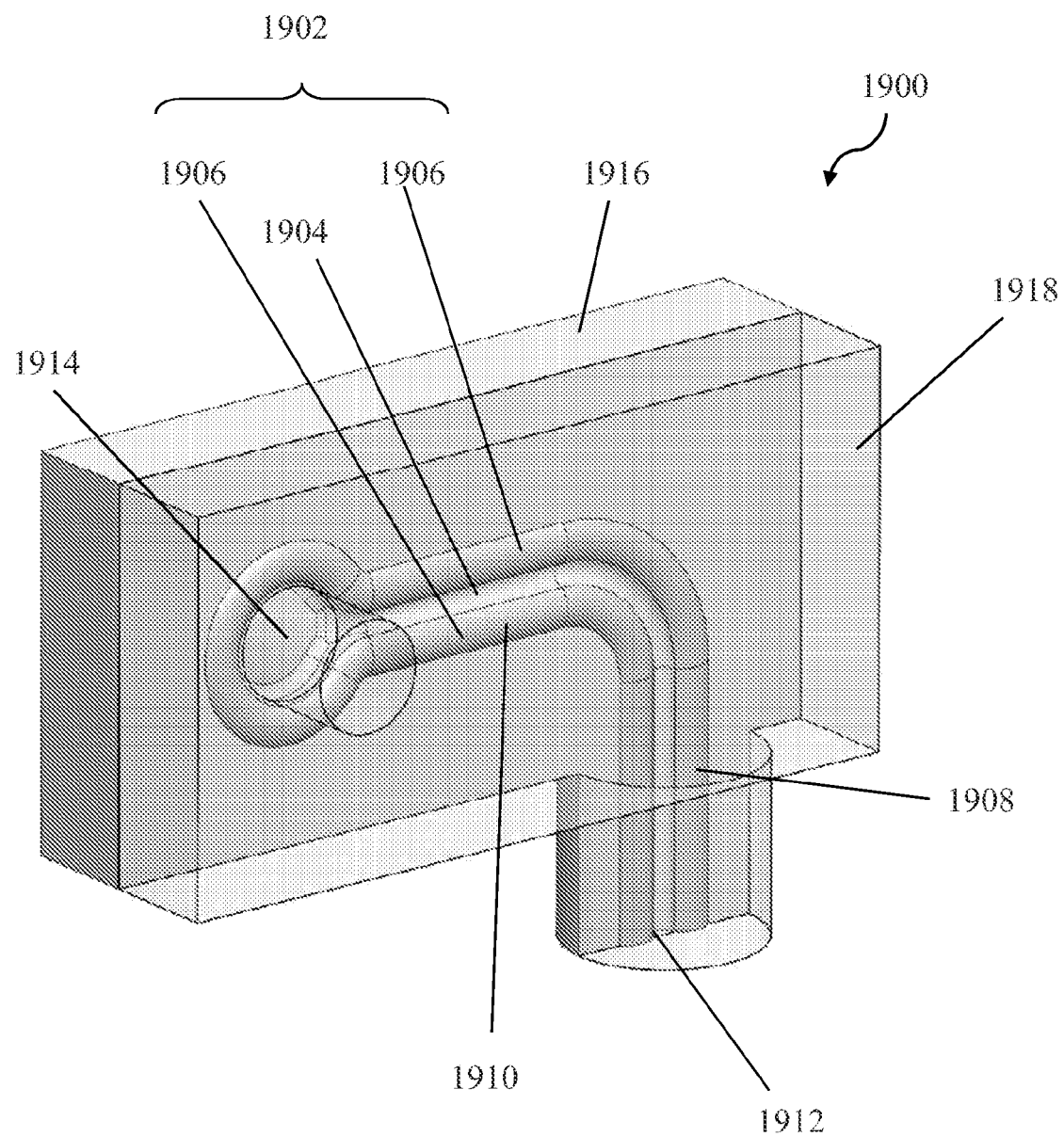
FIG. 19 illustrates an exemplary transfer mechanism for providing a fluid conduit between a piercing needle and an administration interface.

FIG. 19 illustrates an exemplary transfer mechanism 1900 for providing a fluid conduit 1902 between a piercing needle (not pictured) and an administration interface (not pictured). The fluid conduit 1902 may include a centrally extending channel 1904 through which the therapeutic agent flows from the piercing needle to the administration interface, and raised wall portions 1906 extending along the edges of the channel 1904 in order to constrain the fluid to the channel 1904. The fluid conduit 1902 may take any suitable form and dimension. In the illustrative embodiment, the fluid conduit 1902 has a first substantially straight portion 1908 aligned at about 90 degrees from a second substantially straight portion 1910.

The fluid conduit 1902 may include a fluid inlet 1912 for entry of the therapeutic agent from the piercing needle, and a fluid outlet 1914 for exit of the therapeutic agent into the administration interface. The fluid inlet 1912 may be coupled directly or indirectly to the distal end of a piercing needle. In an exemplary embodiment, a pierceable septum (not pictured) may be provided at the fluid inlet 1912 to prevent fluid flow from the piercing needle when the septum is intact, and to allow fluid flow from the piercing needle when the septum is pierced by the piercing needle. The fluid outlet 1914 may be coupled directly or indirectly to the proximal end of the administration interface in order to establish a fluid flow path between the fluid conduit 1902 and the administration interface.

Alternatively, 1912 may be used as the fluid outlet and 1914 may be used as the fluid inlet. In this exemplary embodiment, the fluid inlet 1914 may be coupled directly or indirectly to a piercing needle, and the fluid outlet 1912 may be coupled directly or indirectly to an administration interface.

The transfer mechanism 1900 may be formed of two housing portions 1916 and 1918 stacked together. In an exemplary embodiment, the fluid conduit 1902 may be formed on the surface of portion 1916, and portion 1918 may be stacked over the fluid conduit 1902 so as to seal the edges of the fluid conduit 1902 in order to prevent fluid leakage from the fluid conduit. Compression between the two housing portions 1916 and 1918 may be provided by one or more mechanical interlocking mechanism, for example, one or more fasteners, snaps, chemical bonding, ultrasonic welding, and others.

The fluid conduit 1902 may be formed on the surface of the housing portion 1916 using any suitable technology. In an exemplary embodiment, the raised wall portions 1906 of the fluid conduit 1902 may be formed of a low durometer material molded as a gasket to seal the flow path of the therapeutic agent. In another exemplary embodiment, laser welding may be used to trace a path around the perimeter of the channel 1904 in order to simultaneously create a seal around the channel 1904 and bond the two housing portions 1916 and 1918 together.

In another exemplary embodiment, the piercing needle and the administration interface may be coupled directly without an intervening transfer mechanism.

Figure 20:
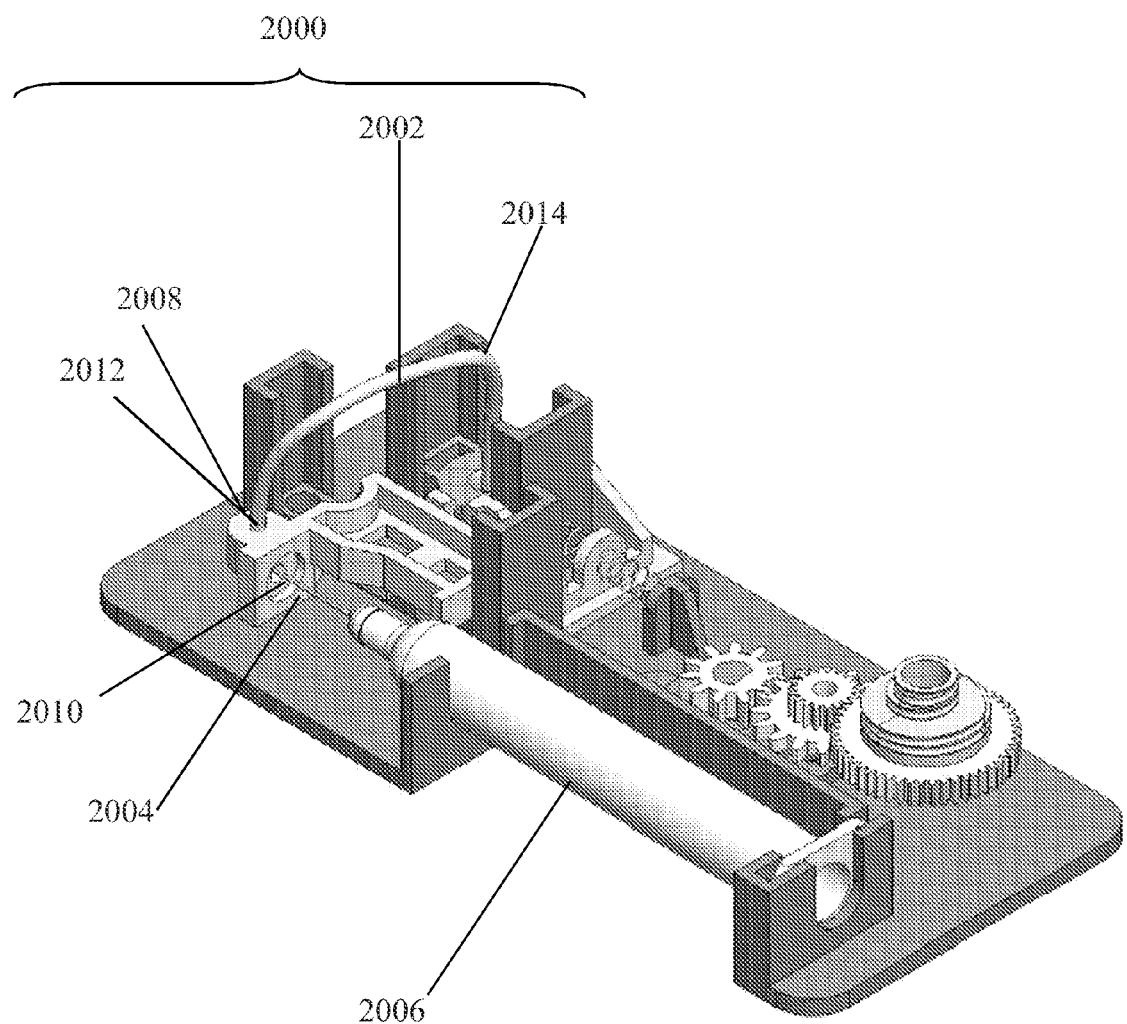
FIG. 20 illustrates an exemplary transfer mechanism for providing a fluid conduit between a piercing needle and an administration interface.

FIG. 20 illustrates an exemplary transfer mechanism 2000 for providing a fluid conduit 2002 between a syringe with a piercing needle 2004 coupled to a barrel portion 2006 and an administration interface (not pictured). The transfer mechanism 2000 may include a first portion 2008 having a septum 2010 provided in the vicinity of the piercing needle 2004.

The first portion 2008 of the transfer mechanism 2000 may include an internal hollow space for accommodating the therapeutic agent and an inlet port 2012 coupled to one end of a hollow tube 2014. Another end of the hollow tube 2014 is coupled directly or indirectly (for example, through a second portion similar to first portion 2008) to the administration interface. The hollow tube 2014 provides a fluid path from the piercing needle 2004 to the administration interface. The hollow tube 2014 may take any suitable form, alignment and dimension. In the illustrative embodiment, the hollow tube 2014 extends substantially at right angles to the longitudinal axis of the barrel portion 2006.

In an exemplary embodiment, the transfer mechanism 2000 may be moveable upward and/or downward along the vertical axis. In this embodiment, before administration in a pre-administration state (for example, when the piercing needle is covered by a needle cover), the transfer mechanism 2000 may be in a vertically raised position above the piercing needle 2004 such that the piercing needle 2004 is not aligned with the septum 2010 in the transfer mechanism 2000, thereby preventing fluid communication between the piercing needle 2004 and the transfer mechanism 2000. At the beginning of administration (for example, upon removal of the syringe cover from the piercing needle 2004), the transfer mechanism 2000 may be automatically lowered to a vertically lowered position such that the piercing needle 2004 becomes aligned with the septum 2010 in the transfer mechanism 2000, thus allowing the piercing needle 2004 to pierce the septum 2010. Exemplary embodiments may provide any suitable actuation mechanism for lowering the transfer mechanism 2000 from the vertically raised position to the vertically lowered position at the beginning of administration.

In an exemplary embodiment, the piercing needle 2004 may be initially coupled to or provided immediately adjacent to the first portion 2008. In another embodiment, the syringe may be in a retraction position within the wearable automatic injection device and the piercing needle 2004 may be initially separated from the first portion 2008 of the transfer mechanism 2000. In this embodiment, before administration in a pre-administration state, the piercing needle 2004 may be separated from the septum 2010 in the first portion 2008 and may not be in fluid communication with the transfer mechanism 2000. At the beginning of administration, the syringe may be moved forwardly by a cartridge or syringe actuator to an extended position within the device, and the piercing needle 2004 may pierce the septum 2010, allowing the therapeutic agent to flow from the barrel portion 2006 to the transfer mechanism 2000. Exemplary embodiments may provide any suitable syringe or cartridge actuation mechanism for advancing the barrel portion and/or the cartridge assembly within the housing between the retracted position and the extended position in order to pierce the septum and convey the therapeutic agent to the patient's body through the administration interface.

An advantage of the exemplary transfer mechanism 2000 is that the motions of the piercing needle 2004 and the administration interface are decoupled and independent from each other. For example, the mechanism coupling the piercing needle 2004 to the inlet port 2012 need not take into consideration how this coupling would affect the outlet of the transfer mechanism 2000 coupled to the administration interface.

Figure 21:
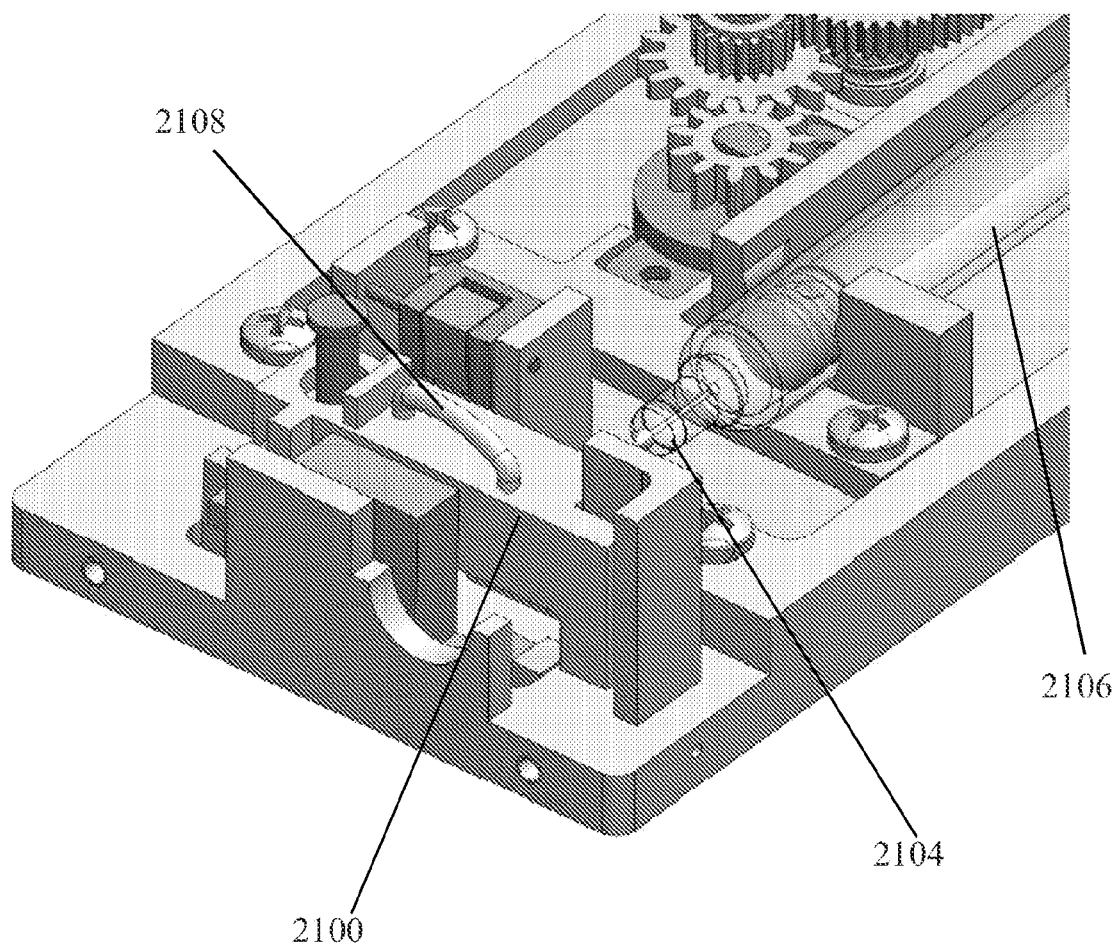
FIG. 21 illustrates an exemplary transfer mechanism for providing a fluid conduit between a piercing needle and an administration interface.

FIG. 21 illustrates an exemplary transfer mechanism 2100 for providing a fluid conduit between a syringe having a piercing needle 2104 coupled to a barrel portion 2106 and an administration interface (not pictured). The transfer mechanism 2100 may include an inlet portion (not pictured) couplable to the piercing needle 2104 and an outlet portion (not pictured) couplable to the administration interface. A hollow tube 2108, for example, a jumper tube, may be used to couple the inlet portion of the transfer mechanism to the outlet portion of the transfer mechanism. The hollow tube 2108 provides a fluid path from the piercing needle 2104 to the administration interface. The hollow tube 2108 may take any suitable form, alignment and dimension. In the illustrative embodiment, the hollow tube 2108 extends substantially at right angles to the longitudinal axis of the barrel portion 2106.

In an exemplary embodiment, the inlet portion of the transfer mechanism 2100 may include a septum (not pictured) provided in the vicinity of the piercing needle 2104. Piercing of the septum by the piercing needle 2104 may establish fluid communication between the barrel portion 2106 and the transfer mechanism 2100. In an exemplary embodiment, the outlet portion of the transfer mechanism may include a septum (not pictured) provided in the vicinity of the administration interface. Piercing of the septum by the administration interface may establish fluid communication between the transfer mechanism 2100 and the patient's body.

In an exemplary embodiment, the transfer mechanism 2100 may be moveable upward and/or downward along the vertical axis. In this embodiment, before administration in a pre-administration state (for example, when the piercing needle is covered by a needle cover), the transfer mechanism 2100 may be in a vertically raised position above the piercing needle 2104 such that the piercing needle 2104 is not aligned with the septum in the transfer mechanism 2100, thereby preventing fluid communication between the piercing needle 2104 and the transfer mechanism 2100. At the beginning of administration (for example, upon removal of the syringe cover from the piercing needle 2104), the transfer mechanism 2100 may be automatically lowered to a vertically lowered position such that the piercing needle 2104 becomes aligned with the septum in the transfer mechanism 2100, thus allowing the piercing needle 2104 to pierce the septum. Exemplary embodiments may provide any suitable actuation mechanism for lowering the transfer mechanism 2100 from the vertically raised position to the vertically lowered position at the beginning of administration.

In an exemplary embodiment, the piercing needle 2104 may be initially coupled to or provided immediately adjacent to the first portion 2108. In another embodiment, the syringe may be in a retraction position within the wearable automatic injection device and the piercing needle 2104 may be initially separated from the transfer mechanism 2100. In this embodiment, before administration in a pre-administration state, the piercing needle 2104 may be separated from the septum and may not be in fluid communication with the transfer mechanism 2100. At the beginning of administration, the syringe may be moved forwardly by a cartridge or syringe actuator to an extended position within the device, and the piercing needle 2104 may pierce the septum, allowing the therapeutic agent to flow from the barrel portion 2106 to the transfer mechanism 2100. Exemplary embodiments may provide any suitable syringe or cartridge actuation mechanism for advancing the barrel portion and/or the cartridge assembly within the housing between the retracted position and the extended position in order to pierce the septum and convey the therapeutic agent to the patient's body through the administration interface.

In another exemplary embodiment, the piercing needle and the administration interface may be coupled directly without an intervening transfer mechanism.

In the exemplary embodiments illustrated in FIGS. 17-21, a tight and reliable fluid path conveys the therapeutic agent from the barrel portion of a syringe or cartridge through a pierced septum and a tube or channel in a transfer mechanism and eventually into an administration interface. This configuration allows the piercing needle assembly and the administration interface assembly to move independently of each other, which facilitates retraction of the administration interface into the housing in a post-administration state after administration has been performed, while leaving the piercing needle in a position in which it pierces the septum.

Figure 22:
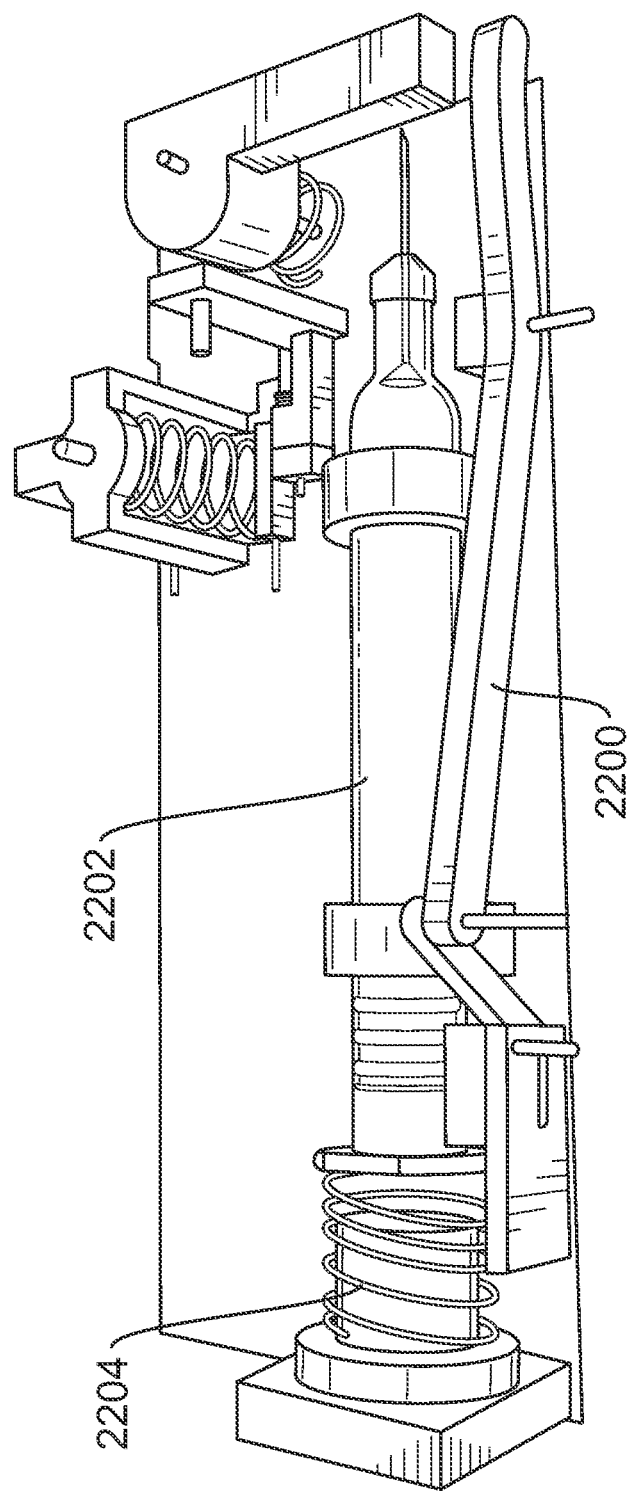
FIG. 22 illustrates an exemplary syringe or cartridge actuator that may be used to advance a syringe or cartridge assembly from a retraction position to an extended position within the housing of a wearable automatic injection device.

FIG. 22 illustrates an exemplary syringe or cartridge actuator 2200 that may be used to advance a syringe 2202 or a cartridge assembly from a retraction position to an extended position toward an administration interface within the housing of a wearable automatic injection device. A proximal end of the syringe or cartridge assembly may be coupled to a biasing member 2204, for example, a drive spring, that applies a force on the syringe or cartridge assembly to move the syringe or cartridge assembly toward a septum in a transfer mechanism (not pictured). The syringe or cartridge actuator 2200 may counter the biasing force of the biasing member, and may hold and lock the barrel portion and/or the cartridge assembly in a retracted position in a stable and reliable manner. In an exemplary embodiment in which a syringe is provided, the syringe may be coupled to a piercing needle that pierces the septum. In another exemplary embodiment in which a cartridge is provided, the transfer mechanism may be provided with a piercing needle that pierces the septum.

When triggered by a suitable trigger mechanism in an administration state, the syringe or cartridge actuator 2200 may allow the syringe or cartridge assembly to move forward toward the septum under the force of the biasing member. In an exemplary embodiment, the syringe or cartridge actuator 2200 may be configured and/or set to a certain distance to control the level of triggering force required to advance the syringe or cartridge assembly from the retracted position to the extended position.

Any suitable trigger mechanism may be used to trigger the syringe or cartridge actuation systems. In an exemplary embodiment, the trigger mechanism may automatically trigger the syringe or cartridge actuation system when the wearable automatic injection device moves from a pre-administration state to an administration state. In an exemplary embodiment, the downward vertical movement of an administration interface button within the housing to provide a fluid path between the syringe or cartridge assembly and the administration interface may provide a trigger force to trigger the plunger actuation system. In another exemplary embodiment, the forward movement of the syringe or cartridge assembly within the housing to establish a fluid path between the syringe or cartridge assembly and the administration interface may provide a trigger force to trigger the syringe or cartridge system. In another exemplary embodiment, the syringe or cartridge system may be manually triggered by a patient.

Before administration in a pre-administration state, a piercing needle cover, for example, a rigid needle cover (not pictured), provided at the distal end of the syringe 2202 may protectively cover the piercing needle. The piercing needle cover may maintain sterility of the piercing needle and a fluid conduit formed by and coupled to the piercing needle. At this stage, since the piercing needle is covered with the needle cover, the distal end of the syringe 2202 has a first greater diameter. As such, the administration interface button including the septum is maintained in a vertically raised position above the piercing needle cover, and the septum is not aligned with the piercing needle. When the piercing needle cover is removed from the syringe in preparation for administration (for example, manually by a patient or by an automatic mechanism), the administration interface button is allowed to lower to a vertically lowered position since it is not longer kept displaced by the rigid piercing needle cover, and the septum in the administration interface button is aligned with the piercing needle. The removal of the piercing needle cover thus lowers the administration interface button from its vertically raised position to its vertically lowered position. The lowering of the administration interface button, in turn, applies a trigger force to the syringe or cartridge actuator 2200 and operates as the trigger mechanism for the syringe or cartridge actuator 2200.

Figure 23:
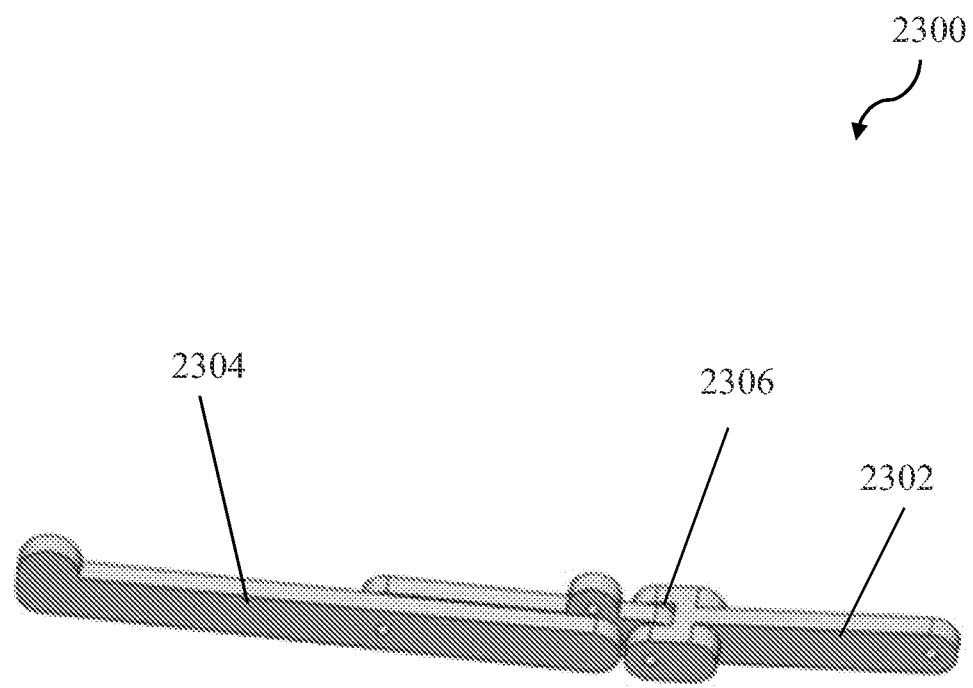
FIG. 23 illustrates an exemplary syringe or cartridge actuator including a first portion, a second portion and a hinge portion provided between the first and second portions.

FIG. 23 illustrates an exemplary syringe or cartridge actuator 2300 including a first portion 2302, a second portion 2304 and a hinge portion 2306 provided between the first and second portions. The hinge portion 2306 allows the first and second portions to rotate about the hinge relative to each other. In different rotational configurations, the first and second portions may have exemplary angles of between about 0 degrees and about 180 degrees between each other. The actuator 2300 may be coupled to the syringe and/or the administration interface button. When the septum and/or the administration interface button is in a vertically raised position, the actuator 2300 may hold the syringe in place in its retracted position. When the septum and/or the administration interface button is in a vertically lowered position, the actuator 2300 may release the syringe so that the biasing member may push the syringe forward to its extended position in order to pierce the septum.

IV. Exemplary Plunger Actuation Systems and Administration Interface Retraction Systems Exemplary embodiments provide plunger actuation systems for actuating a bung in a barrel portion of a wearable automatic injection device so that the bung moves forwardly within the barrel portion and expels a dose of a therapeutic agent contained in the barrel portion. Any suitable trigger mechanism may be used to trigger the plunger actuation systems. In an exemplary embodiment, the trigger mechanism may automatically trigger the plunger actuation system when the wearable automatic injection device moves from a pre-administration state to an administration state. In an exemplary embodiment, the downward vertical movement of an administration interface button within the housing to provide a fluid path between the syringe or cartridge assembly and the administration interface may provide a trigger force to trigger the plunger actuation system. In another exemplary embodiment, the forward movement of the syringe or cartridge assembly within the housing to establish a fluid path between the syringe or cartridge assembly and the administration interface may provide a trigger force to trigger the plunger actuation system. In another exemplary embodiment, the plunger actuation system may be manually triggered by a patient.

Certain exemplary embodiments provide plunger actuation systems that cause actuation of the syringe plunger at a fast rate in order to administer the therapeutic agent to a patient at a fast rate. Exemplary fast embodiments may administer therapeutic agent volumes of about 0.1 milliliters to about 1 milliliter in about one second to about thirty seconds, although exemplary administration rates are not limited to this exemplary range. In certain exemplary embodiments, therapeutic agent volumes of about 0.1 milliliters to about 1 milliliter may be administered in a time duration ranging from about 3 seconds to about 5 seconds. In certain exemplary embodiments, therapeutic agent volumes of about 0.1 milliliters to about 1 milliliter may be administered in a time duration of or shorter than about 20 seconds. Exemplary embodiments may provide a linear administration profile for the therapeutic agent so that the administration rate is substantially constant over time. In some cases, a linear administration profile may reduce discomfort experienced by the patient.

Figure 24:
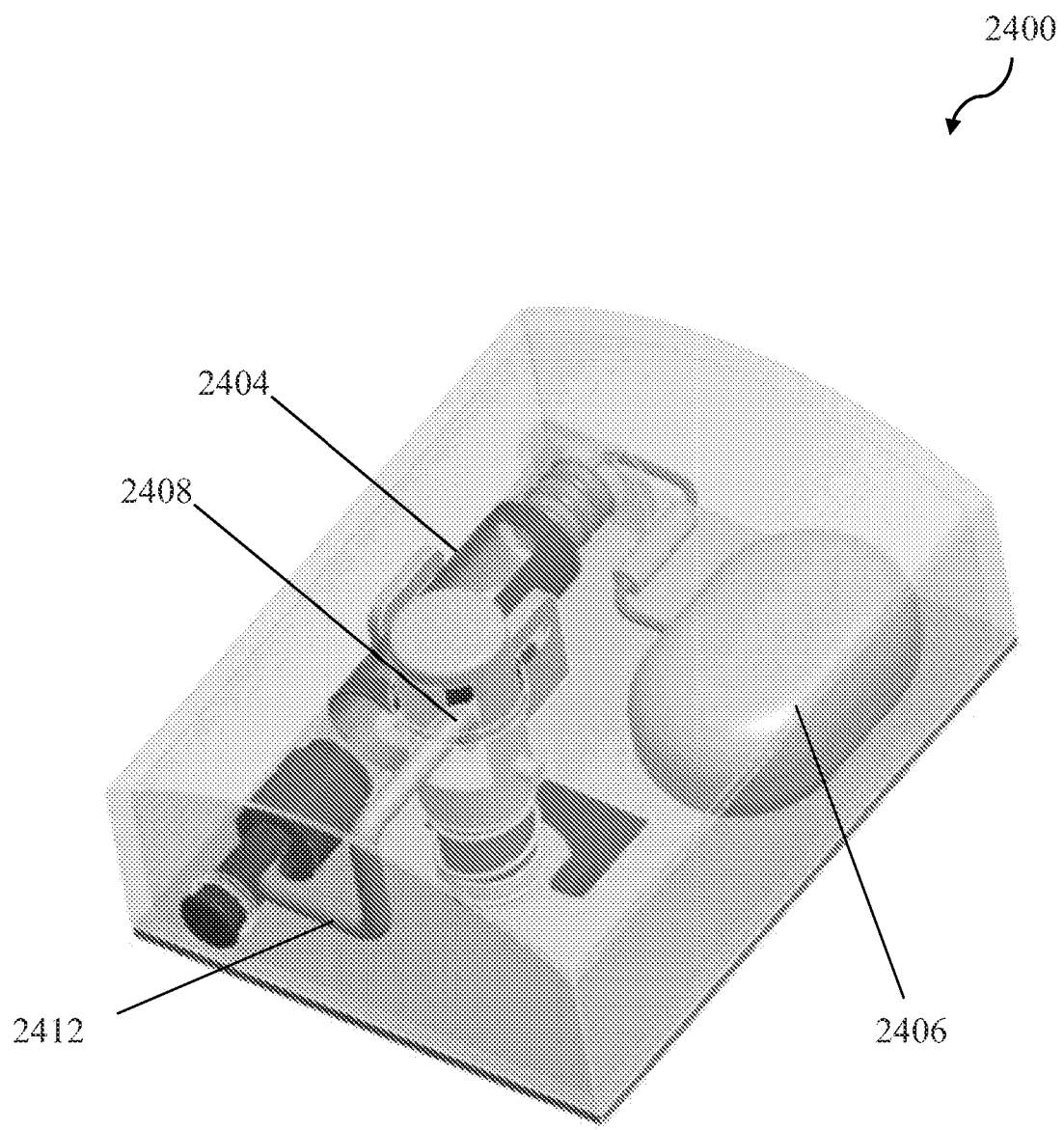
FIG. 24 is a perspective view through a cover of an exemplary automatic injection device including a plunger actuation mechanism that employs one or more fluid circuits.

FIG. 24 illustrates an exemplary automatic injection device 2400 that employs a fluid-based plunger actuation mechanism in which the fluid pressure of a working fluid and/or movement of a working fluid is used to move a bung within the barrel portion of a syringe or cartridge. The plunger actuation mechanism includes one or more fluid circuits to provide a force of the working fluid to a bung for expressing a dose of a therapeutic agent from a barrel portion 2404 of a syringe or cartridge. The wearable automatic injection device 2400 may include a pressure element 2406 that stores or is coupled to a source of an incompressible working fluid that provides a fluid pressure. Exemplary working fluids may include, but are not limited to, water, air, oil, and the like. Exemplary pressure elements may include, but are not limited to, an elastic bladder, a master cylinder, a spring-loaded syringe, and the like.

The pressure element 2406 may be coupled to a flow restrictor 2408 via a tubing. The flow restrictor 2408 may restrict the flow of the working fluid so that the fluid pressure upstream of the flow restrictor is greater than the fluid pressure downstream of the flow restrictor. The flow restrictor 2408 may include an orifice of diameter ranging from about 0.001 inch to about 0.01 inch, but the diameters of exemplary flow restrictor orifices are not limited to this exemplary range. The orifice of the flow restrictor 2408 may have lengths ranging from about 10 mm to about 50 mm, but the lengths of exemplary flow restrictor orifices are not limited this exemplary range.

Exemplary embodiments may configure a number of characteristics of the administration system to control the total administration time of the therapeutic agent. Exemplary embodiments may also configure a number of characteristics of the administration system based on the viscosity of the working fluid and/or the therapeutic agent. Exemplary characteristics may include, but are not limited to, the diameter of the orifice, the length of the orifice, the viscosity of the working fluid, and the like. For example, the diameter of the orifice of the flow restrictor may be decreased to increase the total administration time.

The flow restrictor 2408 may be coupled to the bung via a tubing 2412. When the working fluid is released from the pressure element 2406 via the flow restrictor 2408, the fluid pressure of the working fluid drives the bung forwardly within the barrel portion 2404 in order to expel the dose of the therapeutic agent from the barrel portion 2404.

In an exemplary embodiment, before administration in a pre-administration state, the working fluid may not be released from the pressure element 2406. In this exemplary embodiment, an administration trigger (not pictured) may be coupled to the pressure element 2406 so that, upon activation of the administration trigger, the working fluid is released from the pressure element 4106 into the tubings that couple the pressure element to the bung. The fluid pressure of the working fluid subsequently advances the bung within the barrel portion 2404, thus administering the dose to the patient. The fluid circuit established by the flow of the working fluid and the flow restrictor thereby provide a regulated force to the bung.

In an exemplary embodiment, the dose is administered in a linear administration profile, i.e., at a substantially constant administration rate. Linearity of the administration profile may be achieved by the high pressure of the working fluid provided by the pressure element 2406 upstream of the flow restrictor 2408 and the damping effect provided by the flow restrictor 2408. The pressure upstream of the flow restrictor 2408 may be maintained at a high level relative to projected stick-slip forces such that a highly damped system is achieved. For the bung to be moved forward within the barrel portion 2404, the bung would need to pull a vacuum on the working fluid between the flow restrictor 2408 and the barrel portion 2404, which is difficult to achieve to an appreciable extent because the working fluid is essentially incompressible.

Exemplary damped hydraulic administration circuits allow movement of the bung via volumetric metering, rather than by a direct application of force, thereby minimizing stick-slip phenomena in the administration profile of the therapeutic agent.

Figure 25:
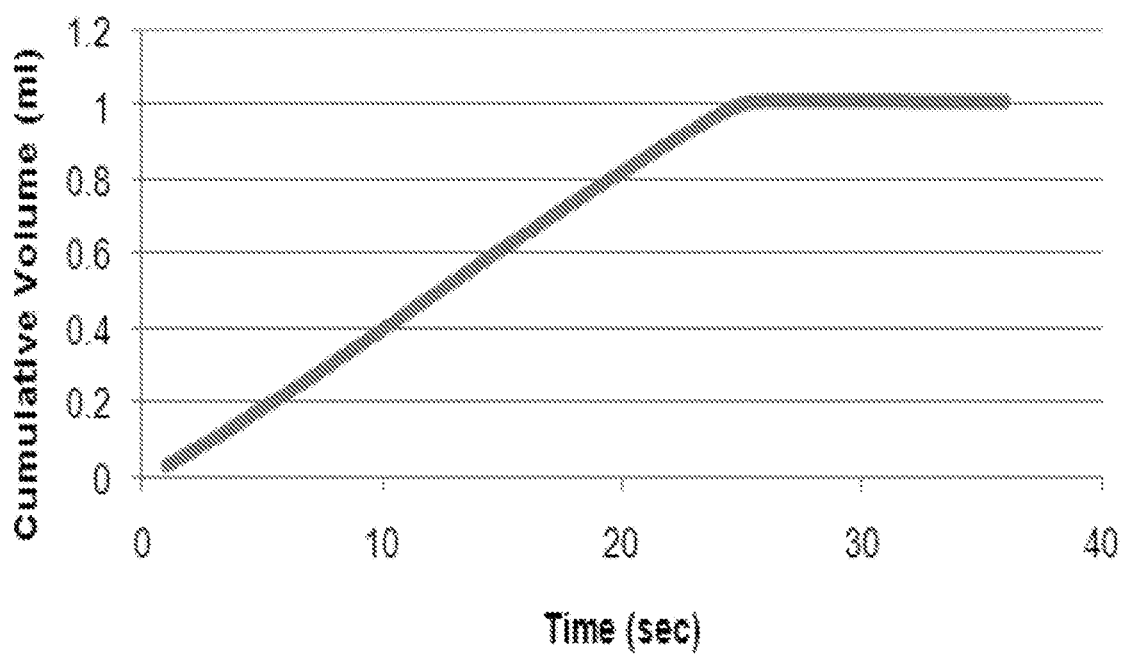
FIG. 25 illustrates a graph of the cumulative volume of therapeutic agent (in milliliters) against time (in seconds) as administered by an exemplary administration system including a flow restrictor.

FIG. 25 illustrates a graph of the cumulative volume of therapeutic agent (in milliliters) against time (in seconds) as administered by the exemplary administration system of FIG. 24 including a first exemplary flow restrictor having an exemplary diameter of about 0.008 inches and an exemplary length of about 34.3 mm. The total administration time for administering about 1 milliliter of a therapeutic agent was about 20 seconds. In the illustrative graph, the administration profile is substantially linear, i.e., substantially constant over time, and does not display an initial bolus or abrupt changes or inflections representative of inconsistent administration rates.

Figure 26:
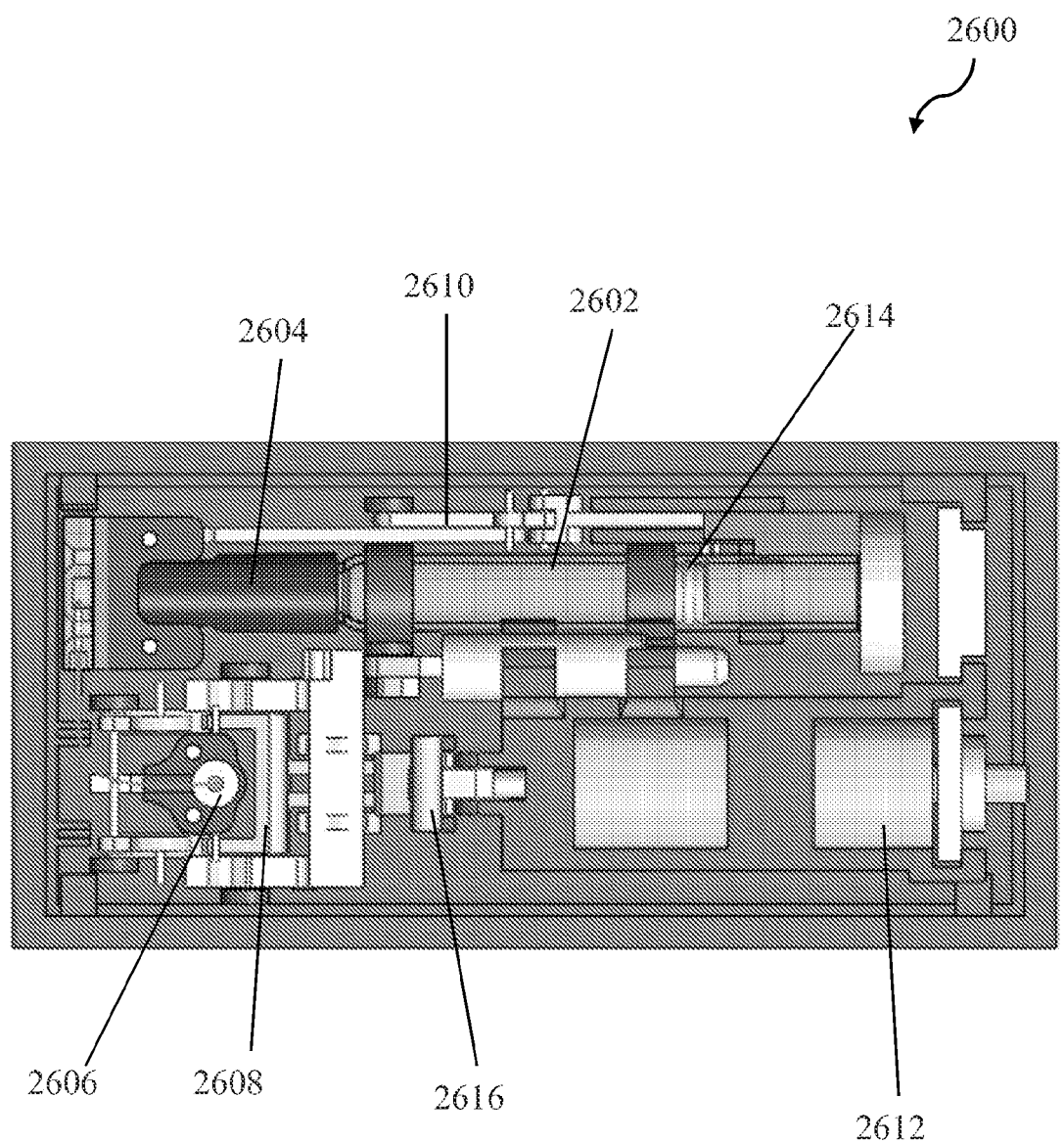
FIG. 26 is a schematic drawing of an exemplary automatic injection device including a plunger actuation mechanism that employs one or more fluid circuits.
Figure 27:
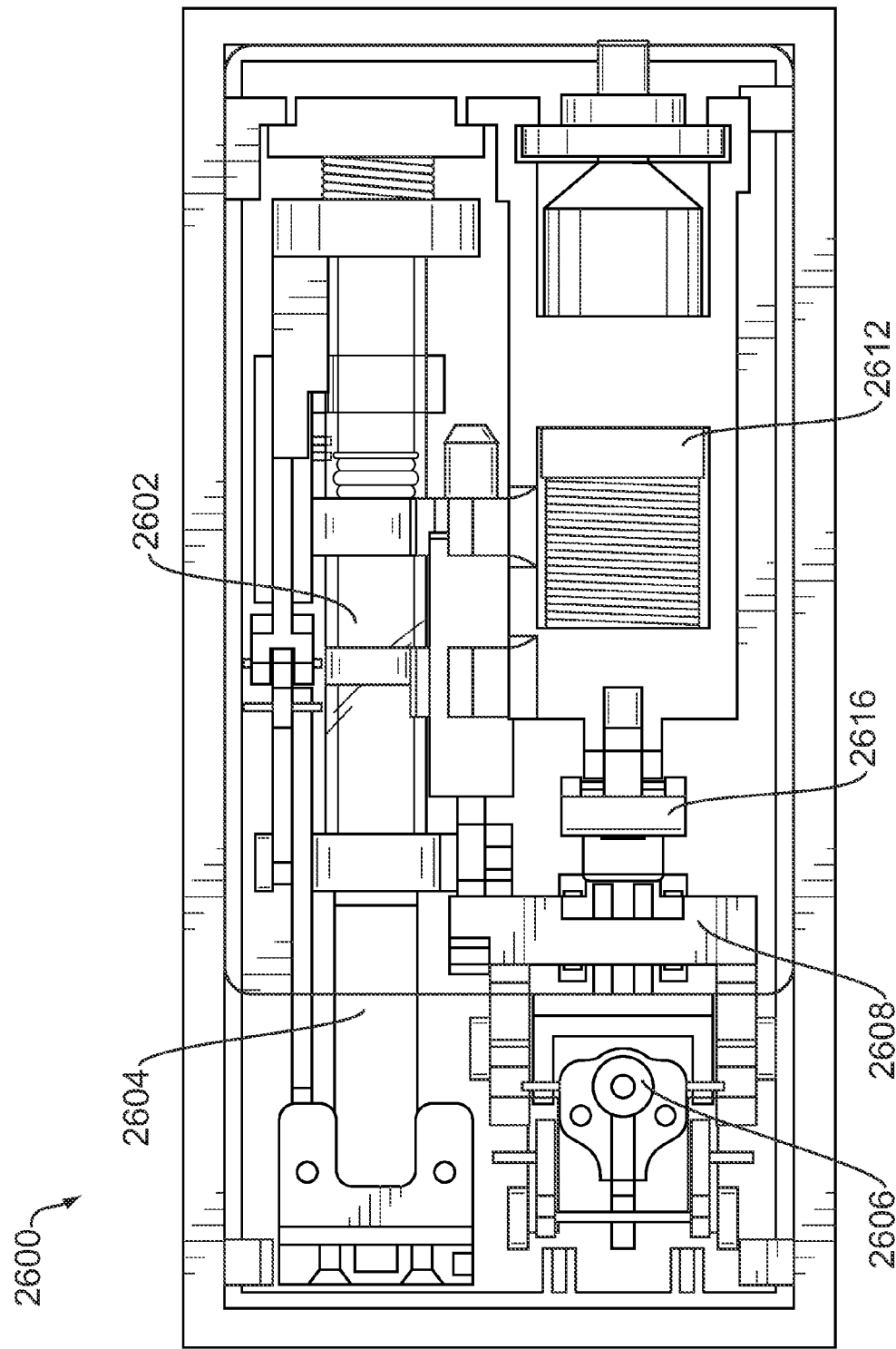
FIG. 27 is a top view of the exemplary device of FIG. 26.

FIG. 26 is a schematic drawing of an exemplary automatic injection device 2600 that employs one or more fluid circuits to provide a force for expressing a therapeutic agent from a cartridge assembly. FIG. 27 is a top view of the exemplary device 2600. The exemplary automatic injection device 2600 includes a barrel portion 2602 containing a dose of a therapeutic agent. A distal end of the barrel portion 2602 is provided in the vicinity of or coupled to a piercing needle (hidden by a piercing needle cover 2604) that is protectively covered by a piercing needle cover 2604. The piercing needle cover 2604 may maintain sterility of the piercing needle and a fluid conduit formed by and coupled to the piercing needle. The device 2600 includes an administration interface button that includes a septum and bears an administration interface (not pictured). In an exemplary embodiment, the device 2600 may include an administration interface carrier 2606 for holding the administration interface. In another exemplary embodiment, the piercing needle may be coupled directly to the administration interface without an intermediate carrier component for the administration interface. In an exemplary embodiment, the administration interface may be extend substantially orthogonally to the plane of the device as illustrated, and may be held in place by the administration interface carrier 2606. An administration interface lock 2608 may be provided for preventing the administration interface in a retracted position from protruding outside the housing once engaged and may be located in the housing near the administration interface.

In an exemplary embodiment, a syringe or cartridge actuator 2610 may be provided for advancing the barrel portion 2602 within the housing toward the septum. A trigger may be provided for triggering the syringe or cartridge actuator 2610, for example, when the administration interface button is pressed down or when the piercing needle cover 2604 is removed.

In this exemplary embodiment, a master cylinder 2612 containing a working fluid is provided for providing a fluid pressure to actuate a bung 2614 within the barrel portion 2602. The master cylinder 2612 may be coupled to an administration trigger 2616 that, when activated, releases the working fluid into fluid communication with the bung 2614 and allows the fluid pressure to advance the bung 2614 within the barrel portion 2602.

Exemplary embodiments also provide administration interface retraction systems for retracting an administration interface from a vertically lowered position (or an extended or deployed position) outside the housing of the device at the patient contact region to a vertically raised position (or a retracted position) within the housing of the device. The wearable automatic injection device 2600 includes a retraction mechanism that automatically raises the administration interface button from an extended or deployed position within the housing during administration in an administration state to a retracted position within the housing in a post-administration state after administration. In an exemplary embodiment, the retraction mechanism may be a telescoping element. The master cylinder 2612 may be coupled to a retraction trigger that, when activated, releases the working fluid into fluid communication with the retraction mechanism and allows the fluid pressure to activate the retraction mechanism.

Figure 28:
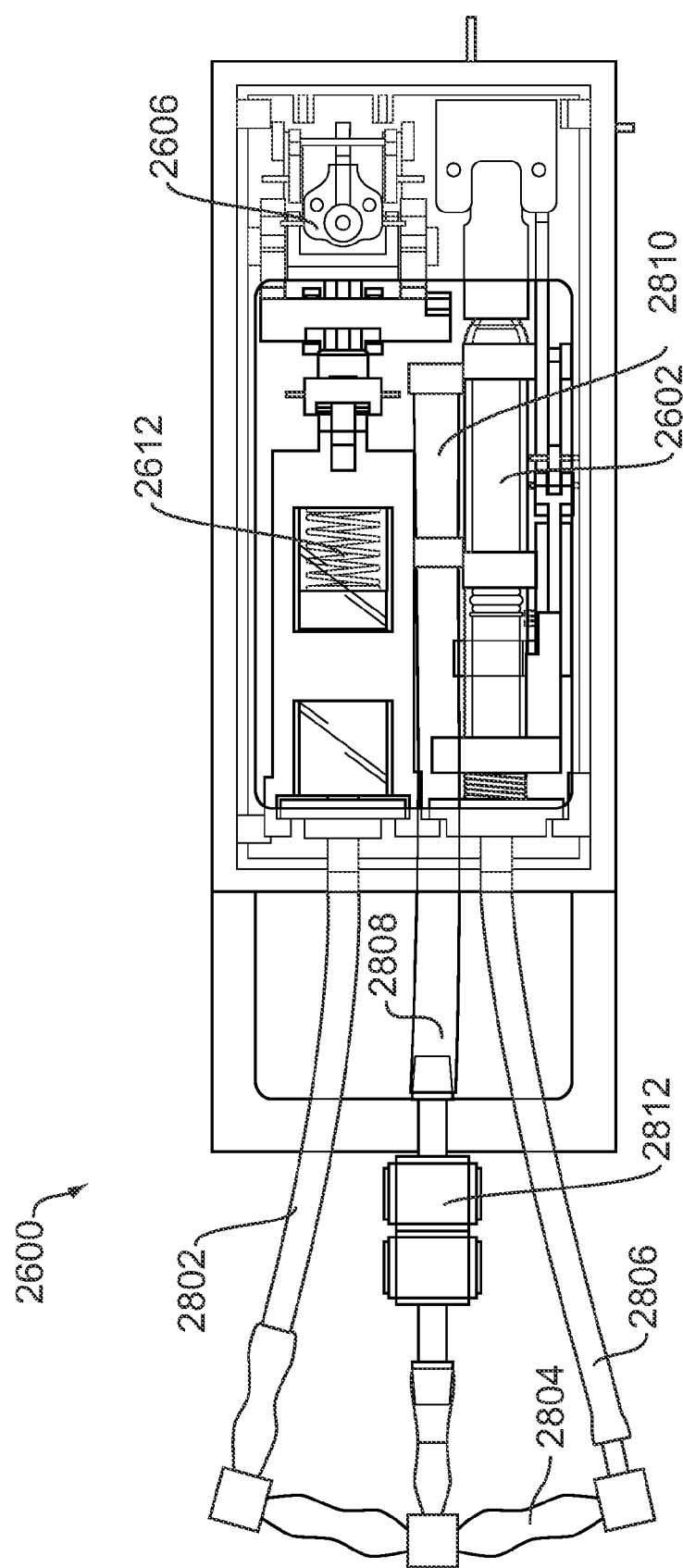
FIG. 28 illustrates a top view of an exemplary automatic injection device which shows a conduit coupling a master cylinder of a working fluid to a flow restrictor, a conduit coupling the flow restrictor to a bung, and a conduit coupling the master cylinder to a retraction mechanism via a valve.
Figure 29:
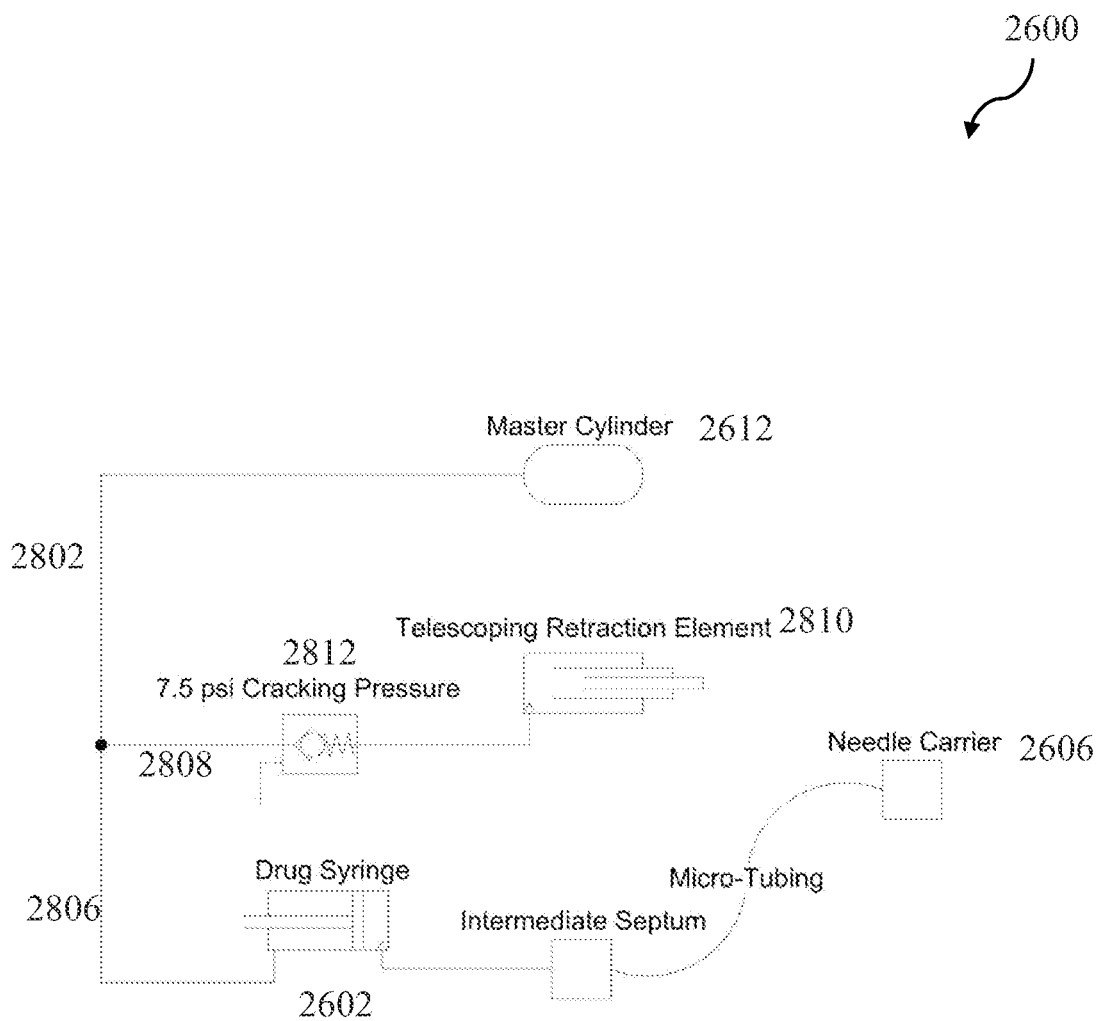
FIG. 29 illustrates a schematic diagram of the device of FIG. 28.

FIG. 28 illustrates a top view of the device 2600 which shows a conduit 2802 coupling the master cylinder 2612 to a flow restrictor 2804, a conduit 2806 coupling the flow restrictor 2804 to the bung in the barrel portion 2602 of the device, and a conduit 2808 coupling the master cylinder 2612 to a retraction mechanism 2810 via a valve 2812, for example, a check valve. FIG. 28 illustrates a schematic diagram of the device 2600.

The check valve 2812 may have a suitable cracking pressure at or above which the check valve 2812 allows fluid into the conduit 2808 coupled to the retraction mechanism 2810. In an exemplary embodiment, the cracking pressure is higher than the maximum fluid pressure in the conduit 2806 required to drive the bung during administration in an administration state. Otherwise, undesirably, the administration interface retraction process may begin during or even before administration. In an exemplary embodiment, the pressure in the conduit 2806 at the end of the movement of the bung during administration in an administration state is higher than the cracking pressure. Otherwise, at the end of the movement of the bung, the pressure in the conduit 2808 may be insufficient to activate the retraction mechanism 2810. The volume of the working fluid in the master cylinder 2612 is sufficient to administer the entire dose of the therapeutic agent and to activate the retraction mechanism 2810.

In an exemplary embodiment, the retraction mechanism 2810 and the check valve 2812 may be provided separately. In another exemplary embodiment, the retraction mechanism 2810 and the check valve 2812 may be provided as a single element, for example, as an inverting diaphragm.

Figure 30:
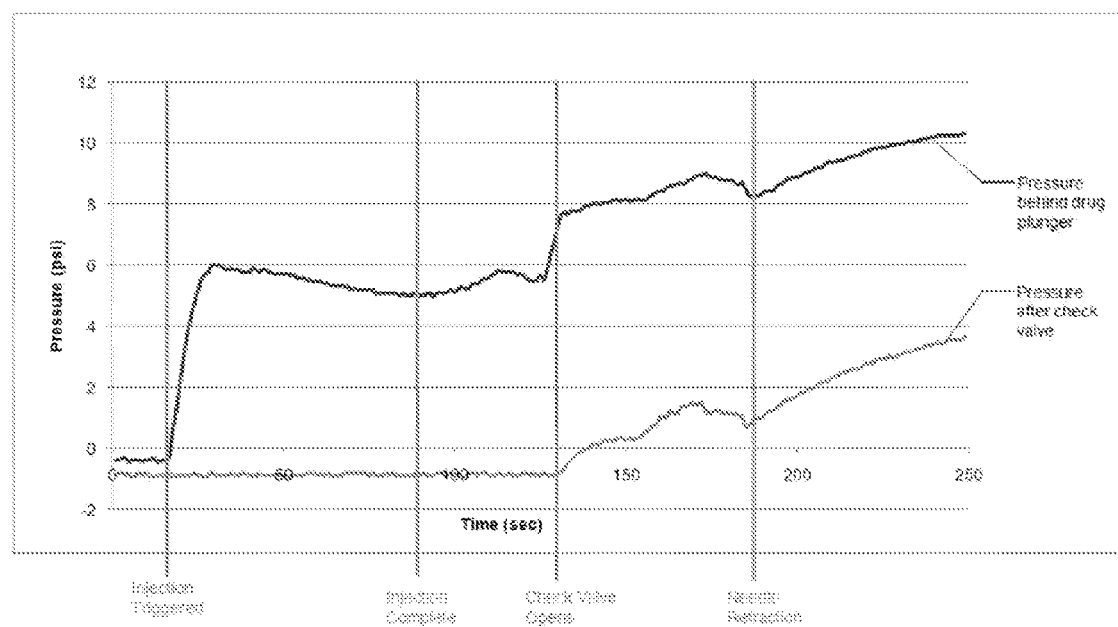
FIG. 30 illustrates a graph of exemplary pressures after a check valve and behind a bung (in psi) versus time (in seconds) in an exemplary automatic injection device.

FIG. 30 illustrates a graph of the pressure after the check valve and behind the bung (in psi) versus time (in seconds) in an exemplary embodiment. In an exemplary embodiment, the cracking pressure of the check valve may be about 7.5 psi and the diameter of the flow restrictor orifice may be about 0.008 inches.

During administration in an administration state, the flow restrictor 2804 may cause the pressure in the conduit 2802 to be about 10 to about 15 psi, while the pressure in the conduit 2806 may be about 5 to about 6 psi. The check valve 2812 thus prevents any flow of the working fluid from entering the conduit 2808 while the bung is moving during administration. Once the bung stops moving at the end of administration, i.e., when the dose has been expelled from the barrel portion 2602, the pressure in the conduit 2806 increases beyond 7.5 psi. This causes the check valve 2812 to open, allowing the working fluid to flow into the conduit 2808 which activates the retraction mechanism 2810. The retraction mechanism 2810 in turn unlocks the administration interface lock and retracts the administration interface button/carrier 2606 bearing the administration interface. Because it is based on pressure equalization in the hydraulic circuit, the administration interface retraction process ensures that the entire dose is administered before the administration interface is retracted, maximizes utilization of the therapeutic agent, and minimizes the overfill required in the barrel portion 2602.

Any suitable trigger mechanism may be used to trigger the administration interface retraction systems. In an exemplary embodiment, the trigger mechanism may automatically trigger the administration interface retraction system when the wearable automatic injection device moves from an administration state to a post-administration state. In an exemplary embodiment, completion of the administration of a therapeutically effective dose of the therapeutic agent may trigger the administration interface retraction system. In another exemplary embodiment, the removal of the device from the patient before completion of the administration of a therapeutically effective dose of the therapeutic agent may trigger the administration interface retraction system. In another exemplary embodiment, the administration interface retraction system may be manually triggered by a patient.

Figure 31:
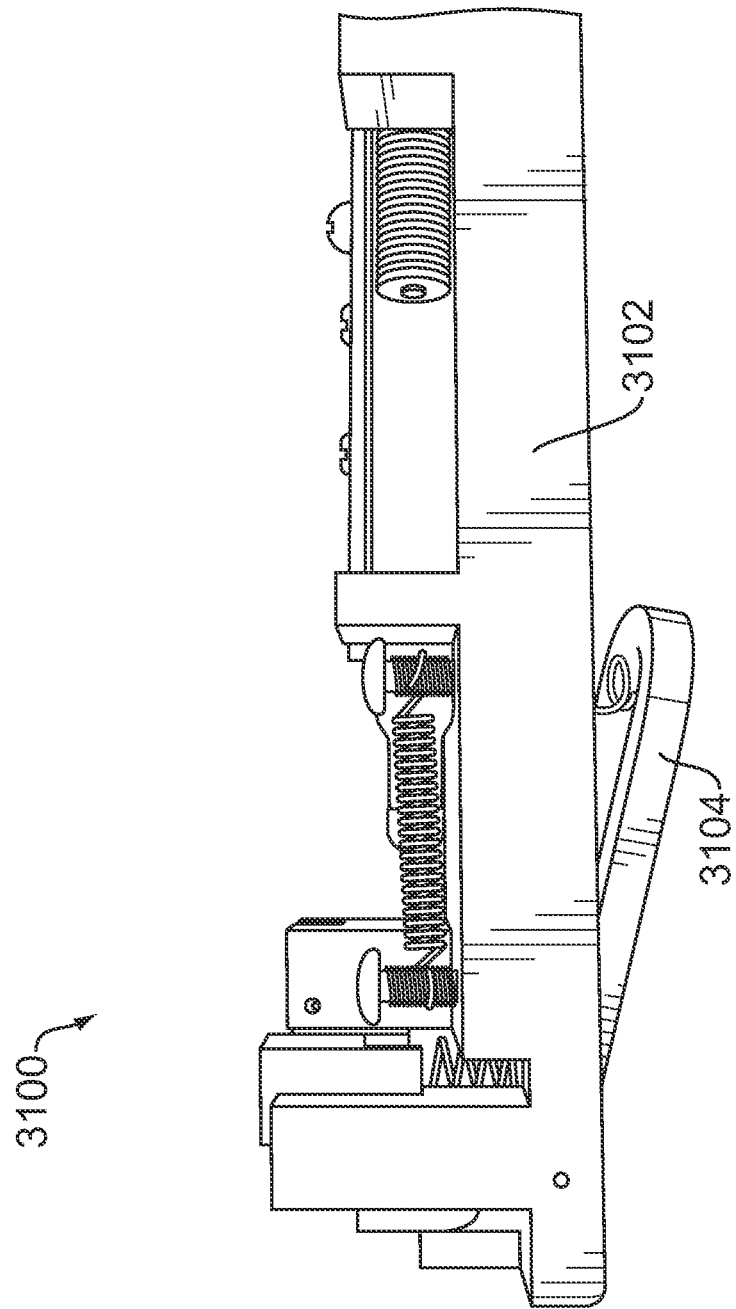
FIG. 31 illustrates a side view of an exemplary automatic injection device in which the housing of the wearable automatic injection device includes a skin sensor foot.

FIG. 31 illustrates a side view of an exemplary automatic injection device 3100 in which the housing 3102 of the wearable automatic injection device 3100 includes a skin sensor foot 3104, which is a structure in an exemplary embodiment housed under or in the portion of the housing 3102 proximal to the administration site. In an exemplary embodiment, prior to administration of the therapeutic agent and during administration, the skin sensor foot 3104 is retained within or forms a portion of the underside of the housing 3102. When the wearable automatic injection device 3100 is attached to the administration site and activated, the skin sensor foot 3104 may be free to move but may be constrained by the administration site. In an exemplary embodiment, when the wearable automatic injection device 3100 is removed from the administration site, regardless of whether administration of the therapeutic agent was completed, the skin sensor foot 3104 is no longer constrained, and extends and projects outside the periphery of the housing 3102. This, in turn, activates a retraction trigger. When the retraction trigger is activated, a retraction mechanism retracts the administration interface which may also raise the administration interface button from the vertically lowered position to the vertically raised position, so that the administration interface button protrudes from the top of the housing 3102 and the administration interface is retracted within the housing 3102.

V. Exemplary Administration Interface Protection Systems

Exemplary embodiments provide different exemplary administration interface protection systems for maintaining an administration interface in a retracted position within the wearable automatic injection device in a pre-administration state before administration of a therapeutic agent and in a post-administration state after administration. Retraction and protection of the administration interface within the housing of the device prevents accidental needle sticks from injuring the patient or any other humans in the vicinity of the wearable automatic injection device.

Figures 32A, 32B:
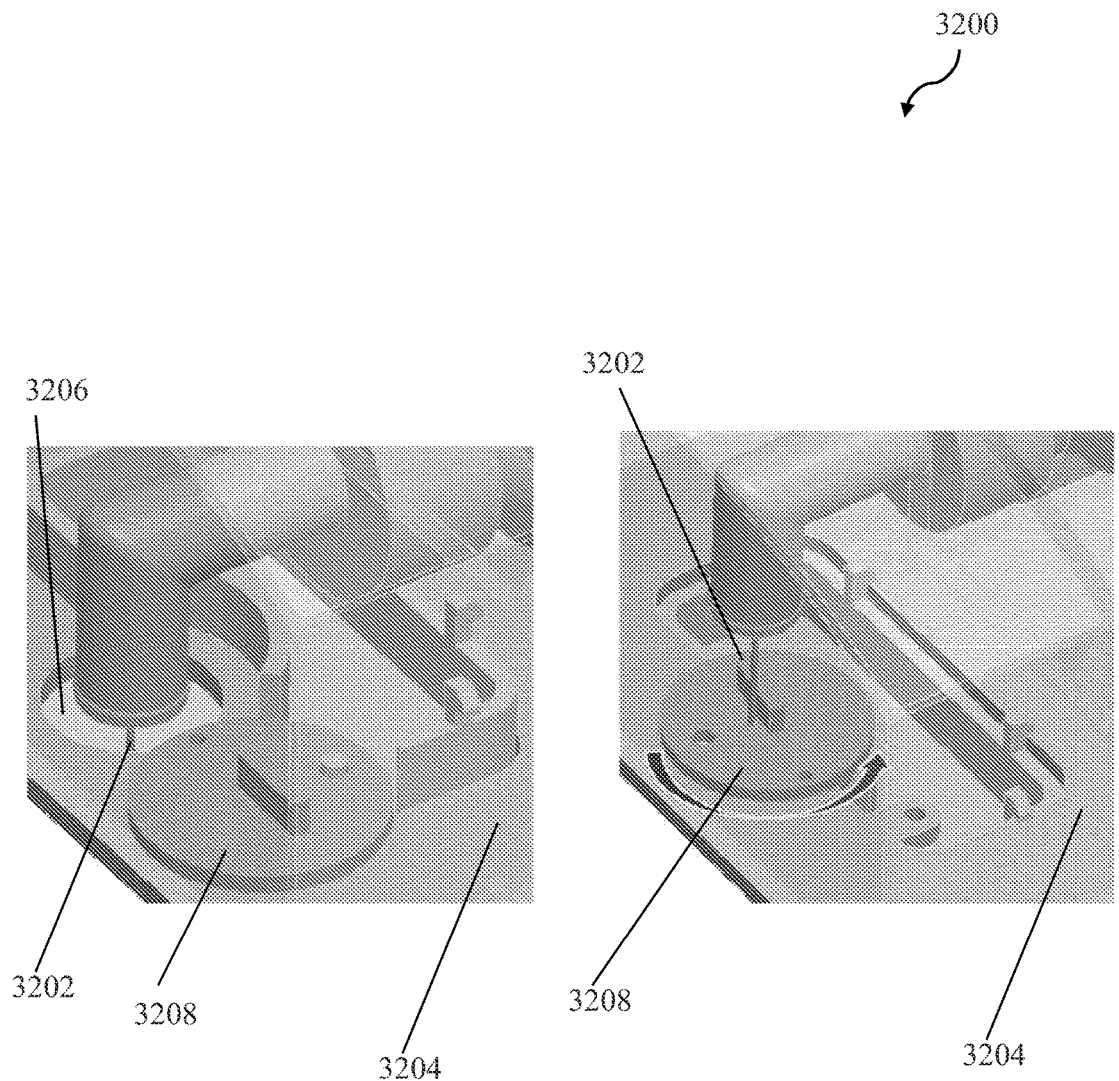
FIGS. 32A and 32B illustrate an exemplary administration interface protection system that maintains an administration interface in a retracted position within the housing of an exemplary automatic injection device.

FIGS. 32A and 32B illustrate an exemplary administration interface protection system 3200 that maintains an administration interface 3202 in a retracted position within a housing 3204 of an automatic injection device. Exemplary administration interfaces may include a single injection needle, a plurality of injection needles, a needle-free pad, a needle-free patch, and the like.

In an exemplary embodiment, the administration interface 3202 is movable relative to the housing 3204 away from or toward the patient's body. When the administration interface 3202 is in a position within the housing 3204 farther from the patient's body, the administration interface 3202 is in a retracted position and does not protrude outside the housing 3204. The administration interface 3202 is in a retracted position when the device is in a pre or post-administration state. When the administration interface 3202 is in a position within the housing 3204 closer to the patient's body, the administration interface 3202 is in an extended or deployed position and protrudes fully or partly from the housing 3204. The housing 3204 may be provided with an aperture 3206 through which the administration interface 3202 may protrude outside the housing 3204. The administration interface 3202 is in an extended or deployed position when the device is in an administration state.

The administration interface protection system 3200 employs a barrier mechanism 3208 which prevents the administration interface 3202 from protruding from the housing 3204 in a pre-administration state before administration and in a post-administration state after administration when the administration interface 3202 is in the retracted position. FIG. 32A illustrates the system 3200 in which the administration interface 3202 is in an extended or deployed position and protrudes fully or partly through the aperture 3206 outside the housing 3204, for example, during administration in an administration state. In this case, the barrier mechanism 3208 is displaced away from the aperture 3206 so that the aperture 3206 is open to the outside of the housing 3204 and the administration interface 3202 is free to protrude through the aperture 3206 to the outside of the housing 3204. FIG. 32B illustrates the system 3200 in which the administration interface 3202 is in a retracted position and does not protrude from the housing 3204, for example, in a pre-administration state and a post-administration state. In this case, the barrier mechanism 3208 is aligned with and covers the aperture 3206 so that the aperture 3206 is no longer open to the outside of the housing 3204 and the administration interface 3202 is not free to protrude through the aperture 3206 to the outside of the housing 3204. In an exemplary embodiment, the barrier mechanism 3208 may be moved rotatably above a point of rotation between a first position in which it exposes the aperture 3206 (in FIG. 32A) to a second position in which it covers the aperture 3206 (in FIG. 32B).

FIGS. 33A and 33B illustrate another exemplary administration interface protection system 3300 provided in the housing 3302 of an automatic injection device. The housing 3302 may be provided with an aperture through which an administration interface may protrude outside the housing 3302. An exemplary administration interface may include, but is not limited to, an injection needle, multiple injection needles, a needle-free patch or pump, and the like. In an exemplary embodiment, the automatic injection device includes an administration interface that is movable relative to the housing 3302 away from or toward the patient's body along vertical axis V. Exemplary administration interfaces may include a single injection needle, a plurality of injection needles, a needle-free pad, a needle-free patch, and the like. When the device is in a pre- or post-administration state, the administration interface is in a retracted position farther from the patient's body and does not protrude outside the housing 3302. When the device is in an administration state, the administration interface is in an extended or deployed position closer to the patient's body and protrudes fully or partly outside the housing 3302. In an exemplary embodiment, the administration interface may be directly or indirectly coupled to a tab or pin 3308. The tab 3308 is a mechanical member coupled to the administration interface to enable the administration interface to be extended when the device is in an administration position, and that locks the administration interface in a retracted position when the device is in a pre- or post-administration state.

The administration interface protection system 3300 includes a lockout sleeve 3306 provided in the vicinity of the administration interface for locking the administration interface in the retracted position in a pre-administration state and a post-administration state. An exemplary lockout sleeve 3306 is a substantially tubular or cylindrical member that is capable of rotating about a central axis of rotation extending through the member. The lockout sleeve 3006 may include a L-shaped slot or groove including a first portion 3304 extending along the vertical axis V and a second portion 3310 extending perpendicular to the vertical axis V. The tab 3308 is provided to be accommodated within and to extend through the slot to the outside of the lockout sleeve 3306.

The administration interface protection system 3300 also includes a skin sensor foot 3312 that interfaces with the lockout sleeve 3306 at a wedged interface 3314. The skin sensor foot 3312 may be activated when the wearable automatic injection device 3300 is removed from the administration site. When activated, the skin sensor foot 3312 may move relative to the interface 3314 to protrude outside the housing 3302. The movement of the skin sensor foot 3312 relative to the interface 3314 causes the lockout sleeve 3306 to rotate about its central axis of rotation. Before the skin sensor foot 3312 is activated, the tab 3308 may be positioned at the connection between the first and second portions of the slot (illustrated in FIG. 33A). In this position, the tab 3308 is able to slide downward along the first portion 3304 of the slot extending along the vertical axis V. This, in turn, enables the administration interface to be moved along with the tab 3308 from the retracted position to the extended position in which the administration interface may be used to administer a therapeutic agent to a patient. When the activation of the skin sensor foot 3312 causes rotation of the lockout sleeve 3306, the second portion 3310 of the slot is moved horizontally so that the tab 3308 is positioned at the terminal end of the second portion 3310 of the slot (illustrated in FIG. 33B). In this position, the tab 3308 is no longer free to slide downward along the vertical axis V. This, in turn, prevents the administration interface to be moved along with the tab 3308 from the retracted position to the extended position, and effectively locks the administration interface to the retracted position within the housing 3302.

Figure 34:
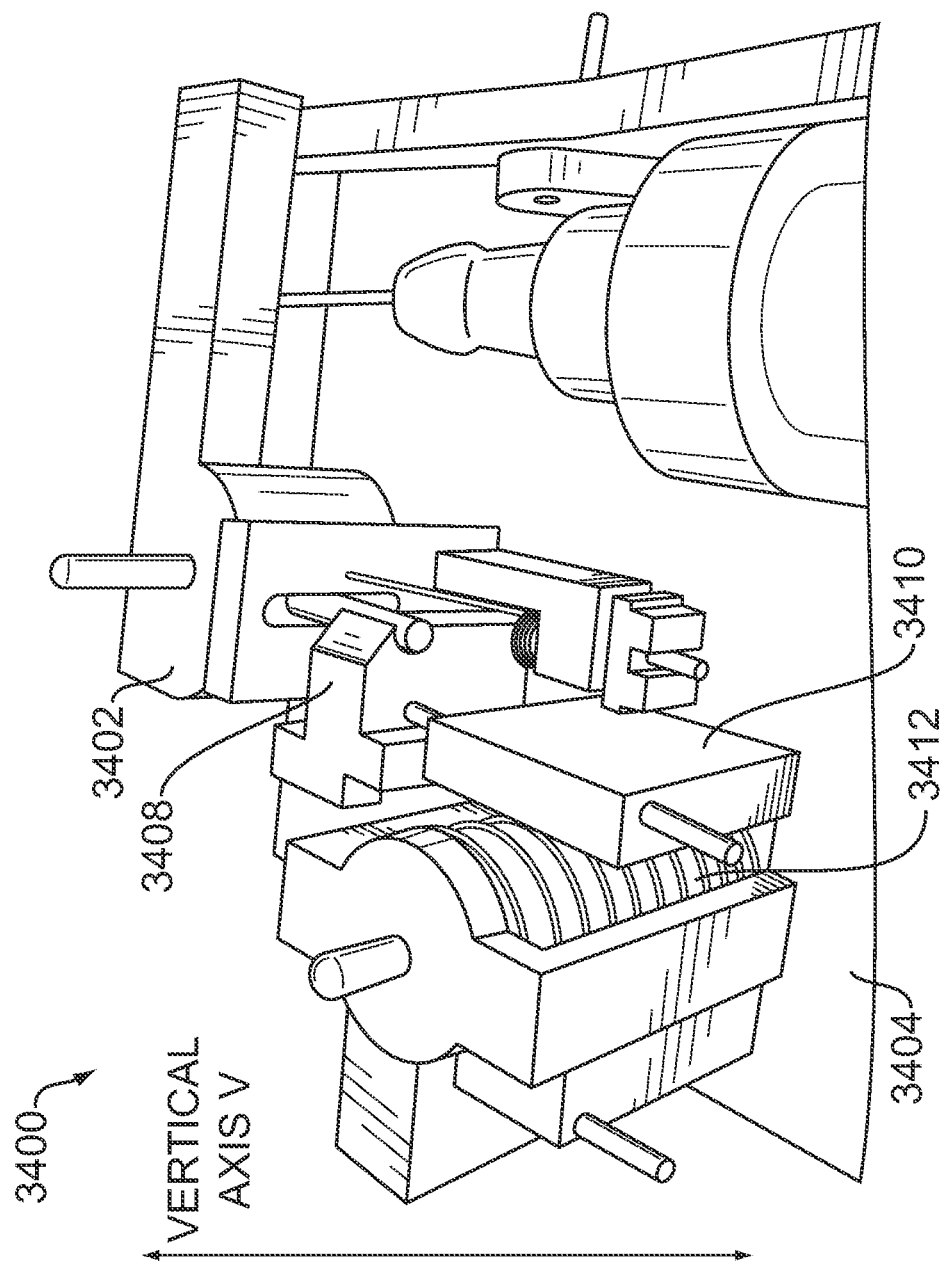
FIG. 34 illustrates another exemplary administration interface protection system that maintains an administration interface in a retracted position within the housing of an exemplary automatic injection device.

FIG. 34 illustrates an exemplary administration interface protection system 3400 that maintains an administration interface held by an administration interface carrier 3402 in a retracted position within a housing 3404 of an automatic injection device. In an exemplary embodiment, the administration interface is movable relative to the housing 3404 away from or toward the patient's body along the vertical axis V. When the administration interface is in a position within the housing 3404 farther from the patient's body, the administration interface may be in a retracted position and may not protrude outside the housing 3404. In an exemplary embodiment, the administration interface is in a retracted position when the device is in a pre or post-administration state. When the administration interface is in a position within the housing 3404 closer to the patient's body, the administration interface may be in an extended or deployed position and may protrude fully or partly from the housing 3404. The housing 3404 may be provided with an aperture through which the administration interface may protrude outside the housing 3404. In an exemplary embodiment, the administration interface is in an extended or deployed position when the device is in an administration state.

The administration interface protection system 3400 may include an administration interface lock 3408 coupled to the administration interface carrier 3402. In an exemplary embodiment, the administration interface lock 3408 may be a pivoting or rotating member that may pivot or rotate about a pivoting point or interface. An administration interface lock release mechanism 3410 may be provided in the vicinity of or in contact with the administration interface lock 3408. The administration interface protection system 3400 may also include a biasing mechanism 3412 that is biased against a skin sensor foot (not illustrated).

When the device is placed on an administration site, the skin sensor foot is not activated and the administration interface lock release mechanism 3410 is in a released position. This prevents a locking interaction between the administration interface lock release mechanism 3410 and the administration interface lock 3408, which allows the administration interface carrier 3402 to move downward along the vertical axis V from the retracted position to the extended position to protrude outside the housing 3404. When the skin sensor foot is activated by removal of the device from the administration site, the biasing mechanism 3412 triggers the administration interface lock release mechanism 3410 to move linearly or in a rotary manner so that it interacts with the administration interface lock 3408 and locks the administration interface lock 3408. In this position of the administration interface lock 3408, the administration interface carrier 3402 is locked in a raised position in which the administration interface is retracted within the housing 3404.

In an exemplary embodiment, the piercing needle may be coupled directly to the administration interface without an intermediate carrier component for the administration interface. In another exemplary embodiment, the piercing needle may be coupled to the administration interface through an intermediate carrier component for the administration interface.

Figure 35A:
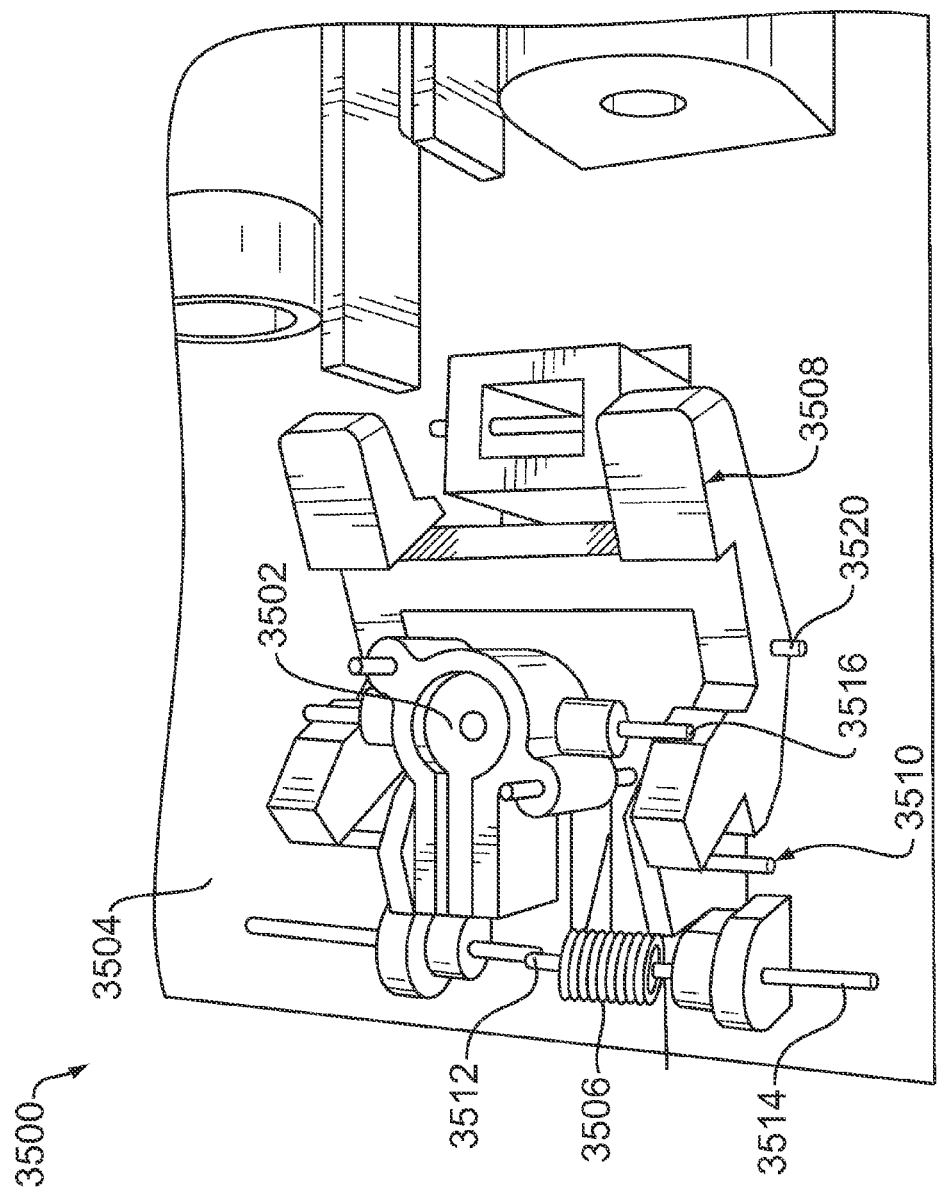
FIG. 35A illustrates a perspective view of another exemplary administration interface protection system that maintains an administration interface in a retracted position within the housing of an exemplary automatic injection device.
Figure 35B:
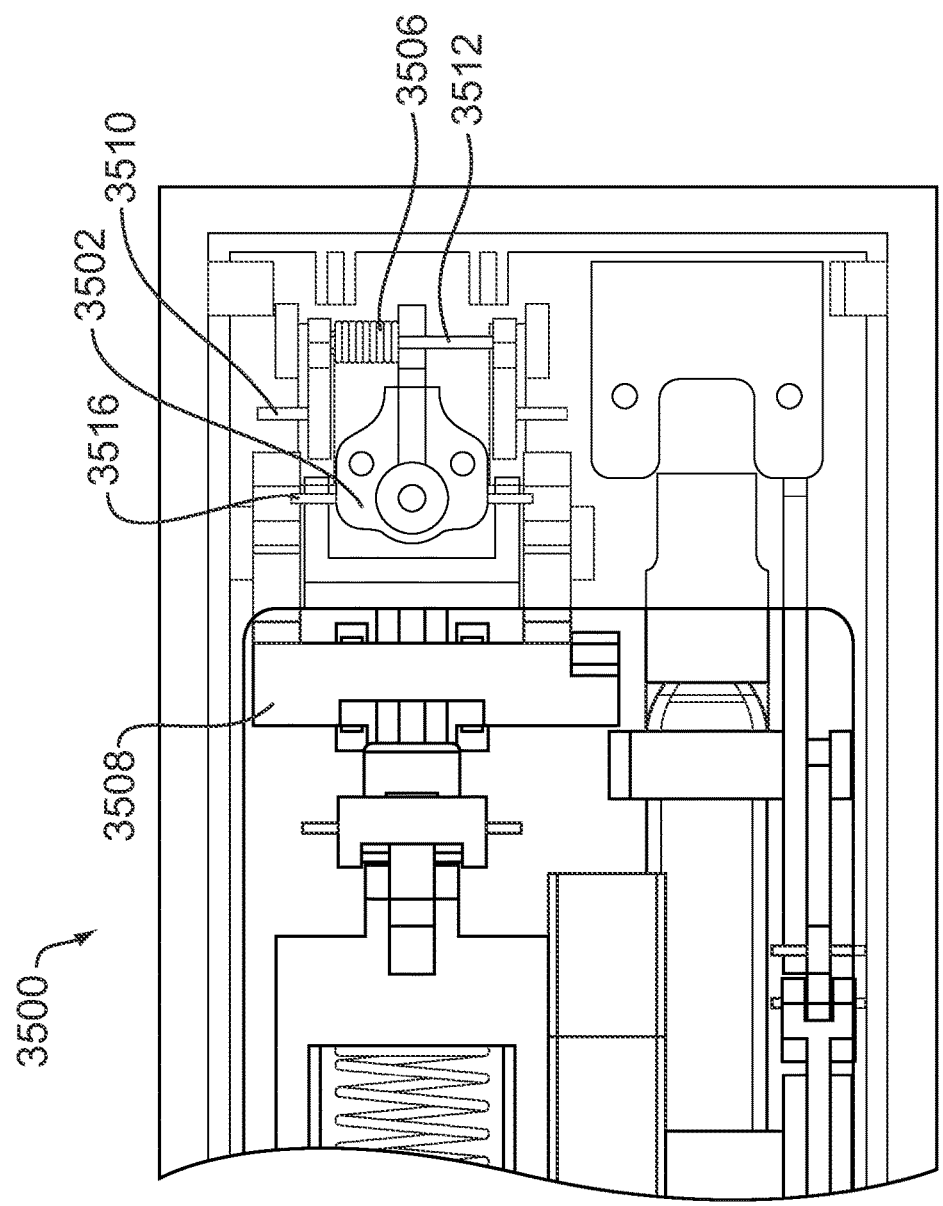
FIG. 35B illustrates a top view of the exemplary administration interface protection system of FIG. 35A.
Figure 35C:
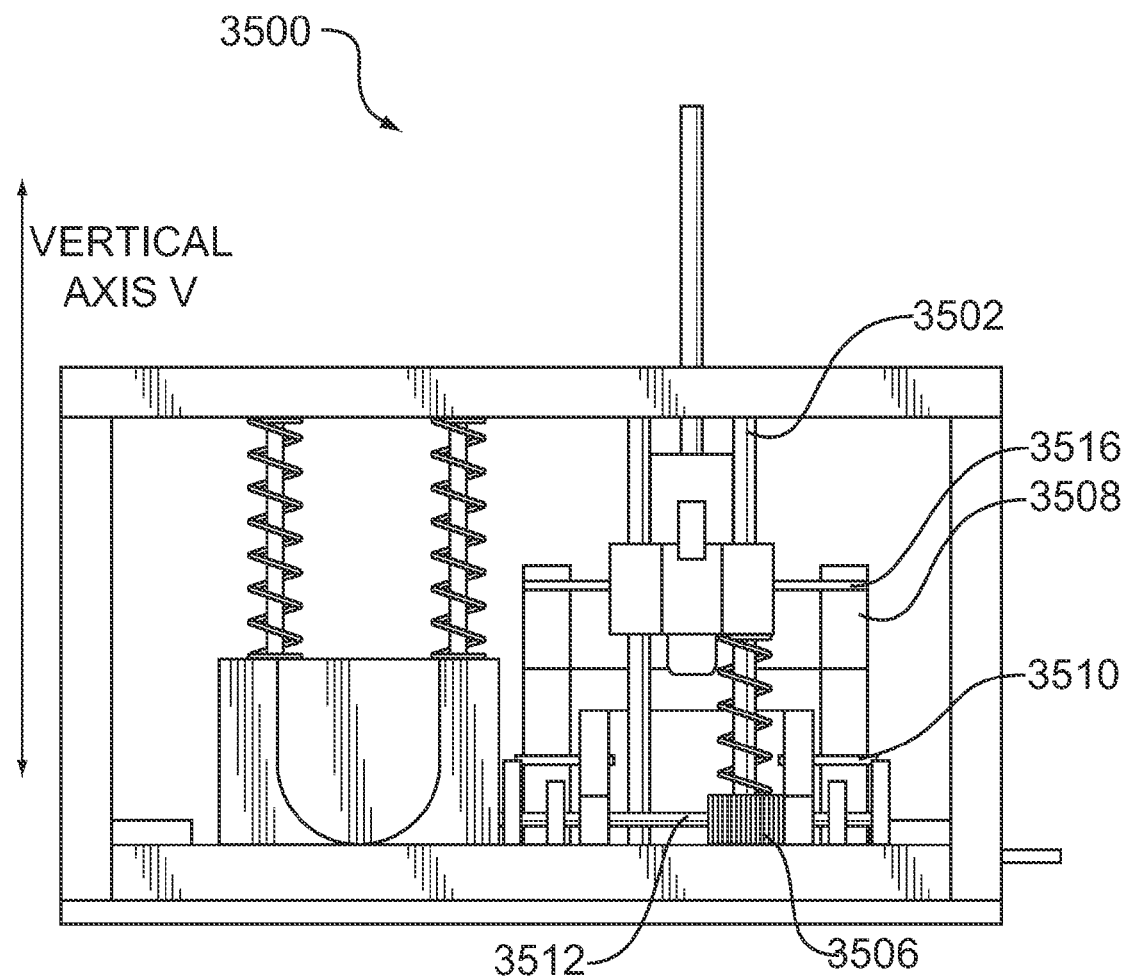
FIG. 35C illustrates a first side view of the exemplary administration interface protection system of FIG. 35A.
Figure 35D:
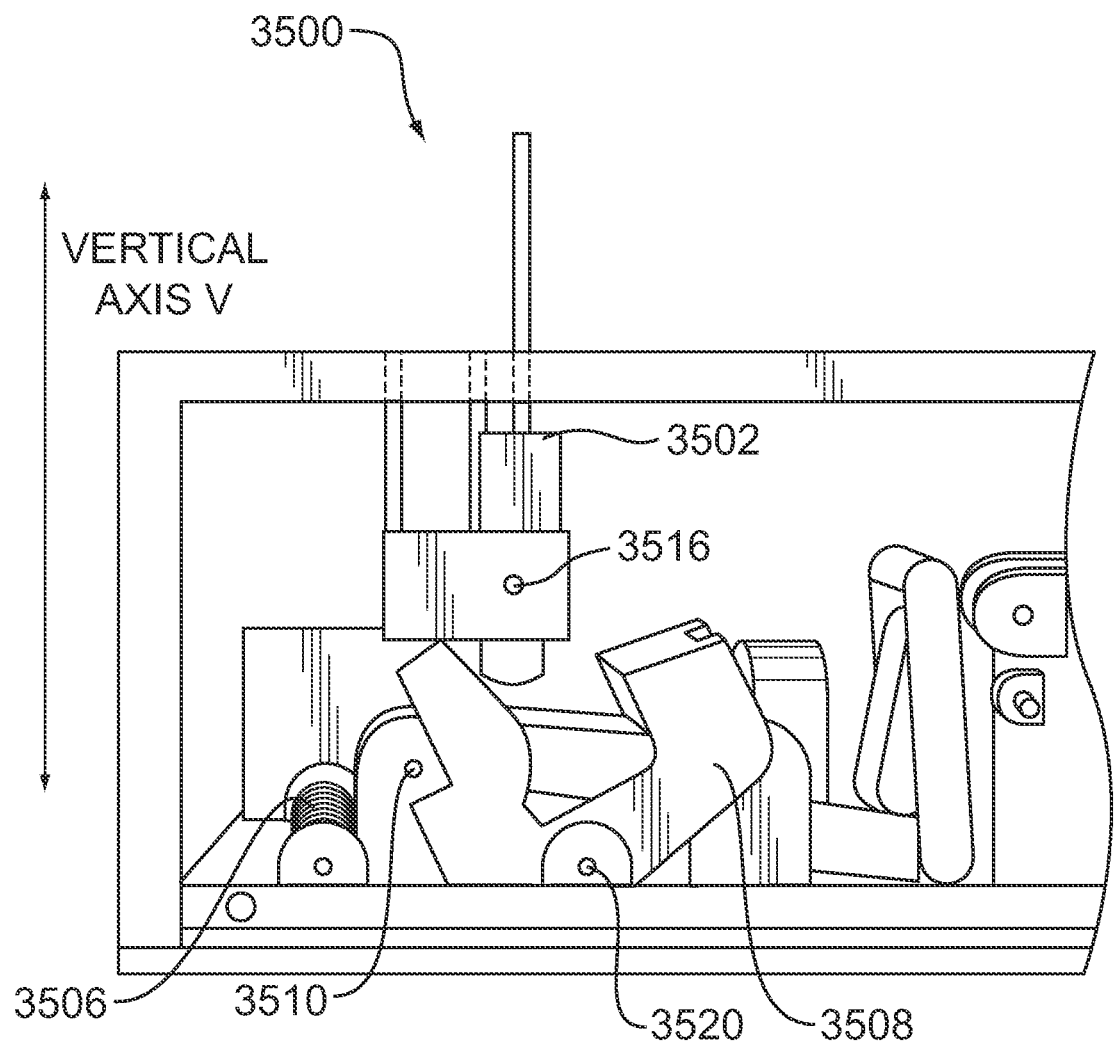
FIG. 35D illustrates a second side view of the exemplary administration interface protection system of FIG. 35A in which the automatic injection device is in an administration state.
Figure 35E:
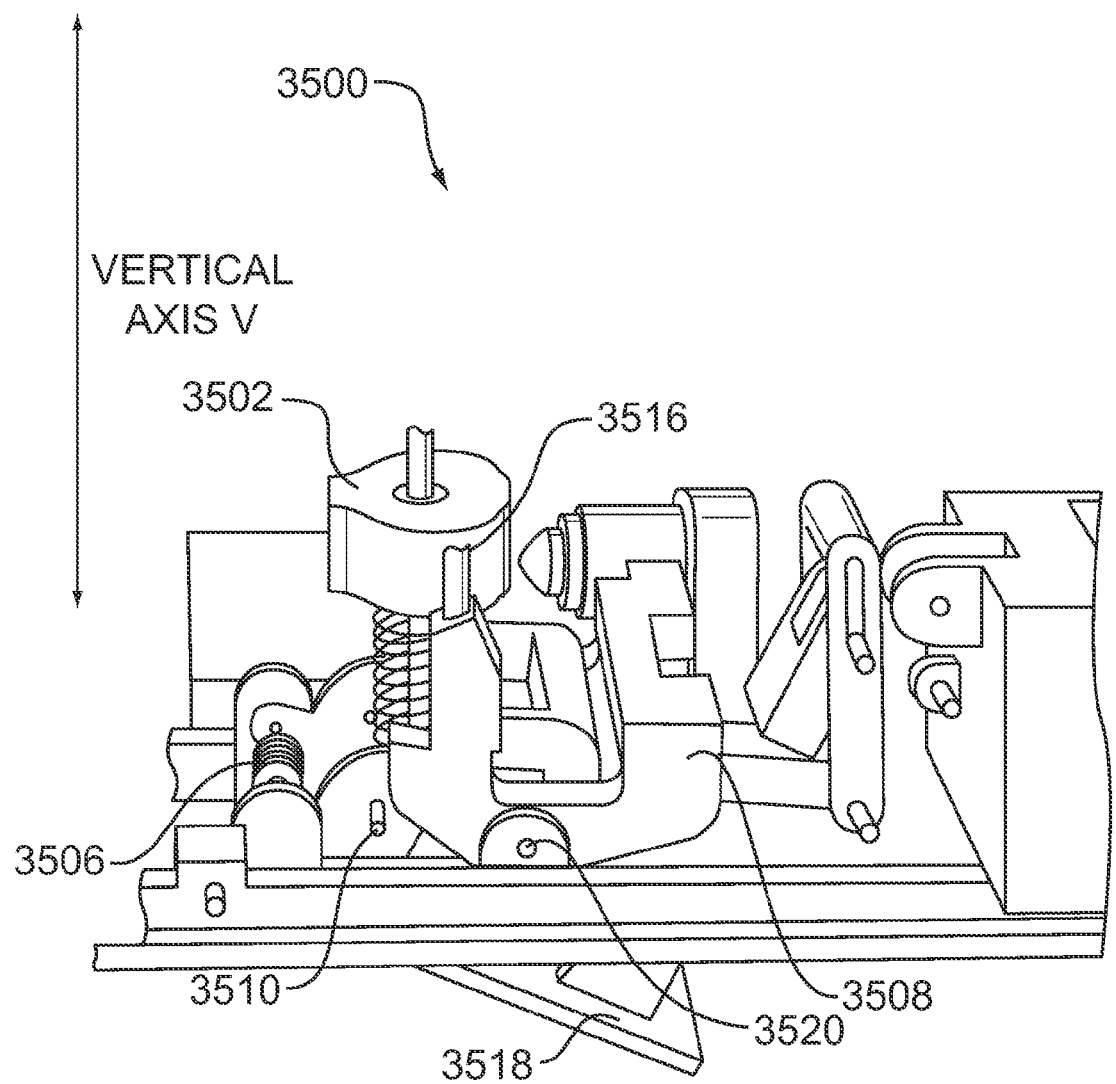
FIG. 35E illustrates the second side view of the exemplary administration interface protection system of FIG. 35A in which the automatic injection device is in a pre- or post-administration state.

FIGS. 35A-35E illustrates another exemplary administration interface protection system 3500 that maintains an administration interface held by an administration interface carrier 3502 in a retracted position within a housing 3504 of an automatic injection device. FIG. 35A illustrates a perspective view of the system 3500; FIG. 35B illustrates a top view of the system 3500; FIG. 35C illustrates a first side view of the system 3500; FIG. 35D illustrates a second side view of the system 3500 in which the device is in an administration state; and FIG. 35E illustrates a second side view of the system 3500 in which the device is in a pre- or post-administration state.

The device may include a housing 3504 and an administration interface carrier 3502 provided in the housing 3504 for holding an administration interface aligned along the vertical axis V. The housing 3504 may include an aperture for allowing the administration interface to protrude outside the housing 3504 and to administer a therapeutic agent to a patient. Vertical movement of the administration interface carrier 3502 enables vertical movement of the administration interface between a retracted position in which the administration interface does not protrude outside the housing 3504 (in a pre- or post-administration state of the device) and an extended position in which the administration interface protrudes fully or partially outside the housing 3504 at the administration site on the patient's body (in an administration state of the device).

The administration interface carrier 3502 includes a tab or pin 3516 that extends radially outwardly from the carrier 3502. The tab 3516 is configured to interact with an administration interface lock mechanism 3508 when the device is in a pre- or post-administration state in order to lock the administration interface carrier 3502 in a vertically raised retracted position. The administration interface protection system 3500 may include an administration interface lock mechanism 3508 provided in the vicinity of or in contact with the administration interface carrier 3502. In an exemplary embodiment, the administration interface lock 3508 may be a pivoting or rotating member that may pivot or rotate about a pivoting point or interface 3520.

The administration interface protection system 3500 may include a biasing mechanism 3506 provided around a biasing mechanism carrier 3512 that is an elongated mechanical member, e.g., a metallic bar or rod. The biasing mechanism carrier 3512 may be coupled to a skin sensor foot 3518. The biasing mechanism carrier 3512 may also be coupled to a pivot point 3514 of an administration interface release mechanism 3510 so that rotation of the biasing mechanism carrier 3512 under the bias of the biasing mechanism 3506 causes rotation of the administration interface release mechanism 3510 about the pivot point 3514. In an exemplary embodiment, the administration interface release mechanism 3510 may be a separate component from the skin sensor foot 3518. In another exemplary embodiment, the administration interface release mechanism 3510 may be a component of the skin sensor foot 3518.

Placement of the device against an administration site may cause the skin sensor foot 3518 to be raised toward the housing 3504, thereby causing the biasing mechanism 3506 (and the biasing mechanism carrier 3512) to rotate in a first direction so that the administration interface release mechanism 3510 is pivoted into a position in which the mechanism 3510 does not interact with the administration interface lock mechanism 3508 in a locking manner. This results in the administration interface lock mechanism 3508 being maintained in a "down" position so that the administration interface carrier 3502 is free to move downward to extend the administration interface outside the housing 3502 to administer a therapeutic agent.

Removal of the device from the administration site causes the skin sensor foot 3518 to extend or protrude outside the housing 3504, thereby causing the biasing mechanism 3506 (and the biasing mechanism carrier 3512) to rotate in a second direction so that the administration interface release mechanism 3510 also rotates to a position in which it interacts with the administration interface lock mechanism 3508 in a locking manner. This results in the administration interface lock mechanism 3508 being rotated to and maintained in an "up" position so that the administration interface carrier 3502 is moved away from the administration site and locked in place in a vertically raised position so that the administration interface is in the retracted position and cannot be used to administer a therapeutic agent.

VI. Exemplary Components and Methods for Maintaining Sterility in Automatic Injection Devices Exemplary embodiments provide exemplary components for use in automatic injection devices for maintaining sterility of the therapeutic agent and the therapeutic agent administration pathway in the devices to avoid the need for aseptic assembly. Exemplary embodiments also provide automatic injection devices that use the exemplary components to maintain sterility, and methods for using automatic injection devices including such components in a manner that maintains sterility of the devices.

A sterility barrier is maintained around the therapeutic agent contained in exemplary automatic injection device and the administration pathway taken by the therapeutic agent before and during administration to a patient. In exemplary embodiments, the barrel portion of a syringe or cartridge for holding the therapeutic agent may be sterilized prior to filling with the therapeutic agent. A sterile bung may be placed in the barrel portion of the syringe or cartridge assembly to seal the therapeutic agent inside the barrel portion. The containment of the therapeutic agent inside the wearable automatic injection device by the sterile barrel portion and the sterile bung maintains sterility of the therapeutic agent after assembly of the device.

An administration interface button may be provided between the barrel portion and an administration interface for administering the therapeutic agent to the patient. The administration interface button may include a sterile fluid path and a sterile pierceable septum provided in the vicinity of an piercing needle. The sterilized piercing needle (e.g., a single needle, multiple needles, a needle-free pad, a needle-free patch, and the like) may be provided in the vicinity of the sterile septum in the administration interface button for piercing the septum and establishing fluid communication with the barrel portion. One or more sterile covers may enclose the septum in the administration interface button in a sterility barrier. That is, in exemplary embodiments, the sterile barrel portion, the sterile piercing needle, the sterile septum and septum cover, the sterile administration interface, and the administration interface cover may be cooperatively configured to create a sterility barrier around the therapeutic agent before and during administration to a patient. The sterility barrier may eliminate the need for the patient to swab the septum with alcohol before piercing the septum during administration of the therapeutic agent, as is conventionally done.

Exemplary components for providing a sterility barrier in an automatic injection device are illustrated in FIGS. 1A, 2A, 6A, and 7A and are described in this section in connection with FIGS. 1A and 2A. Components of FIGS. 6A and 8A that are similar to the components of FIGS. 1A and 2A are described in connection with FIGS. 1A and 2A in this section.

For example, exemplary devices 100/200 of FIGS. 1A/2A include a sterile barrel portion 106/206, a sterile piercing needle 120/220, a sterile septum cover 115/215, a sterile administration interface 118/218 (illustrated as an injection needle), and an administration interface cover 122/222 (illustrated as a needle cover). The housing 102/202 of the device 100/200 may include an adhesive layer 126/226 for attaching the housing 102/202 to the patient and a protective film 128/228 for protecting the adhesive layer 126/226. The protective film 128/228 may be sterile in exemplary embodiments. The removal of the protective film 128/228 exposes the adhesive layer 126/226, allowing the patient to attach the housing 102/202 to his or her body or an article of clothing by placing the side with the adhesive layer 126/226 on the body or the article of clothing.

Exemplary automatic injection devices may be provided with components that facilitate in removal of the septum cover and the administration interface cover before administration. In some exemplary embodiments, the protective film 128/228 may provide a mechanism to remove the septum cover and the administration interface cover in one operation or in one step. The protective film may include a linking member that is connected to the administration interface cover 122/222 and the septum cover 115/215. The linking member may include a tether, a tab or other linkage mechanism. When the protective film 128/228 is removed, the linking member of the protective film 128/228 may remove the administration interface cover 122/222 and the septum cover 115/215 as well.

Exemplary devices may provide different mechanisms for removing the protective film from the housing of the device, and thereby removing the administration interface cover and the septum cover at the same time. In exemplary embodiments illustrated in FIGS. 1A and 2A, a removal mechanism 130/230, e.g., a tab, may be provided on the protective film 128/228 for removing the protective film 128/228 from the adhesive layer 126/226. The removal mechanism 130/130 may not be coupled to any portion of the packaging of the device (e.g., an overwrap, blister pack, bubble wrap, or other commercial packaging) such that the protective film 128/228 is still attached to the adhesive layer 126/226 when the device is removed from the packaging. The removal mechanism 130/230 may be gripped by the patient and pulled to remove the protective film 128/228 from the adhesive layer 126/226. In exemplary embodiments, one or more gripping components (e.g., a ring or textured surface) may be provided at the removal mechanism 130/230 to facilitate gripping and pulling of the removal mechanism 130/230. In order to administer the therapeutic agent, the patient may remove the automatic injection device from its packaging and pull the removal mechanism 130/230 to remove the protective film 128/228 and expose the adhesive layer 126/226. When the removal mechanism 130/230 is pulled to remove the protective film 128/228, the linking member of the film 128/228 removes the administration interface cover 122/222 and the septum cover 115/215 as well, thus preparing the device for placement on the patient or his/her clothing for administration.

Figure 36:
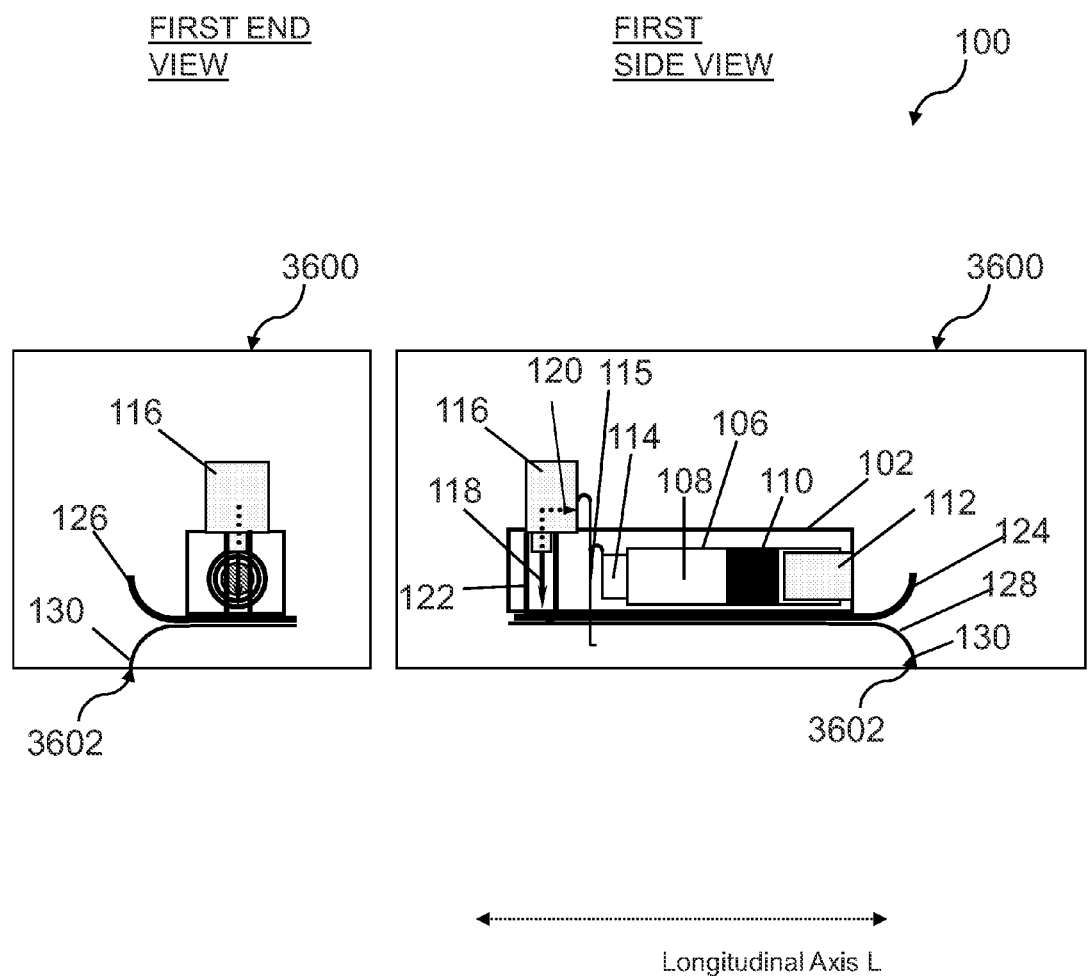
FIG. 36 illustrates a first end view and a first side view of the exemplary wearable device of FIG. 1A in a pre-administration state within an outer packaging in which a removal mechanism of a protective film is coupled to a portion of the outer packaging.

FIG. 36 illustrates another exemplary mechanism for removing the protective film 128 from the housing 102 of the device 100, and thereby removing the administration interface cover 122 and the septum cover 115. FIG. 36 illustrates the exemplary device 100 of FIG. 1A in a pre-administration state within an outer packaging 3600. The removal mechanism 130 may be provided on the protective film 128 for removing the protective film 128 from the adhesive layer 126. The removal mechanism 130 may be attached to an internal portion 3602 of the outer packaging 3600 of the device (e.g., an overwrap, blister pack, bubble wrap, or other commercial packaging, and the like) such that, when the device is removed from the packaging, the removal mechanism 130 remains attached to portion 3602 and the tugging force on the removal mechanism 130 at portion 3602 removes the protective film 128 from the adhesive layer 126. That is, when the device is fully outside the packaging, the protective film 128 has already been removed from the adhesive layer 126, and the adhesive layer is ready to be applied to the patient or his/her clothing for administration. In order to administer the therapeutic agent, the patient may remove the automatic injection device from its packaging which exposes the adhesive layer 126 and causes the linking member of the film 128 to automatically remove the administration interface cover 122, the piercing needle cover and the septum cover 115, thus preparing the device for placement on the patient or his/her clothing for administration. This method of preparing the device for administering the therapeutic agent may reduce the number of steps to be performed by the patient and thereby reduce user error.

Figure 37:
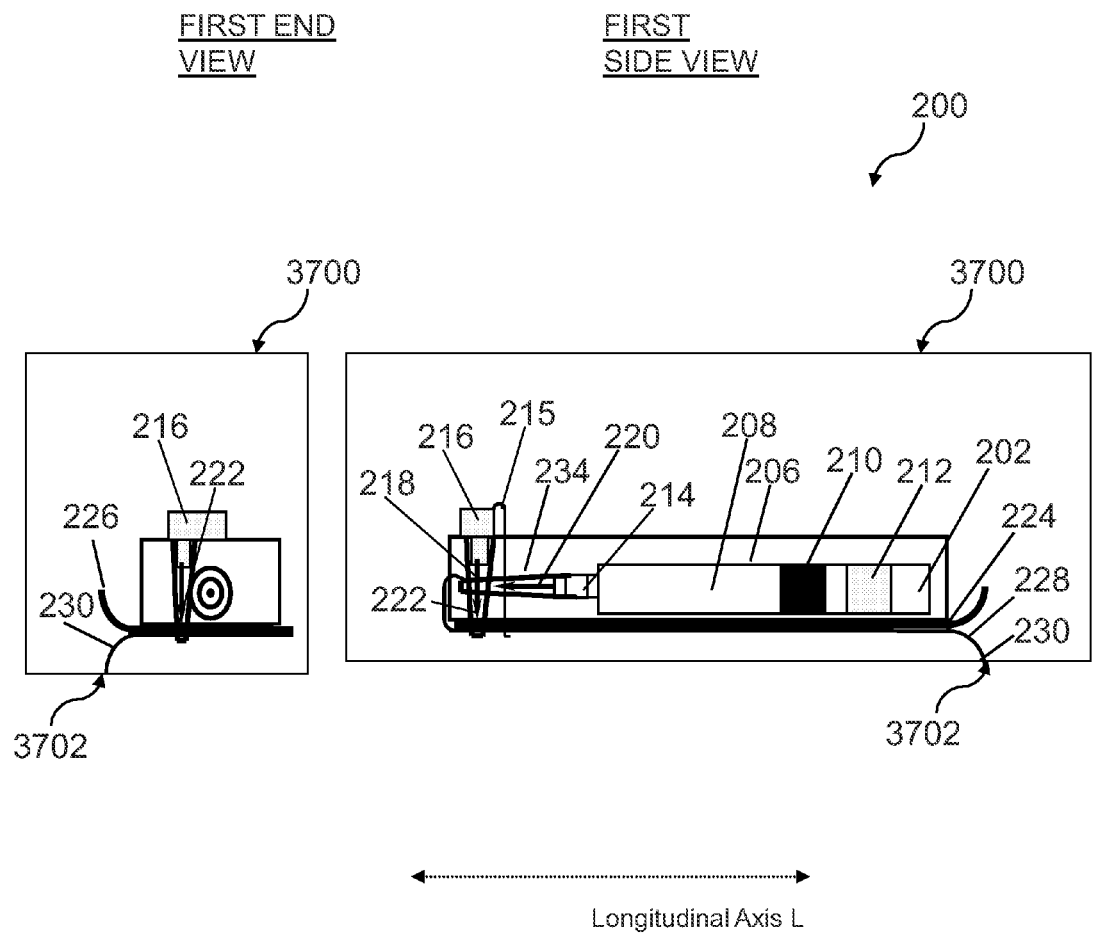
FIG. 37 illustrates a first end view and a first side view of the exemplary wearable device of FIG. 2A in a pre-administration state within an outer packaging in which a removal mechanism of a protective film is coupled to a portion of the outer packaging.

FIG. 37 illustrates another exemplary mechanism for removing the protective film 228 from the housing 202 of the device 200, and thereby removing the administration interface cover 222 and the septum cover 215. FIG. 37 illustrates the exemplary device 200 of FIG. 2A in a pre-administration state within an outer packaging 3700. The removal mechanism 230 may be provided on the protective film 228 for removing the protective film 228 from the adhesive layer 226. The removal mechanism 230 may be attached to an internal portion 3702 of the outer packaging 3700 of the device (e.g., an overwrap, blister pack, bubble wrap, or other commercial packaging, and the like) such that, when the device is removed from the packaging, the removal mechanism 230 remains attached to portion 3702 and the tugging force on the removal mechanism 230 at portion 3702 removes the protective film 228 from the adhesive layer 226. That is, when the device is fully outside the packaging, the protective film 228 has already been removed from the adhesive layer 226, and the adhesive layer is ready to be applied to the patient or his/her clothing for administration. In order to administer the therapeutic agent, the patient may remove the automatic injection device from its packaging which exposes the adhesive layer 226 and causes the linking member of the film 228 to automatically remove the administration interface cover 222, the piercing needle cover and the septum cover 215, thus preparing the device for placement on the patient or his/her clothing for administration. This method of preparing the device for administering the therapeutic agent may reduce the number of steps to be performed by the patient and thereby reduce user error.

VII. Exemplary Administration Interfaces

Exemplary embodiments provide exemplary administration interfaces suitable for use with exemplary automatic injection devices described above in connection with FIGS. 1-37 for administering a dose of a therapeutic agent to a patient. Exemplary embodiments also provide automatic injection devices that use the exemplary administration interfaces to administer a dose of a therapeutic agent to a patient. Exemplary administration interfaces may be provided integrally in an automatic injection device or as a separate component, e.g., a needle-free patch or an attachment, couplable to an automatic injection device. Exemplary administration interfaces may be configured for different types of administration including, but not limited to, subcutaneous, intradermal, intramuscular, topical, and the like. The flow rate of the therapeutic agent achieved by exemplary devices may vary based on one or more factors including, but not limited to, the type of application, the therapeutic agent, and the like. For example, subcutaneous and intramuscular administrations may be conducted at faster rates than topical, and intradermal administrations. In an exemplary embodiment, the administration interface may be configured based on the desired flow rate. For example, the inner diameter of the administration interface may be increased to achieve higher flow rates of the therapeutic agent.

Exemplary administration interfaces may be used to transport a therapeutic agent into or across biological barriers including, but not limited to the skin (or parts thereof), the blood-brain barrier, mucosal tissue (e.g., oral, nasal, vaginal, urethral, gastrointestinal, respiratory), blood vessels, lymphatic vessels, cell membranes, and the like. The biological barriers can be in humans or other types of animals, as well as in plants, insects or other organisms, including bacteria, yeast, fungi, embryos, and the like. A target biological barrier may be located within normal, intact tissue. A target biological barrier may be located within damaged or diseased tissue, such as a wound or lesion. Exemplary administration interfaces may be applied to tissue externally or internally with the aid of a catheter or laparoscope. For certain applications, such as for administration of a therapeutic agent to an internal tissue, exemplary administration interfaces may be surgically implanted. Exemplary embodiments may provide administration interfaces for administering a therapeutic agent across biological barriers using microneedle devices.

Exemplary administration interfaces may include one or more skin-piercing components configured for administering a therapeutic agent including, but are not limited to, a single needle/minineedle/microneedle, multiple needles/minineedles/microneedles, a needle/minineedle/microneedle coupled to a tubing, multiple needles/minineedles/microneedles coupled to a tubing, and the like. The needles, minineedles and/or microneedles used in exemplary administration interfaces may be dissolvable in some exemplary embodiments.

Exemplary administration interfaces may also include one or more components, e.g., a needle-free pad and/or a needle-free patch, that may be applied to a patient for performing a topical administration of a therapeutic agent. An exemplary component for such applications may include a reservoir in fluid communication with a barrel portion containing a therapeutic agent, and a drug-permeable membrane that allows the therapeutic agent from the reservoir to diffuse through the membrane and onto the skin surface. Other exemplary components may include flexible or rigid structures that form a pouch when in contact with the skin, with the skin forming a surface of the pouch. The pouch may fill with the therapeutic agent from the reservoir, allowing the therapeutic agent to be absorbed by or diffuse through the skin over extended periods of time. In some exemplary embodiments, the skin may be pre-treated before an exemplary administration interface is applied to the skin for a topical application.

Exemplary administration interfaces may be formed of any suitable material including, but not limited to, a polymer material (e.g., a medical grade polymer), metal, glass, silicone crystals, and the like. Exemplary administration interfaces may include one or more injection needles that are hollow and/or that have fluid channels.

An exemplary administration interface may have any suitable dimension, shape and configuration suitable for administering the dose to the patient by any suitable method including, but not limited to, intramuscularly, topically, subcutaneously, intradermally, and the like. Suitable administration interfaces may have a length configured or selected to provide an administration depth suitable for the desired therapy. For example, subcutaneous injections typically penetrate about six to ten millimeters into the skin. In an exemplary embodiment, the administration interface may have a length of about twelve mm and may be administered to a depth of about seven mm into the skin.

Suitable administration interfaces may have a wall thickness suitable to provide sufficient mechanism strength, a height, a diameter suitable to allow a desired flow rate of the therapeutic agent while minimizing patient sensation, and a tip geometry suitable for the desired therapy while minimizing patient sensation. Suitable administration interfaces may be configured as needed to minimize patient sensation as allowed by therapy. The length and thickness (gauge) of the injection needle may be configured based on one or more factors including, but not limited to, the type of administration (e.g., subcutaneous, intramuscular, etc.), the age of the patient, the body mass of the patient, the therapeutic agent, and the like. In some exemplary embodiments, injection needles for subcutaneous injections may have exemplary thicknesses of between about 23 gauge and about 25 gauge and exemplary lengths of between about seven mm and about fifteen mm, but are not limited to these exemplary ranges. In some exemplary embodiments, injection needles for intramuscular injections may have exemplary thicknesses of between about 22 gauge and 25 gauge and exemplary lengths of between about ten mm and about fifty mm.

In some exemplary embodiments, the injection needles may be micro-needles, i.e., structures having a height above the surface from which they protrude of about 500 micrometers or less. In some instances, exemplary micro-needles may have a height of about 250 micrometers or less.

In some exemplary embodiments, as illustrated in FIGS. 1A-1F, 2A-2F, 6A-6C, 7A-7C, 15-17, 36, and 37 an administration interface may include a single injection needle. In some other exemplary embodiments, an administration interface may include a single injection needle coupled to and in fluid communication with one or more ducts.

In exemplary embodiments, the type and dimensions of the administration interface may be used to configure one or more aspects of the automatic injection device including, but not limited to, the housing, the mechanism for applying the device to the administration site, the internal fluid path and geometry within the device, and the like.

VIII. Incorporation by Reference

The entire contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and may be used in conjunction with or substituted for components and methods described elsewhere in the disclosure within the scope of the invention.

IX. Equivalents

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

What is claimed is:

1. A wearable automatic injection device operable without electrical power for administering a therapeutic agent to a patient, the wearable automatic injection device comprising:
   a housing comprising a patient contact portion for contacting the patient;
   an administration assembly moveably disposed in the housing holding an administration interface for administering the therapeutic agent to the patient, the administration assembly moveable between a retracted position in which the administration interface does not protrude outside the housing and an extended position in which the administration interface protrudes outside the housing;
   a vessel provided in the housing for holding the therapeutic agent;

a plunger actuation mechanism moveably disposed in the vessel for ejecting the therapeutic agent from the vessel into the administration assembly; and an administration interface locking mechanism for automatically locking the administration interface in the retracted position within the housing in a pre-administration state and a post-administration state.

2. The wearable automatic injection device of claim 1, further comprising:

a retraction trigger responsive to a change of state of the wearable automatic injection device from an administration state to a post-administration state; and a retraction mechanism for automatically retracting the administration assembly from the extended position in the administration state to the retracted position in the post-administration state upon triggering by the retraction trigger.

3. The wearable automatic injection device of claim 1, wherein the vessel comprises a syringe.

4. The wearable automatic injection device of claim 3, wherein the syringe comprises: a barrel portion for holding the therapeutic agent; and a piercing needle coupled to a distal end of the barrel portion for establishing fluid communication between the barrel portion of the syringe and the administration assembly.

5. The wearable automatic injection device of claim 4, wherein the administration assembly comprises:

a septum that is pierceable by the piercing needle of the syringe; and a fluid conduit extending between the administration interface and the septum, wherein piercing of the septum by the piercing needle of the syringe couples the barrel portion of the syringe and the administration interface.

6. The wearable automatic injection device of claim 5, wherein the piercing needle of the syringe is spaced from the septum when the device is in a pre-administration state, and wherein the piercing needle pierces the septum when the device is in an administration state.

7. The wearable automatic injection device of claim 1, wherein the vessel comprises a cartridge.

8. The wearable automatic injection device of claim 7, wherein the cartridge comprises a barrel portion for holding the therapeutic agent; and a septum that is pierceable by a piercing needle.

9. The wearable automatic injection device of claim 8, wherein the administration assembly comprises:

the piercing needle for establishing fluid communication between the barrel portion of the cartridge and the administration interface; and a fluid conduit provided between the administration interface and the piercing needle for establishing fluid communication between the administration interface and the barrel portion of the cartridge.

10. The wearable automatic injection device of claim 9, wherein piercing of the septum by the piercing needle of the administration assembly establishes fluid communication between the barrel portion of the cartridge and the administration interface.

11. The wearable automatic injection device of claim 10, wherein the septum of the cartridge is spaced from the piercing needle of the administration assembly when the device is in a pre-administration state, and wherein the piercing needle pierces the septum when the device is in an administration state.

12. The wearable automatic injection device of claim 1, wherein the vessel is moveably disposed within the housing.

13. The wearable automatic injection device of claim 12, wherein the vessel is moveable between a first position in a pre-administration state and a second position in an administration state.

14. The wearable automatic injection device of claim 13, further comprising:

a vessel actuator for automatically actuating the vessel from the first position to the second position.

15. The wearable automatic injection device of claim 14, wherein a fluid pathway is established between the administration assembly and the vessel, when the administration assembly is in the extended position and the vessel is in the second position in the administration state.

16. The wearable automatic injection device of claim 1, wherein the plunger actuation mechanism administers the therapeutic agent to the patient at a controlled linear rate.

17. The wearable automatic injection device of claim 1, wherein the plunger actuation mechanism further comprises:

a plunger configured to exert an expulsion force to the therapeutic agent in the vessel;

a source of a working fluid for providing a hydraulic pressure to the plunger; and a fluid conduit provided between the source of the working fluid and the plunger.

18. The wearable automatic injection device of claim 17, wherein the plunger actuation mechanism further comprises:

a damping mechanism coupled to the plunger and the source of the working fluid to regulate the ejection of the therapeutic agent from the vessel.

19. The wearable automatic injection device of claim 18, wherein the damping mechanism comprises a flow restrictor for maintaining a first hydraulic pressure downstream of the flow restrictor toward the vessel at a lower pressure than a second hydraulic pressure upstream of the flow restrictor toward the source of the working fluid.

20. The wearable automatic injection device of claim 19, wherein the flow restrictor is coupled to a retraction trigger, wherein administration of the therapeutic agent in the vessel causes the flow restrictor to activate the retraction trigger, and wherein activation of the retraction trigger automatically retracts the administration assembly from the extended position to the retracted position.

21. The wearable automatic injection device of claim 1, wherein the administration interface locking mechanism comprises:

a barrier mechanism moveably disposed over an administration interface aperture in the housing;

wherein the administration interface aperture allows the administration interface to protrude outside the housing when the barrier mechanism is in a first position; and wherein the administration interface aperture prevents the administration interface from protruding outside the housing when the barrier mechanism is in a second position.

22. The wearable automatic injection device of claim 1, wherein the administration interface locking mechanism comprises:

an administration interface lock release mechanism responsive to retraction of the administration assembly from the extended position in the administration state to the retraction position in the post-administration state; and a pivoting member coupled to the administration interface and to the administration interface lock release mechanism;

wherein activation of the administration interface lock release mechanism causes the pivoting member to pivot the administration interface away from an administration interface aperture in the housing.

23. The wearable automatic injection device of claim 1, wherein the therapeutic agent comprises a TNFα inhibitor.

24. The wearable automatic injection device of claim 1, wherein, after insertion of the therapeutic agent in the vessel, a sterility barrier is maintained around the therapeutic agent contained in the vessel and an administration pathway taken by the therapeutic agent during administration to the patient.

25. The wearable automatic injection device of claim 24, wherein aseptic assembly of the automatic injection device is not required for maintaining sterility of the therapeutic agent, one or more skin penetrating surfaces of the administration interface and the administration pathway taken by the therapeutic agent during administration to the patient.

26. The wearable automatic injection device of claim 24, wherein the sterility barrier is provided by:
a sterile barrel portion of the vessel for holding the therapeutic agent;
a sterile piercing needle for establishing a fluid conduit between the barrel portion of the vessel and the administration interface;
a sterile septum of the administration assembly that is pierceable by the piercing needle;
a sterile fluid conduit of the administration assembly extending between the administration interface and the septum, wherein piercing of the septum by the piercing needle of the vessel establishes fluid communication between the barrel portion of the vessel and the administration interface; and
the administration interface which is sterile.

27. The wearable automatic injection device of claim 26, further comprising:
a septum cover for covering and maintaining sterility of the septum;
an administration interface cover for covering and maintaining sterility of the administration interface and the fluid conduit coupled to the administration interface; and
a piercing needle cover for covering and maintaining sterility of the piercing needle and the fluid conduit coupled to the piercing needle.

28. The wearable automatic injection device of claim 27, further comprising:
a protective film attached to at least a portion of the housing, the protective film coupled to the septum cover, the administration interface cover and the piercing needle cover such that removal of the protective film from the housing automatically removes the septum cover, the administration interface cover and the piercing needle cover.

29. The wearable automatic injection device of claim 28, wherein the protective film comprises:
an attachment mechanism attached to a package holding the automatic injection device such that removal of the device from the package removes the protective film from the housing of the device, the removal of the protective film removing the septum cover, the administration interface cover and the piercing needle cover.

30. The wearable automatic injection device of claim 28, wherein the protective film comprises:
a removal mechanism configured to be pulled in order to remove the protective film from the housing of the device, the removal of the protective film removing the septum cover, the administration interface cover and the piercing needle cover.

31. A method for administering a therapeutic agent to a patient, the method comprising:
providing a wearable automatic injection device operable without electrical power, comprising:
a housing comprising a patient contact portion for contacting the patient,
an administration assembly moveably disposed in the housing holding an administration interface for administering the therapeutic agent to the patient, the administration assembly moveable between a retracted position in which the administration interface does not protrude outside the housing and an extended position in which the administration interface protrudes outside the housing,
a vessel provided in the housing for holding the therapeutic agent,
a plunger actuation mechanism moveably disposed in the vessel for ejecting the therapeutic agent from the vessel into the administration assembly, and
a barrier mechanism moveably disposed over an administration interface aperture in the housing,
securing the wearable automatic injection device to the body of the patient or an article of clothing on the patient using the patient contact portion of the housing; and
administering a volume of the therapeutic agent to the body of the patient using the wearable automatic injection device.

32. The method of claim 31, wherein the wearable automatic injection device further comprises:
a retraction trigger responsive to a change of state of the wearable automatic injection device from an administration state to a post-administration state; and
a retraction mechanism for automatically retracting the administration assembly from the extended position in the administration state to the retracted position in the post-administration state upon triggering by the retraction trigger.

33. The method of claim 31, wherein the vessel comprises a syringe.

34. The method of claim 33, wherein the syringe comprises:
a barrel portion for holding the therapeutic agent; and
a piercing needle coupled to a distal end of the barrel portion for establishing fluid communication between the barrel portion of the syringe and the administration assembly.

35. The method of claim 34, wherein the administration assembly comprises:
a septum that is pierceable by the piercing needle of the syringe; and
a fluid conduit extending between the administration interface and the septum, wherein piercing of the septum by the piercing needle of the syringe couples the barrel portion of the syringe and the administration interface.

36. The method of claim 35, wherein the piercing needle of the syringe is spaced from the septum when the device is in a pre-administration state, and wherein the piercing needle pierces the septum when the device is in an administration state.

37. The method of claim 31, wherein the vessel comprises a cartridge.

38. The method of claim 37, wherein the cartridge comprises:
- a barrel portion for holding the therapeutic agent; and
- a septum that is pierceable by a piercing needle.

39. The method of claim 38, wherein the administration assembly comprises:
- the piercing needle for establishing fluid communication between the barrel portion of the cartridge and the administration interface; and
- a fluid conduit provided between the administration interface and the piercing needle for establishing fluid communication between the administration interface and the barrel portion of the cartridge.

40. The method of claim 39, wherein piercing of the septum by the piercing needle of the administration assembly establishes fluid communication between the barrel portion of the cartridge and the administration interface.

41. The method of claim 40, wherein the septum of the cartridge is spaced from the piercing needle of the administration assembly when the device is in a pre-administration state, and wherein the piercing needle pierces the septum when the device is in an administration state.

42. The method of claim 31, wherein the plunger actuation mechanism administers the therapeutic agent to the patient at a controlled linear rate.

43. The method of claim 31, wherein the plunger actuation mechanism further comprises:
- a plunger configured to exert an expulsion force to the therapeutic agent in the vessel;
- a source of a working fluid for providing a hydraulic pressure to the plunger; and
- a fluid conduit provided between the source of the working fluid and the plunger.

44. The method of claim 43, wherein the plunger actuation mechanism further comprises:
- a damping mechanism coupled to the plunger and the source of the working fluid to regulate the ejection of the therapeutic agent from the vessel.

45. The method of claim 44, wherein the damping mechanism comprises a flow restrictor for maintaining a first hydraulic pressure downstream of the flow restrictor toward the vessel at a lower pressure that a second hydraulic pressure upstream of the flow restrictor toward the source of the working fluid.

46. The method of claim 45, wherein the flow restrictor is coupled to a retraction trigger, wherein administration of the therapeutic agent in the vessel causes the flow restrictor to activate the retraction trigger, and wherein activation of the retraction trigger automatically retracts the administration assembly from the extended position to the retracted position.

47. The method of claim 31, wherein the wearable automatic injection device further comprises:
- an administration interface locking mechanism for automatically locking the administration interface in the retracted position within the housing in a post-administration state, the administration interface locking mechanism includes the barrier mechanism.

48. The method of claim 47,
- wherein the administration interface aperture allows the administration interface to protrude outside the housing when the barrier mechanism is in a first position; and
- wherein the administration interface aperture prevents the administration interface from protruding outside the housing when the barrier mechanism is in a second position.

49. The method of claim 47, wherein the administration interface locking mechanism comprises:
- an administration interface lock release mechanism responsive to retraction of the administration assembly from the extended position in an administration state to the retraction position in the post-administration state; and
- a pivoting member coupled to the administration interface and to the administration interface lock release mechanism;
- wherein activation of the administration interface lock release mechanism causes the pivoting member to pivot the administration interface away from an administration interface aperture in the housing.

* * * * *

SEQUENCE LISTING

<160> NUMBER OF SEQ ID NOS: 35

<210> SEQ ID NO 1
<211> LENGTH: 107
<212> TYPE: PRT
<213> ORGANISM: Artificial
<220> FEATURE:
<223> OTHER INFORMATION: D2E7 light chain variable region

<400> SEQUENCE: 1

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
            100                 105
```

<210> SEQ ID NO 2
<211> LENGTH: 121
<212> TYPE: PRT
<213> ORGANISM: Artificial
<220> FEATURE:
<223> OTHER INFORMATION: D2E7 heavy chain variable region

<400> SEQUENCE: 2

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

<210> SEQ ID NO 3
<211> LENGTH: 9
<212> TYPE: PRT
<213> ORGANISM: Artificial
<220> FEATURE:
<223> OTHER INFORMATION: D2E7 light chain variable region CDR3
<221> NAME/KEY: VARIANT
<222> LOCATION: 9
<223> OTHER INFORMATION: Xaa = Any Amino Acid

<400> SEQUENCE: 3

```
Gln Arg Tyr Asn Arg Ala Pro Tyr Xaa
1               5

<210> SEQ ID NO 4
<211> LENGTH: 12
<212> TYPE: PRT
<213> ORGANISM: Artificial
<220> FEATURE:
<223> OTHER INFORMATION: D2E7 heavy chain variable region CDR3
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial
<220> FEATURE:
<223> OTHER INFORMATION: D2E7 heavy chain variable region CDR1

<400> SEQUENCE: 8

Asp Tyr Ala Met His
1               5

<210> SEQ ID NO 9
<211> LENGTH: 107
<212> TYPE: PRT
<213> ORGANISM: Artificial
```

```
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial
<220> FEATURE:
<223> OTHER INFORMATION: 2SD4 light chain variable region CDR3

<400> SEQUENCE: 11

Gln Lys Tyr Asn Ser Ala Pro Tyr Ala
 1               5

<210> SEQ ID NO 12
<211> LENGTH: 9
<212> TYPE: PRT
<213> ORGANISM: Artificial
<220> FEATURE:
```

```
<223> OTHER INFORMATION: EP B12  light chain variable region CDR3

<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
<211> LENGTH: 9
<212> TYPE: PRT
<213> ORGANISM: Artificial
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial
<220> FEATURE:
<223> OTHER INFORMATION: VLL0G7 light chain variable region CDR3
```

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial
<220> FEATURE:
<223> OTHER INFORMATION: VLLOG9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial
<220> FEATURE:
<223> OTHER INFORMATION: VLLOH1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial
<220> FEATURE:
<223> OTHER INFORMATION: VLLOH10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial
<220> FEATURE:
<223> OTHER INFORMATION: VL1B7 light chain variable region CDR3

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial
<220> FEATURE:
<223> OTHER INFORMATION: VL1C1 light chain variable region CDR3

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial
<220> FEATURE:
<223> OTHER INFORMATION: VL0.1F4 light chain variable region CDR3

```
<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial
<220> FEATURE:
<223> OTHER INFORMATION: L0E7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial
<220> FEATURE:
<223> OTHER INFORMATION: VH1A11 heavy chain variable region CDR3

<400> SEQUENCE: 30
```

```
Ala Ser Tyr Leu Ser Thr Ser Ser Leu Asp Asp
 1               5                   10

<210> SEQ ID NO 31
<211> LENGTH: 12
<212> TYPE: PRT
<213> ORGANISM: Artificial
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
 1               5                   10

<210> SEQ ID NO 32
<211> LENGTH: 12
<212> TYPE: PRT
<213> ORGANISM: Artificial
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
 1               5                   10

<210> SEQ ID NO 33
<211> LENGTH: 12
<212> TYPE: PRT
<213> ORGANISM: Artificial
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
 1               5                   10

<210> SEQ ID NO 34
<211> LENGTH: 12
<212> TYPE: PRT
<213> ORGANISM: Artificial
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
 1               5                   10

<210> SEQ ID NO 35
<211> LENGTH: 12
<212> TYPE: PRT
<213> ORGANISM: Artificial
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                   10
```